United States Patent
Lim et al.

(10) Patent No.: US 11,913,946 B2
(45) Date of Patent: Feb. 27, 2024

(54) BIMETAL-CONDUCTIVE POLYMER JANUS COMPOSITE NANOSTRUCTURE HAVING ELECTRICAL STIMULUS RESPONSE, COLLOID SELF-ASSEMBLED STRUCTURE THEREOF, PREPARING METHOD, AND BIO-SENSING, BIO-IMAGING, DRUG DELIVERY AND INDUSTRIAL APPLICATION

(71) Applicant: Industry-University Cooperation Foundation Hanyang University Erica Campus, Ansan-si (KR)

(72) Inventors: Dong Woo Lim, Ansan-si (KR); Eun Young Hwang, Seoul (KR)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 1134 days.

(21) Appl. No.: 16/324,278

(22) PCT Filed: Aug. 9, 2017

(86) PCT No.: PCT/KR2017/008620
§ 371 (c)(1),
(2) Date: Feb. 8, 2019

(87) PCT Pub. No.: WO2018/030785
PCT Pub. Date: Feb. 15, 2018

(65) Prior Publication Data
US 2019/0170743 A1 Jun. 6, 2019

(30) Foreign Application Priority Data

Aug. 9, 2016 (KR) .................. 10-2016-0101255
Aug. 8, 2017 (KR) .................. 10-2017-0100356
Aug. 8, 2017 (KR) .................. 10-2017-0100357
Aug. 8, 2017 (KR) .................. 10-2017-0100358
Aug. 8, 2017 (KR) .................. 10-2017-0100359

(51) Int. Cl.
*G01N 33/543* (2006.01)
*G01N 33/533* (2006.01)
*A61K 9/51* (2006.01)
*G01N 21/65* (2006.01)

(52) U.S. Cl.
CPC ...... *G01N 33/54346* (2013.01); *A61K 9/5115* (2013.01); *G01N 33/533* (2013.01); *G01N 33/54373* (2013.01); *G01N 21/658* (2013.01)

(58) Field of Classification Search
None
See application file for complete search history.

(56) References Cited

PUBLICATIONS

Xing, S., et al., "Reducing the Symmetry of Bimetallic Au@Ag Nanoparticles by Exploiting Eccentric Polymer Shells", JACS, pp. 9537-9539 (Year: 2010).*
Fan, M., et al., "Surface-enhanced Raman scattering (SERS) from Au:Ag bimetallic nanoparticles: the effect of the molecular probe", Royal Society of Chemistry, pp. 509-515 (Year: 2013).*
Iida, R., et al., "Synthesis of Janus-Like Gold Nanoparticles with Hydrophilic/Hydrophobic Faces by Surface Ligand Exchange and Their SelfAssemblies in Water", Langmuir, pp. 4054-4062 (Year: 2015).*
Jia, L., et al., "Unconventional Assembly of Bimetallic Au—Ni Janus Nanoparticles on Chemically Modified Silica Spheres", Chemistry a European Journal, pp. 2065-2070 (Year: 2014).*
Tokonami, Shiho et al., "Novel Synthesis, Structure, and Oxidation Catalysis of Ag/Au Bimetallic Nanoparticles", The Journal of Physical Chemistry C, vol. 114, 2010 (pp. 10336-10341).
Wang, Xiufang et al., "Assembly of Dandelion-like Au/PANI Nanocomposites and their Application as SERS Nanosensors", *Biosensors and Bioelectronics*, vol. 26, 2011 (pp. 3063-3067).
Chen, Shouhui et al., "Self-Assembly of Gold Nanoparticles to Silver Microspheres as Highly Efficient 3D SERS Substrates", *Nanoscale Research Letters*, vol. 8, Thesis No. 168, 2013, (7 pages in English).
Gonzalez, Carlos M. et al., "Photochemical Synthesis of Bimetallic and Anisotropic Au-containing Nanoparticles using a one-step Protocol", *Journal of Materials Chemistry A*, vol. 2, 2014, (pp. 17574-17585).
Hwang, Eunyoung et al., "Self-assembly of Anisotropic Bimetal-Polymer Nanoparticles", The *Polymer Society of Korea*, Oct. 2015 (1 page in English).
Hwang, Eunyoung et al., "Bimetallic Nanoclusters with Anisotropic Polymer Shell for Photonics-based Biosensing", *The Polymer Society of Korea*, Apr. 2016 (1 page in English).
Hwang, Eunyoung et al., "Synthesis and Characterization of Bimetallic Core-Satellite Nanostructures with Eccentric Polymer Shell", *The Polymer Society of Korea*, Apr. 2016 (1 page in English).
Hwang, Eunyoung et al., "Clustered Architectures of Anisotropic Bimetal-polymer Nonopatricles for Surface Enhanced Raman Scattering-based Biosensing", *2016 Annual Spring Meeting of The Korean BioChip Society* (1 page in English and 216 pages in Korean).
Internatioanl Search Report dated Dec. 7, 2017 in corresponding International Patent Application No. PCT/KR2017/008620 (3 pages in English and 3 pages in Korean).

* cited by examiner

*Primary Examiner* — Michael G. Hartley
*Assistant Examiner* — Lance W Rider
(74) *Attorney, Agent, or Firm* — NSIP Law

(57) ABSTRACT

The present disclosure relates to a bimetal-conductive polymer Janus composite nanostructure having electrical stimulation responsiveness, a colloidal self-assembled structure thereof, a preparation method thereof and biosensing, bio-imaging, drug delivery and industrial application using the same.

14 Claims, 68 Drawing Sheets

BIMETAL-CONDUCTIVE POLYMER JANUS COMPOSITE NANOSTRUCTURE HAVING ELECTRICAL STIMULUS RESPONSE, COLLOID SELF-ASSEMBLED STRUCTURE THEREOF, PREPARING METHOD, AND BIO-SENSING, BIO-IMAGING, DRUG DELIVERY AND INDUSTRIAL APPLICATION

CROSS REFERENCE TO RELATED APPLICATIONS

This application is a U.S. National Stage Application of International Application No. PCT/KR2017/008620, filed on Aug. 9, 2017, which claims the benefit under 35 USC 119(a) and 365(b) of Korean Patent Application No. 10-2016-0101255, filed on Aug. 9, 2016, Korean Patent Application No. 10-2017-0100356, filed on Aug. 8, 2017, Korean Patent Application No. 10-2017-0100357, filed on Aug. 8, 2017, Korean Patent Application No. 10-2017-0100358, filed on Aug. 8, 2017 and Korean Patent Application No. 10-2017-0100359, filed on Aug. 8, 2017 in the Korean Intellectual Property Office.

BACKGROUND

1. Field of the Invention

The present disclosure relates to a bimetal-conductive polymer Janus composite nanostructure having electrical stimulation responsiveness, a colloidal self-assembled structure thereof, a preparation method thereof and biosensing, bioimaging, drug delivery and industrial application using the same.

2. Description of Related Art

A number of optical biosensors based on fluorescence (FL) and surface plasmon resonance (SPR) have been developed for detection application due to high sensitivity.

Raman spectroscopy has been studied for detection and identification of pathogens. Specifically, surface-enhanced Raman scattering (SERS) is drawing a lot of attentions in spectroscopic detection and identification of molecules, nucleic acids and cells mainly due to high sensitivity, narrow bandwidth and important multiplexing ability. Although the Raman spectroscopy has been used as a multipurpose tool for obtaining structure information of a material based on vibrational transition, the traditional Raman scattering technique is limited due to low sensitivity. In this regard, the SERS spectroscopy is a powerful analytical technique which provides a remarkable enhancement of signals up to $10^{14}$ times near the surface of a metal nanoparticle as compared to the Raman scattering. This enhancement results from the electromagnetic field nonuniformly distributed across the particle surface, i.e., the hot spot present in the sharp protrusion or nanoscale gap between the nanoparticles. Meanwhile, there have been many attempts to develop plasmon metal nanoparticles and utilize their useful optical properties and high SERS efficiency. The plasmon characteristics depend greatly on size, morphology and degree of aggregation.

Also, metal nanoparticles have been studied extensively in various applications including electronics, catalysts, bioimaging and surface-enhanced Raman spectroscopy due to their electrical, chemical and optical properties resulting from structure and size. In particular, multicomponent metal nanoparticles have new or improved optical properties in addition to the physicochemical properties of the respective components due to their synergistic effect, as compared to single-component metal nanoparticles.

SUMMARY OF THE INVENTION

The present disclosure is directed to providing a self-assembled bimetal-polymer Janus nanostructure, a self-assembled nanostructure thereof, a method for preparing the same and a metal nanoprobe, a drug delivery system and a method for detecting a target material based on surface-enhanced Raman scattering (SERS) using the same.

The present disclosure is also directed to providing a Janus nanostructure consisting of a core-satellite bimetal nanoparticle part and a polymer part, a method for preparing the same and a metal nanoprobe for detecting a target material based on surface-enhanced Raman scattering (SERS) and a method for detecting a target material based on SERS using the same.

The present disclosure is also directed to providing an asymmetric Janus nanoprobe for detecting a target material based on surface-enhanced Raman scattering (SERS), a method for preparing the same and a method for detecting a target material using the same.

The present disclosure is also directed to providing an anisotropic Janus nanostructure consisting of a bimetal nanoparticle part containing a metal nanorod cluster having directionality and a polymer part, a method for preparing the same and a method for detecting a target material based on surface-enhanced Raman scattering (SERS) using the same.

Invention 1:

The present disclosure provides a self-assembled bimetal-polymer Janus nanostructure consisting of: a bimetal nanocluster core; and a conductive polymer shell located radially around the core.

The bimetal nanocluster core consists of a first metal and a second metal surrounding the surface of the first metal.

The first metal and the second metal may respectively be selected from a group consisting of silver, gold, copper and a mixture thereof. However, any metal widely used in the art may be used without limitation.

The first metal and the second metal may be not identical.

The conductive polymer may be at least one selected from a group consisting of polypyrrole, polythiophene, poly(3,4-ethylenedioxythiophene) (PEDOT) and polyaniline, although not being necessarily limited thereto. Specifically, it may be polyaniline.

The bimetal nanocluster core may further contain a Raman dye.

The Raman dye refers to a Raman-active organic compound and any one widely used in the art may be used without limitation. Specific examples may be selected from a group consisting of MGITC (malachite green isothiocyanate), RBITC (rhodamine B isothiocyanate), rhodamine 6G, adenine, 4-aminopyrazolo(3,4-d)pyrimidine, 2-fluoroadenine, N6-benzoyladenine, kinetin, dimethylallylaminoadenine, zeatin, bromoadenine, 8-azaadenine, 8-azaguanine, 4-mercaptopyridine, 6-mercaptopurine, 4-amino-6-mercaptopyrazolo(3,4-d)pyrimidine, 8-mercaptoadenine, 9-aminoacridine and a mixture thereof, although not being necessarily limited thereto.

In the present disclosure, the bimetal refers to two metals having a metal core-metal shell structure.

In the present disclosure, the metal nanocluster is a term referring to an aggregate formed from aggregation of metal nanoparticles. It is a term generally used in the art.

In the present disclosure, the bimetal nanocluster refers to an aggregate formed from aggregation of bimetal nanoparticles having a core-shell structure.

In the present disclosure, the "Janus nanostructure" or a "hybrid nanostructure" refers to a nanostructure consisting of two different parts which are distinctly distinguished from each other physically and chemically (a bimetal nanocluster part (core) and a conductive polymer part (shell)).

The bimetal nanocluster consists of a first metal and a second metal surrounding the surface of the first metal. A conductive polymer part adheres to and grows on only one side of the bimetal nanocluster part, i.e., it is eccentrically deposited to form an asymmetrical Janus nanoparticle. The bimetal nanoparticles in the Janus nanoparticle are self-assembled through hydrophobic interaction, forming a bimetal nanocluster core and a polymer part located radially around the core in the form of a shell. The hydrophobic interaction of the bimetal nanoparticles in the Janus nanoparticle is achieved by inducing selective functionalization by covalently bonding ODA (octadecylamine) to the Janus nanoparticle.

In the present disclosure, the "Janus nanostructure", which has a bimetal nanocluster core-conductive polymer shell structure, is also called a "bimetal-polymer Janus nanoparticle", a "Janus nanoparticle" or a "Janus nano-probe". Also, in the present disclosure, the structure of "a bimetal nanocluster core and a polymer part located radially around the core in the form of a shell" is called a "superparticular structure".

In another aspect, the present disclosure provides a metal nanoprobe for biosensing and/or bioimaging measurement based on surface-enhanced Raman scattering (SERS) using Janus nanostructure according to the present disclosure.

The self-assembled bimetal-polymer Janus nanostructure according to the present disclosure may be provided as a metal nanoprobe for biosensing and/or bioimaging measurement based on surface-enhanced Raman scattering by containing a Raman dye.

In the present disclosure, the probe refers to a material which is capable of specifically binding to a target material to be detected and allows identification of the presence of the target material through the binding.

In the present disclosure, the nanoprobe refers to a nano-sized probe.

The term "nano" includes the size range understood by those of ordinary skill in the art. The size range may be specifically 0.1-1000 nm, more specifically 10-1000 nm, more specifically 20-500 nm, further more specifically 40-250 nm.

The present disclosure provides a fluorescence-based metal nanoprobe for biosensing and/or bioimaging measurement using the Janus nanostructure according to the present disclosure.

The self-assembled bimetal-polymer Janus nanostructure according to the present disclosure may be provided as a metal nanoprobe for fluorescence-based imaging measurement by containing a cyanine-based fluorescent molecule, a rhodamine-based fluorescent molecule, an oxazine-based fluorescent molecule, an Alexa-based fluorescent molecule, an FITC (fluorescein isothiocyanate) fluorescent molecule, a FAM (5-carboxy fluorescein) fluorescent molecule or a Texas Red fluorescent molecule. Specifically, the fluorescent dye ($R_2$) may be a fluorescent dye having Cy3, Cy5, fluorescein isothiocyanate (FITC), tetramethylrhodamine isothiocyanate (TRITC), Alexa, 4,4-difluoro-4-boro-3a,4a-diaza-s-indacene (BODIPY), Texas Red, biotin-rhodamine, coumarin, Cy, EvoBlue, oxazine, carbopyronine, naphthalene, biphenyl, anthracene, phenanthrene, pyrene, carbazole, etc. as a backbone or a derivative of the fluorescent dye. Specific examples may include CR110 (carboxyrhodamine 110), Rhodamine Green (trade name), TAMRA (carboxytetramethylrhodamine), TMR, carboxyrhodamine 6G (CR6G), ATTO655 (trade name), BODIPY FL (trade name, 4,4-difluoro-5,7-dimethyl-4-boro-3a,4a-diaza-s-indacene-3-propionic acid), BODIPY 493/503 (trade name, 4,4-difluoro-1,3,5,7-tetramethyl-4-boro-3a,4a-diaza-s-indacene-8-propionic acid), BODIPY R6G (trade name, 4,4-difluoro-5-(4-phenyl-1,3-butadienyl)-4-boro-3a,4a-diaza-s-indacene-3-propionic acid) BODIPY 558/568 (trade name, 4,4-difluoro-5-(2-thienyl)-4-boro-3a,4a-diaza-s-indacene-3-propionic acid), BODIPY 564/570 (trade name, 4,4-difluoro-5-styryl-4-boro-3a,4a-diaza-s-indacene-3-propionic acid), BODIPY 576/589 (trade name, 4,4-difluoro-5-(2-pyrrolyl)-4-boro-3a,4a-diaza-s-indacene-3-propionic acid), BODIPY 581/591 (trade name, 4,4-difluoro-5-(4-phenyl-1,3-butadienyl)-4-boro-3a,4a-diaza-s-indacene-3-propionic acid), Cy3 (trade name), Cy3B (trade name), Cy3.5 (trade name), Cy5 (trade name), Cy5.5 (trade name), EvoBlue10 (trade name), EvoBlue30 (trade name), MR121, ATTO 390 (trade name), ATTO 425 (trade name), ATTO 465 (trade name), ATTO 488 (trade name), ATTO 495 (trade name), ATTO 520 (trade name), ATTO 532 (trade name), ATTO Rho6G (trade name), ATTO 550 (trade name), ATTO 565 (trade name), ATTO Rho3B (trade name), ATTO Rho11 (trade name), ATTO Rho12 (trade name), ATTO Thio12 (trade name), ATTO 610 (trade name), ATTO 611X (trade name), ATTO 620 (trade name), ATTO Rho14 (trade name), ATTO 633 (trade name), ATTO 647 (trade name), ATTO 647N (trade name), ATTO 655 (trade name), ATTO Oxa12 (trade name), ATTO 700 (trade name), ATTO 725 (trade name), ATTO 740 (trade name), Alexa Fluor 350 (trade name), Alexa Fluor 405 (trade name), Alexa Fluor 430 (trade name), Alexa Fluor 488 (trade name), Alexa Fluor 532 (trade name), Alexa Fluor 546 (trade name), Alexa Fluor 555 (trade name), Alexa Fluor 568 (trade name), Alexa Fluor 594 (trade name), Alexa Fluor 633 (trade name), Alexa Fluor 647 (trade name), Alexa Fluor 680 (trade name), Alexa Fluor 700 (trade name), Alexa Fluor 750 (trade name), Alexa Fluor 790 (trade name), Rhodamine Red-X (trade name), Texas Red-X (trade name), 5(6)-TAMRA-X (trade name), 5TAMRA (trade name) and SFX (trade name).

The present disclosure provides a drug delivery system using the Janus nanostructure according to the present disclosure.

The drug delivery system may be responsive to electric field stimulation.

Specifically, the polymer part of the self-assembled bimetal-polymer Janus nanostructure according to the present disclosure exhibits responsiveness to electric field because it is formed of a conductive polymer. In the present disclosure, a drug is loaded into the polymer part through electrostatic interaction between the negatively charged drug and a positively charged conductive polymer monomer and a PEG-nanoparticle hydrogel is formed by adding the concentrated drug-loaded nanoparticle into a PEG solution and then irradiating UV. When a voltage of −1.5 V is applied, the drug is released as the electrostatic interaction is decreased due to deprotonation of the conductive polymer monomer (repeating unit) (FIGS. 6A-6D).

In another aspect, the present disclosure provides a method for preparing a self-assembled bimetal-polymer Janus nanostructure, including:

i) a step of preparing a metal nanoparticle forming a seed;
ii) a step of adding the seed metal nanoparticle to an aqueous solution in which a conductive polymer monomer and a surfactant are dissolved;
iii) a step of conducting an oxidation-reduction reaction between a metal ion and the conductive polymer monomer by adding a metal ion solution to the solution in which the seed metal nanoparticle is added in the step ii);
iv) a step of preparing a bimetal-polymer Janus nanoparticle by forming a bimetal nanoparticle part as the metal ion is reduced by receiving an electron donated by the conductive polymer and is deposited on the surface of the seed metal nanoparticle and forming a conductive polymer part asymmetrically as the conductive polymer monomer is oxidized, is deposited on only one side of the bimetal nanoparticle part and grows into a conductive polymer;
v) a step of adding ODA (octadecylamine) to a solution containing the Janus nanoparticle; and
vi) a step of forming a bimetal nanocluster core and a polymer shell located radially around the core through self-assembly as the bimetal nanoparticle in the Janus nanoparticle is covalently bonded to the ODA.

The method may further include, after the step iv), a step of attaching a Raman dye on the surface of the bimetal nanoparticle.

In an exemplary embodiment of the present disclosure, after adding two Raman dyes, RBITC and MGITC, to a colloid solution of the bimetal-polymer Janus nanoparticle, the RBITC and the MGITC is selectively adsorbed onto the bimetal nanocluster part by fixing onto the surface of the Au core-Ag shell bimetal nanoparticle through the isothiocyanate group (—N=C=S) of the Raman dyes.

The seed metal in the step i) may be selected from a group consisting of gold, silver, copper and a mixture thereof. However, without being necessarily limited thereto, any metal widely used in the art may be used without limitation.

The metal ion in the step iii) may be selected from a group consisting of gold ion, silver ion, copper ion and a mixture thereof.

Specifically, the gold ion may be selected from a group consisting of gold(III) chloride hydrate, chlorocarbonylgold, hydrogen tetrachloroaurate, hydrogen tetrachloroaurate hydrate, chlorotriethylphosphinegold, chlorotrimethylphosphinegold, dimethyl(acetylacetonate)gold, gold(I) chloride, gold cyanide, gold sulfide and a mixture thereof, although not being necessarily limited thereto. Specifically, it may be gold(III) chloride hydrate.

The silver ion may be selected from a group consisting of silver nitrate ($AgNO_3$), silver tetrafluoroborate ($AgBF_4$), silver trifluoromethanesulfonate ($AgCF_3SO_3$), silver perchlorate ($AgClO_4$), silver acetate ($Ag(CH_3COO)$), silver hexafluorophosphate ($AgPF_6$), $Ag(CF_3COO)$ and a mixture thereof, although not being necessarily limited thereto. Specifically, it may be silver nitrate.

The copper ion may be selected from a group consisting of copper(II) acetylacetonate ($Cu(acac)_2$), copper(I) chloride (CuCl), copper(II) chloride ($CuCl_2$), copper(II) hexafluoroacetylacetonate ($Cu(hfac)_2$), copper(II) trifluoroacetyl chloride (Cu(tfac)2), copper(II) dipivaloylmethanate ($Cu(dpm)_2$), copper(II) pentafluorodimethylheptanedione ($Cu(ppm)_2$), copper(II) heptafluorodimethyloctane ($Cu(fod)_2$), copper(II) iminopentanone ($Cu(acim)_2$), copper(II) hexafluoro[(trifluoroethyl)imino]pentanone ($Cu(nona-F)_2$), copper(II) acetylacetoethylenediamine ($Cu(acen)_2$), copper nitrate ($Cu(NO_3)_2$), copper sulfate ($CuSO_4$) and a mixture thereof, although not being necessarily limited thereto.

In an exemplary embodiment of the present disclosure, the bimetal nanocluster core may consist of the seed metal nanoparticle (first metal) and a second metal surrounding the surface of the seed metal.

The conductive polymer in the step ii) may be at least one selected from a group consisting of polypyrrole, polythiophene, poly(3,4-ethylenedioxythiophene) (PEDOT) and polyaniline, although not being necessarily limited thereto. Specifically, it may be polyaniline.

The growth into the conductive polymer in the step iv) may be achieved by surface-templated polymerization.

The "surface-templated polymerization" refers to a polymerization method based on an oxidation-reduction reaction whereby the conductive polymer polyaniline is deposited on the bimetal nanocluster through a spontaneous oxidation-reduction reaction between silver nitrate and an aniline monomer. Specifically, the polyaniline is deposited on the bimetal nanocluster through oxidation polymerization of the conductive polymer monomer as the aniline monomer having a primary amine group donates an electron to the silver nitrate and the silver ion receives the electron to balance the oxidation-reduction reaction.

The surfactant in the step ii) may be at least one selected from a group consisting of sodium dodecyl sulfate (SDS), sodium deoxycholate and Triton X-200, although not being necessarily limited thereto. Specifically, it may be SDS.

An experimental method for preparing the self-assembled bimetal-polymer Janus nanostructure according to the present disclosure and a superparticular structure thereof and an experimental method for SERS-based biosensing and/or application are schematically shown in FIGS. 1A-1C.

FIG. 1A shows the synthesis of a bimetal-polymer Janus nanoparticle and a superparticular structure thereof. First, a bimetal-polymer Janus nanoparticle is prepared through oxidation polymerization of an aniline monomer and further growth of an Ag nanoparticle. Specifically, after adding a concentrated Au nanoparticle to a solution containing aniline and a surfactant, SDS, an oxidation-reduction reaction is initiated by adding silver nitrate. A bimetal-polymer Janus nanoparticle consisting of a bimetal nanocluster part formed of an Au core and an Ag shell and a polymer part formed of poly(aniline) is prepared by incubating the resulting solution in a 3.6 mM SDS solution overnight. The compartmentalization of the bimetal-polymer Janus nanoparticle results from the balanced interfacial tension between the three-phase systems of Ag, poly(aniline) and water. The addition of SDS affects the interfacial tension between the two adjacent phases of poly(aniline)-Ag and poly(aniline)-water. Subsequently, the poly(aniline) polymer part is formed on one side of the Au nanoparticle to minimize total surface energy. Also, when the bimetal cluster part of the bimetal-polymer Janus nanoparticle is selectively functionalized with ODA containing a long hydrophobic alkyl chain, a superparticular structure is formed through directional self-assembly, wherein the bimetal cluster part faces oppositely through hydrophobic interaction. It may be because the ODA is covalently bonded to the surface of the bimetal cluster part through amide bonding between the carboxyl group of the Au nanoparticle and the primary amine group of the ODA.

FIG. 1B shows a spontaneous oxidation-reduction reaction between the aniline monomer and in silver nitrate for the synthesis of the bimetal-polymer Janus nanoparticle. The oxidation-reduction reaction involves electron transfer between two precursors whereby the aniline is oxidized to poly(aniline) and the silver nitrate is reduced to a particle. The aniline monomer having the primary amine group, which is an electron donor molecule, donates an electron to the silver nitrate and the silver nitrate receives the electron to balance the oxidation-reduction reaction. As seen from FIG. 1C, the superparticular structure of the bimetal-polymer Janus nanoparticle can be used as a new type of SERS nanoprobe for biosensing. Specifically, because the bimetal part is selectively functionalized with the Raman dye and ODA, a hot spot is formed between the gap of the bimetal nanoparticle through directional clustering. As a result, significant enhancement of Raman signals is induced and a specific antibody which is a portion of a target is introduced into the polymer part through molecular bonding. In the presence of a target, a sandwich immune complex consisting of the superparticular structure, the target and a magnetic bead is formed, which is washed in a magnetic field. Finally, the Raman scattering-based detection of the target is confirmed through Raman shift.

In another aspect, the present disclosure provides a method for detecting a target material based on surface-enhanced Raman scattering (SERS), including:
a) a step of preparing a sample solution containing a target material to be detected;
b) a step of immobilizing a first antibody for the target material onto a magnetic nanoparticle;
c) a step of immobilizing a second antibody for the target material onto a metal nanoprobe containing a Raman dye;
d) a step of forming an immune complex wherein the target material and the first antibody of the magnetic nanoparticle are conjugated by adding the first antibody-immobilized magnetic nanoparticle of the step b) to the sample solution of the step a);
e) a step of forming a sandwich immune complex of the second antibody of the metal nanoprobe, the target material and the first antibody of the magnetic nanoparticle by adding the second antibody-immobilized metal nanoprobe of the step c) to the solution containing the first antibody-conjugated immune complex of the step d);
f) a step of separating the magnetic nanoparticle and the metal nanoprobe not forming the sandwich immune complex using a magnetic field; and
g) a step of measuring a Raman signal of the sandwich immune complex.

In the present disclosure, the "sandwich immune complex" refers to an immune complex wherein an antibody, an antigen (target) and an antibody are bound with a sandwich shape in which the antigen is inserted between the antibodies.

A SERS-based immunoassay method for detection of a target protein is schematically shown in FIG. 7. In the step 1, a magnetic bead to which anti-human IgG mAb or anti-human CEA mAb is bound is added to a solution containing IgG or CEA at various concentrations. A target is selectively captured by the magnetic bead by applying an external magnetic field, which is resuspended in PBS. In the step 2, a sandwich immune complex consisting of a magnetic bead, a target protein and a SERS-based nanoprobe is formed by adding a SERS nanoprobe to which anti-human IgG pAb or anti-human CEA pAb is bound to a solution. Then, the unbound SERS nanoprobe is removed by applying a magnetic field and the obtained sandwich immune complex is resuspended in PBS. In the final step, the SERS-based quantitative analysis of the target having linear correlation between the relative Raman intensity and the concentration of the target protein is confirmed from Raman shift in the Raman spectrum.

The target material may be a protein or a pathogen.

The protein may be selected from a group consisting of an antigen, a biological aptamer, a receptor, an enzyme and a ligand.

Invention 2:

The present disclosure provides a Janus nanostructure containing:
a core-satellite bimetal nanoparticle part consisting of a metal nanoparticle core onto which a ligand is adsorbed and a metal satellite reduced at the ligand-adsorbed site of the core; and
a conductive polymer part.

The ligand may be a negatively charged ligand or a ligand having two functional groups and the metal nanoparticle core may be a positively charged metal nanoparticle core or a negatively charged metal nanoparticle core.

The negatively charged ligand may be a polymeric ligand containing a charged repeating unit and the ligand having two functional groups may be a small-molecule ligand.

The polymeric ligand containing the charged repeating unit may be at least one selected from a group consisting of PSS (poly(sodium 4-styrenesulfonate)), PVP (poly(N-vinylpyrrolidone)), PDADMAC (poly(diallyldimethylammonium chloride)), PAA (polyacrylic acid) and PAH (polyallylamine hydrochloride), although not being necessarily limited thereto. Specifically, it may be PSS.

In the ligand having two functional groups, the two functional groups may be a thiol group (—SH) or an amine group (—NH$_2$), although not being necessarily limited thereto.

The small-molecule ligand having two functional groups may be at least one selected from a group consisting of ATP (4-aminothiophenol), BDT (1,4-benzenedithiol), MBA (4-mercaptobenzoic acid) and MBIA (2-mercaptobenzoimidazole-5-carboxylic acid), although not being necessarily limited thereto. Specifically, it may be ATP.

The positively charged metal nanoparticle core may be a metal nanoparticle capped with a positively charged material, although not being necessarily limited thereto. Specifically, the positively charged material may be cetyltrimethylammonium bromide (CTAB).

The negatively charged metal nanoparticle core may be a metal nanoparticle capped with a negatively charged material, although not being necessarily limited thereto. Specifically, the negatively charged material may be citrate.

In the core-satellite bimetal nanoparticle part, the metal of the core metal nanoparticle and the satellite may respectively be selected from a group consisting of silver, gold, copper and a mixture thereof. However, any metal widely used in the art may be used without limitation.

The core metal and the satellite metal may be not identical.

The conductive polymer may be at least one selected from a group consisting of polypyrrole, polythiophene, poly(3,4-ethylenedioxythiophene) (PEDOT) and polyaniline, although not being necessarily limited thereto. Specifically, it may be polyaniline.

The metal nanoparticle of the metal nanoparticle core is a metal nanorod or a metal nanosphere. However, any metal nanoparticle widely used in the art may be used without limitation.

The core-satellite bimetal nanoparticle part may further contain a Raman dye.

The Raman dye refers to a Raman-active organic compound and any one widely used in the art may be used without limitation. Specific examples may be selectedfrom a group consisting of MGITC (malachite green isothiocyanate), RBITC (rhodamine B isothiocyanate), rhodamine 6G, adenine, 4-aminopyrazolo(3,4-d)pyrimidine, 2-fluoroadenine, N6-benzoyladenine, kinetin, dimethylallylaminoadenine, zeatin, bromoadenine, 8-azaadenine, 8-azaguanine, 4-mercaptopyridine, 6-mercaptopurine, 4-amino-6-mercaptopyrazolo(3,4-d)pyrimidine, 8-mercaptoadenine, 9-aminoacridine and a mixture thereof, although not being necessarily limited thereto.

In the present disclosure, the "Janus nanostructure" refers to a nanostructure consisting of two different parts (a core-satellite bimetal nanoparticle part and a conductive polymer part).

In the present disclosure, the bimetal nanoparticle refers to a nanoparticle having a metal core-metal satellite structure. The metal core-metal satellite structure is named so after a planet and a satellite orbiting the planet. In the present disclosure, the core-satellite structure is a structure wherein the satellite metal is stuck around the metal core.

The bimetal nanoparticle part consists of a metal nanoparticle core onto which a ligand is adsorbed and a metal satellite reduced at the ligand-adsorbed site of the core. It refers to an asymmetrical Janus nanostructure formed as the conductive polymer part adheres to and grows (i.e., is eccentrically deposited) on only one side of the bimetal nanoparticle part.

In the present disclosure, the "Janus nanostructure" is also called a "Janus nanoparticle", a Janus nanoprobe, an anisotropic Janus nanostructure or an asymmetric nanostructure because it contains the core-satellite bimetal nanoparticle part and the conductive polymer part.

In another aspect, the present disclosure provides a metal nanoprobe for detecting a target material based on surface-enhanced Raman scattering (SERS) using the Janus nanostructure according to the present disclosure.

The Janus nanostructure according to the present disclosure may be provided as a metal nanoprobe for detecting a target material based on surface-enhanced Raman scattering by containing a Raman dye.

In the present disclosure, the probe refers to a material which is capable of specifically binding to a target material to be detected and allows identification of the presence of the target material through the binding.

In the present disclosure, the nanoprobe refers to a nano-sized probe.

The term "nano" includes the size range understood by those of ordinary skill in the art. The size range may be specifically 0.1-1000 nm, more specifically 10-1000 nm, more specifically 20-500 nm, further more specifically 40-250 nm.

The present disclosure provides a method for preparing a Janus nanostructure, including:
  i) a step of preparing a positively or negatively charged core metal nanoparticle;
  ii) a step of adsorbing a negatively charged ligand or a ligand having two functional groups to the core metal nanoparticle;
  iii) a step of adding the ligand-adsorbed core metal nanoparticle to an aqueous solution in which a conductive polymer monomer and a surfactant are dissolved;
  iv) a step of conducting an oxidation-reduction reaction between a metal ion and the conductive polymer monomer by adding a metal ion solution to the solution to which the core metal nanoparticle is added in the step iii); and
  v) a step of forming a Janus nanoparticle by forming a core-satellite bimetal nanoparticle part as the metal ion is reduced by receiving an electron donated by the conductive polymer at the ligand-adsorbed site of the core metal nanoparticle and forms a satellite metal and forming a conductive polymer part asymmetrically as the conductive polymer monomer is oxidized, is deposited on only one side of the bimetal nanoparticle part and grows into a conductive polymer.

In the positively or negatively charged core metal nanoparticle of the step i), the positively charged core metal nanoparticle may be a metal nanoparticle capped with a positively charged material. Specifically, the positively charged material may be cetyltrimethylammonium bromide (CTAB), although not being necessarily limited thereto.

The negatively charged core metal nanoparticle may be a metal nanoparticle capped with a negatively charged material. Specifically, the negatively charged material may be citrate, although not being necessarily limited thereto.

In the negatively charged ligand or the ligand having two functional groups of the step ii), the negatively charged ligand may be a polymeric ligand containing a charged repeating unit and the ligand having two functional groups may be a small-molecule ligand.

Specifically, the polymeric ligand containing a charged repeating unit may be at least one selected from a group consisting of PSS (poly(sodium 4-styrenesulfonate)), PVP (poly(N-vinylpyrrolidone)), PDADMAC (poly(diallyldimethylammonium chloride)), PAA (polyacrylic acid) and PAH (polyallylamine hydrochloride), although not being necessarily limited thereto. Specifically, it may be PSS.

The small-molecule ligand having two functional groups may be at least one selected from a group consisting of ATP (4-aminothiophenol), BDT (1,4-benzenedithiol), MBA (4-mercaptobenzoic acid) and MBIA (2-mercaptobenzoimidazole-5-carboxylic acid), although not being necessarily limited thereto. Specifically, it may be ATP.

In the core-satellite bimetal nanoparticle part of the step v), the metal of the core metal nanoparticle and the satellite may respectively be selected from a group consisting of silver, gold, copper and a mixture thereof. However, any metal widely used in the art may be used without limitation.

The metal ion in the step iv) may be selected from a group consisting of gold ion, silver ion, copper ion and a mixture thereof.

Specifically, the gold ion may be selected from a group consisting of gold(III) chloride hydrate, chlorocarbonylgold, hydrogen tetrachloroaurate, hydrogen tetrachloroaurate hydrate, chlorotriethylphosphinegold, chlorotrimethylphosphinegold, dimethyl(acetylacetonate)gold, gold(I) chloride, gold cyanide, gold sulfide and a mixture thereof, although not being necessarily limited thereto. Specifically, it may be gold(III) chloride hydrate.

The silver ion may be selected from a group consisting of silver nitrate ($AgNO_3$), silver tetrafluoroborate ($AgBF_4$), silver trifluoromethanesulfonate ($AgCF_3SO_3$), silver perchlorate ($AgClO_4$), silver acetate ($Ag(CH_3COO)$), silver hexafluorophosphate ($AgPF_6$), $Ag(CF_3COO)$ and a mixture thereof, although not being necessarily limited thereto. Specifically, it may be silver nitrate.

The copper ion may be selected from a group consisting of copper(II) acetylacetonate ($Cu(acac)_2$), copper(I) chloride (CuCl), copper(II) chloride ($CuCl_2$), copper(II) hexafluoroacetylacetonate ($Cu(hfac)_2$), copper(II) trifluoroacetyl chloride (Cu(tfac)2), copper(II) dipivaloylmethanate (Cu(dpm)$_2$), copper(II) pentafluorodimethylheptanedione (Cu(ppm)$_2$), copper(II) heptafluorodimethyloctane (Cu(fod)$_2$), copper(II) iminopentanone (Cu(acim)$_2$), copper(II) hexafluoro[(trifluoroethyl)imino]pentanone (Cu(nona-F)$_2$), copper(II) acetylacetoethylenediamine (Cu(acen)$_2$), copper nitrate (Cu(NO$_3$)$_2$), copper sulfate (CuSO$_4$) and a mixture thereof, although not being necessarily limited thereto.

The core metal and the satellite metal may be not identical.

The conductive polymer in the step iii) may be at least one selected from a group consisting of polypyrrole, polythiophene, poly(3,4-ethylenedioxythiophene) (PEDOT) and polyaniline, although not being necessarily limited thereto. Specifically, it may be polyaniline.

The metal nanoparticle of the core metal nanoparticle in the step i) may be a metal nanorod or a metal nanosphere. However, any metal nanoparticle widely used in the art may be used without limitation.

The growth into the conductive polymer in the step v) may be achieved by surface-templated polymerization.

The "surface-templated polymerization" refers to a polymerization method based on an oxidation-reduction reaction whereby the conductive polymer polyaniline is deposited on the bimetal nanoparticle through a spontaneous oxidation-reduction reaction between silver nitrate and an aniline monomer. Specifically, the polyaniline is deposited on the bimetal nanoparticle through oxidation polymerization of the conductive polymer monomer as the aniline monomer having a primary amine group donates an electron to the silver nitrate and the silver ion receives the electron to balance the oxidation-reduction reaction.

The method may further include, after the step v), a step of attaching a Raman dye on the bimetal nanoparticle surface of the Janus nanoparticle.

The surfactant of the step iii) may be at least one selected from a group consisting of sodium dodecyl sulfate (SDS), sodium deoxycholate and Triton X-200, although not being necessarily limited thereto. Specifically, it may be SDS.

The preparation of the Janus nanostructure consisting of the core-satellite bimetal nanoparticle part and the polymer part according to the present disclosure and its application for SERS-based biosensing are shown in FIGS. 10A-10D. FIGS. 10A-10D describes a method for preparing a Janus nanostructure consisting of a bimetal Au core-Ag satellite nanoparticle part and a polymer part through ligand-mediated interface control and a spontaneous oxidation-reduction reaction (a, b). As can be seen from FIG. 10A, for the synthesis of the bimetal AuNR core-Ag satellite nanoparticle part, the surface of AuNR is functionalized by coating CTAB-capped AuNR with the negatively charged polymer electrolyte PSS. The negatively charged polymer electrolyte PSS, which is also a polymeric ligand, is adsorbed onto the positively charged CTAB-capped AuNR through electrostatic interaction. The PSS with a molecular weight of 70,000 g/mol at a specific concentration is added to the AuNR solution in the presence of NaCl. A flexible polymer having a long chain length as compared to the size of the metal nanoparticle allows the electrically charged polymer to be coated on the oppositely charged MNP. And, NaCl is used to provide high charge to the polymer because the salt concentration affects the electrostatic interaction between the electrically charged polymer and the metal nanoparticle. This ensures effective coating of the oppositely charged metal nanoparticle. A high salt concentration can induce uncontrolled aggregation of the metal nanoparticle due to increased ionic strength. In addition, for the preparation of a stable polymer-metal nanoparticle composite, the concentration range of the polymer should be adequate for preventing the precipitation of the metal nanoparticle. The Janus structure having the bimetal nanoparticle part and the polymer part is prepared through an oxidation-reduction reaction between an aniline monomer and silver nitrate in the presence of the surfactant SDS. Specifically, after adding polymer-coated AuNR to an aniline solution, SDS and silver nitrate are added to initiate the oxidation polymerization of the aniline monomer and further reduction of silver ion. Interestingly, silver ion is reduced on the surface modified by the ligand of the gold nanorod particles (AuNPs) and a large number of silver nanoparticles (AgNPs) are used as satellite particles on the polymer-coated AuNR.

It is though that the Ag$^+$ ion is adsorbed first on the polymer-coated AuNR through electrostatic interaction between the positively charged silver ion and the negatively charged sulfonate group on the core surface and then AgNPs are heterogeneously deposited as satellite particles. The oxidation polymerization of aniline is initiated by the silver ion and the poly(aniline) part is formed on only one side of the bimetal core-satellite nanoparticle in the presence of SDS. The compartmentalization of the Janus nanostructure having the bimetal core-satellite nanoparticle part and the polymer part is achieved by balanced total surface energy, because SDS can affect the interfacial tension between the two adjacent poly(aniline)-water and poly(aniline)-metal nanoparticle phases. When a negatively charged molecule, sodium citrate, was introduced as a small ligand as a control experiment to further investigate the ligand-mediated surface functionalization, the core-satellite nanostructure was not observed. Because the CTAB is closely packed along the horizontal axis of AuNR, the citrate ion is located between AuNRs and the AuNRs are arranged side by side through electrostatic interaction between the bilayer of the CTAB and the citrate ion. It is because it is difficult to functionalize the whole surface of AuNR with the small ligand instead of the CTAB coating.

Meanwhile, the Janus nanostructure having the AuNP (AuNS) core-Ag satellite bimetal nanoparticle part and the polymer part is synthesized by small ligand-mediated surface control and an oxidation-reduction reaction as shown in FIG. 10B. Specifically, in order to prepare the bimetal AuNP core-Ag satellite nanoparticle part, citrate-capped AuNP is functionalized with a small-molecule ligand. The small-molecule ligand ATP containing a thiol group and an amine group distributed along the diameter direction is introduced into the citrate-capped AuNP (AuNS). The Janus nanostructure having the anisotropic polymer part is prepared after the oxidation of the aniline monomer and the reduction of the silver ion. The ligand density on the AuNP (AuNS) determines the degree of Ag ion coordination and Ag reduction. The small-molecule ligand is used to control the interfacial tension between two metal nanoparticle layers during the growth of the metal nanoparticle. The ligand buried in the interface between Au and Ag is a major factor in binding of a second metal. When the positively charged polymer electrolyte poly(dimethylaminoethyl methacrylate) was introduced to the AuNP solution as a polymer ligand, as a control experiment, a stable ligand-coated metal nanoparticle was not formed but a large metal nanoparticle aggregate was formed instead due to the electrostatic interaction between the citrate-capped AuNP and the positively charged polymer ligand. Because AuNP is weakly capped with the citrate ion, AuNP is easily aggregated upon addition of a heterogeneous material. In this regard, the small ligand ATP is selected with a concentration enough to main the colloidal stability of AuNP. FIG. 10C describes the spontaneous oxidation-reduction reaction between the aniline monomer and silver nitrate. The aniline monomer is oxidized to poly(aniline) by donating an electron to the silver nitrate whereas the silver ion is reduced by accepting the electron.

As can be seen from FIG. 10D, the Janus nanostructure consisting of the core-satellite bimetal nanoparticle part and the polymer part can be used as a SERS nanoprobe for biosensing. The polymer part provides an antibody-binding site for detection of a target and the bimetal particle part is functionalized with a Raman dye for SERS. In the presence of a target, a sandwich immune complex consisting of the SERS nanoprobe, the target and a magnetic bead is formed and quantitative and qualitative SERS-based biosensing is possible based on Raman shift.

The present disclosure provides a method for detecting a target material based on surface-enhanced Raman scattering (SERS), including:
 a) a step of preparing a sample solution containing a target material to be detected;
 b) a step of immobilizing a first antibody for the target material onto a magnetic nanoparticle;
 c) a step of immobilizing a second antibody for the target material onto the metal nanoprobe;
 d) a step of forming an immune complex wherein the target material and the first antibody of the magnetic nanoparticle are conjugated by adding the first antibody-immobilized magnetic nanoparticle to the sample solution;
 e) a step of forming a sandwich immune complex of the second antibody of the metal nanoprobe, the target material and the first antibody of the magnetic nanoparticle by adding the second antibody-immobilized metal nanoprobe to the solution containing the first antibody-conjugated immune complex;
 f) a step of separating the magnetic nanoparticle and the metal nanoprobe not forming the sandwich immune complex using a magnetic field; and
 g) a step of measuring a Raman signal of the sandwich immune complex.

In the present disclosure, the "sandwich immune complex" refers to an immune complex wherein an antibody, an antigen and an antibody are bound with a sandwich shape in which the antigen is inserted between the antibodies.

The target material may be a protein or a pathogen.

The protein may be selected from a group consisting of an antigen, a biological aptamer, a receptor, an enzyme and a ligand.

In the Janus nanostructure containing the bimetal Au core-Ag satellite nanoparticle part and the polymer part according to the present disclosure, the bimetal nanoparticle part modified with the charged polymer or ligand is formed by functionalizing the surface of AuNR by coating CTAB-capped AuNR with the negatively charged polymer electrolyte PSS and functionalizing citrate-capped AuNP with the small-molecule ligand. Because a nanogap is formed only on the surface-modified site as the silver ion is reduced, Raman intensity is greatly improved. Accordingly, the Janus nanostructure of the present disclosure can be used as a metal nanoprobe for detecting a target material based on surface-enhanced Raman scattering (SERS).

Invention 3:

The present disclosure provides an asymmetric Janus nanoprobe for detecting a target material based on surface-enhanced Raman scattering (SERS), containing:
 a bimetal nanocluster part having a core-shell structure and containing a Raman dye; and
 a conductive polymer part,
 wherein the nanoprobe has an asymmetric structure as the conductive polymer part is oxidized on only one side of the bimetal nanocluster part.

In the present disclosure, the probe refers to a material which is capable of specifically binding to a target material to be detected and allows identification of the presence of the target material through the binding.

In the present disclosure, the nanoprobe refers to a nano-sized probe.

The term "nano" includes the size range understood by those of ordinary skill in the art. The size range may be specifically 0.1-1000 nm, more specifically 10-1000 nm, more specifically 20-500 nm, further more specifically 40-250 nm.

In the present disclosure, the Raman dye refers to a Raman-active organic compound and any one widely used in the art may be used without limitation. Specific examples may be selected from a group consisting of MGITC (malachite green isothiocyanate), RBITC (rhodamine B isothiocyanate), rhodamine 6G, adenine, 4-aminopyrazolo(3,4-d)pyrimidine, 2-fluoroadenine, N6-benzoyladenine, kinetin, dimethylallylaminoadenine, zeatin, bromoadenine, 8-azaadenine, 8-azaguanine, 4-mercaptopyridine, 6-mercaptopurine, 4-amino-6-mercaptopyrazolo(3,4-d)pyrimidine, 8-mercaptoadenine, 9-aminoacridine and a mixture thereof, although not being necessarily limited thereto.

The bimetal nanocluster part may be a bimetal nanocluster containing: a core selected from a group consisting of gold, silver, copper and a mixture thereof; and a shell selected from a group consisting of gold, silver, copper and a mixture thereof.

The core metal and the shell metal may be identical or different.

The conductive polymer may be at least one selected from a group consisting of polypyrrole, polythiophene, poly(3,4-ethylenedioxythiophene) (PEDOT) and polyaniline, although not being necessarily limited thereto. Specifically, it may be polyaniline.

In the present disclosure, the "asymmetric Janus nanoprobe" refers to a nanoprobe consisting of two different parts (a bimetal nanocluster part having a core-shell structure and containing a Raman dye and a conductive polymer part), which has an asymmetric structure formed as the conductive polymer part is oxidized and grows (i.e., is eccentrically deposited) on only one side of the bimetal nanoparticle part. In the present disclosure, the "asymmetric Janus nanoprobe", which contains a bimetal nanocluster part and a conductive polymer part, is also called an "asymmetric Janus nanocluster-polymer nanoparticle", an asymmetric nanoprobe, an anisotropic Janus nanostructure or an asymmetric nanostructure.

In the present disclosure, the bimetal refers to two metals having a metal core-metal shell structure.

In the present disclosure, the metal nanocluster refers to an aggregate formed from aggregation of metal nanoparticles. It is a term widely used in the art.

In the present disclosure, the bimetal nanocluster refers to an aggregate forming a core-shell structure as a different metal ion is reduced on a core metal nanocluster.

The anisotropic Janus nanostructure consisting of the core-shell bimetal nanocluster part and the conductive polymer part according to the present disclosure can significantly improve SERS characteristics due to interparticle coupling between the core-shell nanoparticles in the bimetal nanocluster. In addition, the responsiveness can be improved by attaching an antibody for the target to be detected to the polymer part. Accordingly, the asymmetric Janus nanoprobe according to the present disclosure can be used as a nanoprobe for detection of a target material based on SERS.

In another aspect, the present disclosure provides a method for preparing an asymmetric Janus nanoprobe for detecting a target material based on surface-enhanced Raman scattering (SERS), including:
i) a step of forming a core metal nanoparticle cluster having a Raman dye by mixing a metal nanoparticle forming a core and a Raman dye and heating or aggregating the same;
ii) a step of adding the core metal nanoparticle cluster to an aqueous solution in which a conductive polymer monomer and a surfactant are dissolved;
iii) a step of conducting an oxidation-reduction reaction between a metal ion and the conductive polymer monomer by adding a metal ion solution to the solution to which the core metal nanoparticle cluster is added in ii); and
iv) a step of forming a core-shell bimetal nanoparticle cluster part as the metal ion is reduced by receiving an electron donated by the conductive polymer and is deposited on the surface of the core metal nanoparticle and forming a conductive polymer part asymmetrically as the conductive polymer monomer is oxidized, is deposited on only one side of the bimetal nanocluster part and grows into a conductive polymer.

The method may further include, after the step i), a step of stabilizing the core metal nanocluster with a protein.

The protein may be selected from a group consisting of avidin, streptavidin, BSA (bovine serum albumin), insulin, soy protein, casein, gelatin and a mixture thereof, although not being necessarily limited thereto. Specifically, it may be BSA.

The core metal of the step i) may be selected from a group consisting of gold, silver, copper and a mixture thereof. However, any metal widely used in the art may be used without limitation.

Specifically, the core metal may be selected from a group consisting of gold, silver, copper and a mixture thereof.

The metal ion of the step iii) may be selected from a group consisting of gold ion, silver ion, copper ion and a mixture thereof, although not being necessarily limited thereto.

Specifically, the gold ion may be selected from a group consisting of gold(III) chloride hydrate, chlorocarbonylgold, hydrogen tetrachloroaurate, hydrogen tetrachloroaurate hydrate, chlorotriethylphosphinegold, chlorotrimethylphosphinegold, dimethyl(acetylacetonate)gold, gold(I) chloride, gold cyanide, gold sulfide and a mixture thereof, although not being necessarily limited thereto. Specifically, it may be gold(III) chloride hydrate.

The silver ion may be selected from a group consisting of silver nitrate ($AgNO_3$), silver tetrafluoroborate ($AgBF_4$), silver trifluoromethanesulfonate ($AgCF_3SO_3$), silver perchlorate ($AgClO_4$), silver acetate ($Ag(CH_3COO)$), silver hexafluorophosphate ($AgPF_6$), $Ag(CF_3COO)$ and a mixture thereof, although not being necessarily limited thereto. Specifically, it may be silver nitrate.

The copper ion may be selected from a group consisting of copper(II) acetylacetonate ($Cu(acac)_2$), copper(I) chloride (CuCl), copper(II) chloride ($CuCl_2$), copper(II) hexafluoroacetylacetonate ($Cu(hfac)_2$), copper(II) trifluoroacetyl chloride ($Cu(tfac)_2$), copper(II) dipivaloylmethanate ($Cu(dpm)_2$), copper(II) pentafluorodimethylheptanedione ($Cu(ppm)_2$), copper(II) heptafluorodimethyloctane ($Cu(fod)_2$), copper(II) iminopentanone ($Cu(acim)_2$), copper(II) hexafluoro[(trifluoroethyl)imino]pentanone ($Cu(nona-F)_2$), copper(II) acetylacetoethylenediamine ($Cu(acen)_2$), copper nitrate ($Cu(NO_3)_2$), copper sulfate ($CuSO_4$) and a mixture thereof, although not being necessarily limited thereto.

The conductive polymer in the step ii) may be at least one selected from a group consisting of polypyrrole, polythiophene, poly(3,4-ethylenedioxythiophene) (PEDOT) and polyaniline, although not being necessarily limited thereto. Specifically, it may be polyaniline.

The method may further include, after the oxidation-reduction reaction of the step iii), a step of incubating the reaction solution with a surfactant solution.

The surfactant may be at least one selected from a group consisting of sodium dodecyl sulfate (SDS), sodium deoxycholate and Triton X-200, although not being necessarily limited thereto. Specifically, it may be SDS.

The growth into the conductive polymer in the step iv) may be achieved by surface-templated polymerization.

The "surface-templated polymerization" refers to a polymerization method based on an oxidation-reduction reaction whereby the conductive polymer polyaniline is deposited on the bimetal nanocluster through a spontaneous oxidation-reduction reaction between silver nitrate and an aniline monomer. Specifically, the polyaniline is deposited on the bimetal nanocluster through oxidation polymerization of the conductive polymer monomer as the aniline monomer having a primary amine group donates an electron to the silver nitrate and the silver ion receives the electron to balance the oxidation-reduction reaction.

The synthesis of the asymmetric Janus nanocluster-polymer nanoparticle according to the present disclosure and its SERS-based application are schematically shown in FIGS. 16A-16C. FIG. 16A shows a method for preparing the SERS nanoprobe based on an oxidation-reduction reaction. Firstly, a gold nanoparticle (AuNP) cluster is formed by aggregating AuNP in the presence of a Raman dye and it is stabilized by BSA coating. Specifically, citrate-capped AuNP is mixed with a Raman dye, MGITC or RBITC, at a final concentration of 1.5 μM or 3.8 μM, respectively. Also, silver nitrate and sodium citrate is added to an AuNP colloid solution and incubated at 95° C. for 10-60 minutes. When silver ion is reduced to Au, Au nanoparticle grows and is aggregated as the Raman dye is adsorbed onto the surface. If the isothiocyanate group (—N═C═S) of MGITC or RBITC is strongly attached to the AuNP surface, the AuNP cluster is formed due to the electrostatic interaction between the negatively charged particle and the positively charged Raman dye-labeled particle. The Au nanocluster containing the Raman dye is stabilized by BSA to prevent further aggregation. Secondly, an asymmetric bimetal nanocluster-polymer nanostructure is prepared through an oxidation-reduction reaction between silver nitrate and an aniline monomer. The concentrated AuNP cluster is added to a solution containing an aniline monomer and the surfactant SDS. After mixing, silver nitrate is added to the solution to initiate oxidation polymerization into poly(aniline) by decreasing the silver ion in the AuNP cluster and forming the bimetal Au (core)-Ag (shell) nanocluster. In the presence of SDS, the bimetal nanocluster and the poly(aniline) part are formed anisotropically (asymmetrically) to balance the interfacial tension between the poly(aniline), bimetal nanocluster and water phases by minimizing surface area. FIG. 16B shows the spontaneous oxidation-reduction reaction between the two precursors. The aniline monomer having a primary amine group donates an electron to the silver nitrate and the silver ion accepts the electron to balance the oxidation-reduction reaction. FIG. 16C shows an SERS-based biosensing method using the asymmetric Janus nanocluster-polymer nanoprobe. Specifically, the polymer part is selectively functionalized to introduce an antibody. In the presence of a target molecule, the SERS nanoprobe to which the target-specific antibody is bound and the magnetic bead capture the target and a sandwich immune complex consisting of the SERS nanoprobe, the target and the magnetic bead is formed. The complex is washed by applying a magnetic field and the Raman shift is measured as a function of the target concentration.

In another aspect, the present disclosure provides a method for detecting a target material based on surface-enhanced Raman scattering (SERS), including:
a) preparing a sample solution containing a target material to be detected;
b) immobilizing a first antibody for the target material onto a magnetic nanoparticle;
c) immobilizing a second antibody for the target material onto the metal nanoprobe;
d) forming an immune complex wherein the target material and the first antibody of the magnetic nanoparticle are conjugated by adding the first antibody-immobilized magnetic nanoparticle to the sample solution;
e) forming a sandwich immune complex of the second antibody of the metal nanoprobe, the target material and the first antibody of the magnetic nanoparticle by adding the second antibody-immobilized metal nanoprobe to the solution containing the first antibody-conjugated immune complex;
f) separating the magnetic nanoparticle and the metal nanoprobe not forming the sandwich immune complex using a magnetic field; and
g) measuring a Raman signal of the sandwich immune complex.

The target material may be a protein or a pathogen.

The protein may be selected from a group consisting of an antigen, a biological aptamer, a receptor and an enzyme.

In the present disclosure, the "sandwich immune complex" refers to an immune complex wherein an antibody, an antigen and an antibody are bound with a sandwich shape in which the antigen is inserted between the antibodies.

Invention 4:

The present disclosure provides an anisotropic Janus nanostructure consisting of:
a bimetal nanorod cluster part containing a metal nanorod cluster seed having directionality and a metal shell; and
a conductive polymer part.

In the seed-shell bimetal nanorod cluster part, the metal nanorod cluster seed and the metal shell may respectively be selected from a group consisting of silver, gold, copper and a mixture thereof. However, any metal widely used in the art may be used without limitation.

The metal nanorod cluster seed having directionality may be formed as the sides of individual metal nanorod particles are arranged side by side (side-by-side assembly) or the ends of individual metal nanorod particles are connected end to end (end-to-end assembly).

In the present disclosure, the "sides of metal nanorod particles" refers to the two long sides of metal nanorods which have a narrow and long shape.

In the present disclosure, "individual metal nanorod particles are arranged side by side (side-by-side assembly)" refers to a state wherein the two long sides of metal nanorods which have a narrow and long shape are arranged continuously while contacting each other.

In the present disclosure, the "ends of individual metal nanorod particles" refers to the two short sides of metal nanorods which have a narrow and long shape.

In the present disclosure, "individual metal nanorod particles are connected end to end (end-to-end assembly)" refers to a state wherein the two short sides of metal nanorods which have a narrow and long shape are arranged continuously while contacting diagonally each other.

The conductive polymer may be at least one selected from a group consisting of polypyrrole, polythiophene, poly(3,4-ethylenedioxythiophene) (PEDOT) and polyaniline, although not being necessarily limited thereto. Specifically, it may be polyaniline.

The bimetal nanorod cluster part may further contain a Raman dye.

The Raman dye refers to a Raman-active organic compound and any one widely used in the art may be used without limitation. Specific examples may be selected from a group consisting of MGITC (malachite green isothiocyanate), RBITC (rhodamine B isothiocyanate), rhodamine 6G, adenine, 4-aminopyrazolo(3,4-d)pyrimidine, 2-fluoroadenine, N6-benzoyladenine, kinetin, dimethylallylaminoadenine, zeatin, bromoadenine, 8-azaadenine, 8-azaguanine, 4-mercaptopyridine, 6-mercaptopurine, 4-amino-6-mercaptopyrazolo(3,4-d)pyrimidine, 8-mercaptoadenine, 9-aminoacridine and a mixture thereof, although not being necessarily limited thereto.

In the present disclosure, the "anisotropic Janus nanostructure" refers to a nanostructure consisting of two distinct, asymmetric different parts (a bimetal nanorod cluster part having a seed-shell structure and a conductive polymer part). In the present disclosure, the bimetal nanorod cluster part refers to a metal nanorod cluster seed having directionality and formed of a metal shell which forms an asymmetrical Janus nanostructure as the conductive polymer part adheres to and grows (i.e., is eccentrically deposited) on only one side of the bimetal nanorod cluster part.

In the present disclosure, the "anisotropic Janus nanostructure" is also called a "bimetal-polymer Janus nanoparticle", a "Janus nanoparticle" or a Janus nanoprobe.

In the present disclosure, the bimetal refers to two metals having a metal seed-metal shell structure.

In the present disclosure, the metal nanorod cluster refers to an aggregate formed from aggregation of metal nanorods. It is a term widely used in the art.

In the present disclosure, the bimetal nanorod cluster refers to an aggregate of bimetal nanorods having a seed-shell structure.

The present disclosure provides a metal nanoprobe for measuring a surface-enhanced Raman scattering (SERS) signal using the anisotropic Janus nanostructure according to the present disclosure.

The Janus nanostructure according to the present disclosure may be provided as a metal nanoprobe for measuring a surface-enhanced Raman scattering signal by containing a Raman dye.

In the present disclosure, the probe refers to a material which is capable of specifically binding to a target material to be detected and allows identification of the presence of the target material through the binding.

In the present disclosure, the nanoprobe refers to a nano-sized probe.

The term "nano" includes the size range understood by those of ordinary skill in the art. The size range may be specifically 0.1-1000 nm, more specifically 10-1000 nm, more specifically 20-500 nm, further more specifically 40-250 nm.

The present disclosure provides a method for preparing an anisotropic Janus nanostructure, including:
  i) a step of forming a metal nanorod cluster seed having directionality by mixing a metal nanorod particle forming a seed and an organic anion or a negatively charged stimulation-responsive copolymer having a terminal thiol group;
  ii) a step of adding the metal nanorod cluster seed to an aqueous solution in which a conductive polymer monomer and a surfactant are dissolved;
  iii) a step of conducting an oxidation-reduction reaction between a metal ion and the conductive polymer monomer by adding a metal ion solution to the solution to which the metal nanorod cluster seed is added in the step ii); and
  iv) a step of forming a seed-shell bimetal nanorod cluster part as the metal ion is reduced by receiving an electron donated by the conductive polymer and is deposited on the surface of the seed metal nanorod particle and forming a conductive polymer part asymmetrically as the conductive polymer monomer is oxidized, is deposited on only one side of the bimetal nanorod cluster part and grows into a conductive polymer.

The method may further include, after the step i), a step of attaching a Raman dye on the surface of the metal nanorod cluster seed.

The seed metal of the step i) may be selected from a group consisting of gold, silver, copper and a mixture thereof. However, any metal widely used in the art may be used without limitation.

The metal ion of the step iii) may be selected from a group consisting of gold ion, silver ion, copper ion and a mixture thereof.

Specifically, the gold ion may be selected from a group consisting of gold(III) chloride hydrate, chlorocarbonylgold, hydrogen tetrachloroaurate, hydrogen tetrachloroaurate hydrate, chlorotriethylphosphinegold, chlorotrimethylphosphinegold, dimethyl(acetylacetonate)gold, gold(I) chloride, gold cyanide, gold sulfide and a mixture thereof, although not being necessarily limited thereto. Specifically, it may be gold(III) chloride hydrate.

The silver ion may be selected from a group consisting of silver nitrate ($AgNO_3$), silver tetrafluoroborate ($AgBF_4$), silver trifluoromethanesulfonate ($AgCF_3SO_3$), silver perchlorate ($AgClO_4$), silver acetate ($Ag(CH_3COO)$), silver hexafluorophosphate ($AgPF_6$), $Ag(CF_3COO)$ and a mixture thereof, although not being necessarily limited thereto. Specifically, it may be silver nitrate.

The copper ion may be selected from a group consisting of copper(II) acetylacetonate ($Cu(acac)_2$), copper(I) chloride (CuCl), copper(II) chloride ($CuCl_2$), copper(II) hexafluoroacetylacetonate ($Cu(hfac)_2$), copper(II) trifluoroacetyl chloride ($Cu(tfac)_2$), copper(II) dipivaloylmethanate ($Cu(dpm)_2$), copper(II) pentafluorodimethylheptanedione ($Cu(ppm)_2$), copper(II) heptafluorodimethyloctane ($Cu(fod)_2$), copper(II) iminopentanone ($Cu(acim)_2$), copper(II) hexafluoro[(trifluoroethyl)imino]pentanone ($Cu(nona-F)_2$), copper(II) acetylacetoethylenediamine ($Cu(acen)_2$), copper nitrate ($Cu(NO_3)_2$), copper sulfate ($CuSO_4$) and a mixture thereof, although not being necessarily limited thereto.

The metal nanorod cluster seed having directionality of the step i) may be formed as the sides of individual metal nanorod particles are arranged side by side (side-by-side assembly) or the ends of individual metal nanorod particles are connected end to end (end-to-end assembly).

The metal nanorod cluster seed formed as the sides of individual metal nanorod particles are arranged side by side (side-by-side assembly) may be prepared by:
  a step of preparing a metal nanorod particle with a positively charged surfactant present on the surface using a metal seed;
  a step of adding a Raman dye to a solution containing the metal nanorod;
  a step of adding an organic anion to the metal nanorod solution containing the Raman dye; and
  a step of forming a metal nanorod cluster seed as the sides of individual metal nanorod particles are arranged side by side with respect to the sides of other individual metal nanorod particles through electrostatic attraction between the positively charged surfactant attached to the side of the metal nanorod and the organic anion.

Specifically, the "formation of a metal nanorod cluster seed as the sides of individual metal nanorod particles are arranged side by side with respect to the sides of other individual metal nanorod particles through electrostatic attraction between the positively charged surfactant attached to the side of the metal nanorod and the organic anion" means that the sides of individual metal nanorod particles are arranged side by side with respect to the sides of other individual metal nanorod particles through electrostatic attraction between the positively charged surfactant attached to the side of the metal nanorod and the organic anion as the bonding of 'the positively charged surfactant attached to the side of a first metal nanorod—the organic anion—the positively charged surfactant attached to the side of a second metal nanorod' is formed continuously. Because this assembly occurs spontaneously through the electrostatic attraction, it is named "self-assembly" in the present disclosure.

In an exemplary embodiment of the present disclosure, a side-by-side self-assembled gold nanorod (AuNR) cluster is induced through electrostatic attraction between a CTAB bilayer and citrate.

The positively charged surfactant may be selected from a group consisting of CTAB (hexadecyltrimethylammonium bromide), DTAB (dodecyltrimethylammoniumbromide) and TTAB (trimethyltetradecylammoniumbromide), although not being necessarily limited thereto. Specifically, it may be CTAB.

The organic anion may be selected from a group consisting of citrate, malate, fumarate, tartrate, succinate, oxalate and gluconate, although not being necessarily limited thereto. Specifically, it may be citrate.

The metal nanorod cluster seed formed as the ends of individual metal nanorod particles are connected end to end (end-to-end assembly) may be prepared by:
  a step of preparing a metal nanorod particle with a positively charged surfactant present on the surface using a metal seed;
  a step of adding a negatively charged stimulation-responsive copolymer having a terminal thiol group to a solution containing the metal nanorod;
  a step of stirring the metal nanorod solution to which the negatively charged stimulation-responsive copolymer is added;
  a step of adding a Raman dye to the stirred solution; and
  a step of forming a metal-thiol group bonding as the positively charged surfactant at the end of the metal nanorod is bonded to the thiol group of the negatively charged stimulation-responsive copolymer and forming a metal nanorod cluster seed as the positively charged surfactant at the side of an individual metal nanorod particle is bonded to the negatively charged stimulation-responsive copolymer at the end of another individual metal nanorod particle through electrostatic attraction.

By "forming a metal-thiol group bonding as the positively charged surfactant at the end of the metal nanorod is bonded to the thiol group of the negatively charged stimulation-responsive copolymer", the positively charged surfactant at the end of the metal nanorod is exchanged with the negatively charged stimulation-responsive copolymer.

Specifically, the "formation of a metal nanorod cluster seed as the sides of individual metal nanorod particles are arranged side by side with respect to the sides of other individual metal nanorod particles through electrostatic attraction between the positively charged surfactant attached to the side of the metal nanorod and the organic anion" means that the ends (more specifically side—end) of individual metal nanorod particles are connected diagonally as the bonding of 'the positively charged surfactant at the side of a first metal nanorod—the negatively charged stimulation-responsive copolymer at the end of a second metal nanorod' is formed continuously through the electrostatic attraction between the positively charged surfactant and the negatively charged stimulation-responsive copolymer. Because this assembly occurs spontaneously through the electrostatic attraction, it is named "self-assembly" in the present disclosure.

In an exemplary embodiment of the present disclosure, a CTAB ligand attached to the end portion of surface-modified AuNR is exchanged with negatively charged poly(AAc-b-NIPAM)-SH through metal-thiol group bonding. As a result, an end-to-end self-assembled AuNR cluster is induced through the electrostatic attraction between the positively charged CTAB on the side of AuNR and poly(AAc-b-NIPAM) at the end of another AuNR.

The positively charged surfactant may be selected from a group consisting of CTAB (hexadecyltrimethylammonium bromide), DTAB (dodecyltrimethylammonium bromide) and TTAB (trimethyltetradecylammonium bromide), although not being necessarily limited thereto. Specifically, it may be CTAB.

In the present disclosure, the term "stimulation-responsive" refers to a change of behavior in response to stimulation (e.g., heat, etc.).

In the present disclosure, the "negatively charged stimulation-responsive copolymer" refers to a negatively charged copolymer exhibiting a change of behavior in response to stimulation.

The negatively charged stimulation-responsive copolymer may be a copolymer consisting of a negatively charged moiety and a stimulation-responsive polymer. The copolymerization of the negatively charged moiety and the stimulation-responsive polymer may be achieved by any copolymerization method known in the art. In an exemplary embodiment of the present disclosure, it is synthesized by sequential RAFT (reversible addition-fragmentation chain transfer) polymerization followed by aminolysis and hydrolysis.

In the present disclosure, the term "moiety" refers to a portion of a material (substance) exhibiting a certain property.

In the present disclosure, the "negatively charged moiety" refers to a material having a negative charge.

The negatively charged moiety may be selected from a group consisting of acrylic acid, methacrylic acid, itaconic acid, maleic acid and a mixture thereof, although not being necessarily limited thereto. Specifically, it may be acrylic acid.

In the present disclosure, the "stimulation-responsive polymer" refers to a polymer exhibiting a change of behavior in response to stimulation.

The stimulation-responsive polymer may be selected from a group consisting of poly(N-isopropylacrylamide) (polyNIPAM), poly(N,N'-diethylacrylamide) (polyDEAAm), poly(dimethylaminoethyl methacrylate) (polyDMAEMA), poly(N-(L)-(1-hydroxymethyl)propyl-methacrylamide), poly[oligo(ethylene glycol) methyl ether methacrylate] (POEGMA), poly(2-vinylpyridine) (P2VP), poly(4-vinylpyridine) (P4VP) and a mixture thereof, although not being necessarily limited thereto. Specifically, it may be poly(N-isopropylacrylamide).

Specifically, the negatively charged stimulation-responsive copolymer may be poly(AAc-b-NIPAM) (poly(acrylic acid-block-N-isopropylacrylamide)), although not being necessarily limited thereto. The poly(AAc-b-NIPAM) according to the present disclosure has a negative charge due to the acrylic acid. It is also referred to as "poly(AAc-b-NIPAM)-SH" in the present disclosure because it has a terminal thiol group (—SH).

The synthesis of the negatively charged stimulation-responsive copolymer poly(AAc-b-NIPAM) by sequential RAFT (reversible addition-fragmentation chain transfer) polymerization followed by aminolysis and hydrolysis according to the present disclosure is described in FIGS. 26A-26B. First, poly(tBA) (poly(tBA)-macro CDTPA) is synthesized by RAFT polymerization using tBA (tert-butyl acrylate) as a monomer, CDTPA as a CTA (chain transfer agent) and AIBN (azobisisobutyronitrile, 2,2'-azobis(2-methylpropionitrile)) as an initiator. Then, poly(tBA-b-NIPAM) is prepared by RAFT polymerization using NIPAM (N-isopropylacrylamide 97%) as a monomer, the synthesized poly(tBA)-macro CDTPA as a CTA and AIBN as an initiator. After forming thiol-terminated poly(tBA-b-NIPAM) by converting the thiol-thiocarbonylthio group in the prepared poly(tBA-b-NIPAM) to thiol through aminolysis (FIG. 26A), thiol-terminated poly(AAc-b-NIPAM) is prepared by converting the large hydrophobic terminal group of the poly(tBA) block in the formed thiol-terminated poly(tBA-b-NIPAM) to a carboxyl group through hydrolysis (FIG. 26B).

The prepared negatively charged stimulation-responsive copolymer, poly(AAc-b-NIPAM), is used to selectively modify the end portion of AuNR.

The conductive polymer may be at least one selected from a group consisting of polypyrrole, polythiophene, poly(3,4-ethylenedioxythiophene) (PEDOT) and polyaniline, although not being necessarily limited thereto. Specifically, it may be polyaniline.

The method may further include, after the oxidation-reduction reaction of the step iii), a step of incubating the reaction solution with a surfactant solution.

The surfactant in the step ii) or after the oxidation-reduction reaction of the step iii) may be at least one selected from a group consisting of sodium dodecyl sulfate (SDS), sodium deoxycholate and Triton X-200, although not being necessarily limited thereto. Specifically, it may be SDS.

The growth into the conductive polymer in the step iv) may be achieved by surface-templated polymerization.

The "surface-templated polymerization" refers to a polymerization method based on an oxidation-reduction reaction whereby the conductive polymer polyaniline is deposited on the bimetal nanocluster through a spontaneous oxidation-reduction reaction between silver nitrate and an aniline monomer. Specifically, the polyaniline is deposited on the bimetal nanocluster through oxidation polymerization of the conductive polymer monomer as the aniline monomer having a primary amine group donates an electron to the silver nitrate and the silver ion receives the electron to balance the oxidation-reduction reaction.

The side-by-side or end-to-end anisotropical self-assembly of AuNR and the synthesis of a Janus nanostructure are schematically shown in FIGS. 24A-24D. FIG. 24A shows the controlled assembly of AuNR through electrostatic interaction. The side-by-side assembly of AuNR is achieved by the addition of citrate anion. During the synthesis of AuNR, a CTAB surfactant is used to induce asymmetrical shape and maintain the colloidal stability of AuNR. As the citrate anion and the Raman dye MGITC is added to a concentrated AuNR solution, a side-by-side assembled AuNR cluster is induced through electrostatic attraction between the CTAB bilayer and the citrate. The MGITC is effectively embedded in the CTAB bilayer and located at the interparticle junction between adjacent AuNRs in the side-by-side assembled cluster. The side-by-side assembled AuNR cluster is stabilized by PSS coating. Meanwhile, the end-to-end assembly of AuNR is induced as follows. The CTAB ligand attached to the end portion of AuNR is exchanged with poly(AAc-b-NIPAM) through thiol group-metal bonding and the end-to-end self-assembly of AuNR is induced through electrostatic attraction between the positively charged CTAB on the side of AuNR and the exchanged poly(AAc-b-NIPAM) on the end portion. FIG. 24B shows the synthesis of an anisotropic bimetal nanorod cluster-polymer Janus nanostructure using an anisotropically self-assembled AuNR cluster as a seed. The Janus nanostructure is prepared through oxidation-reduction between silver nitrate and an aniline monomer. A poly(aniline) part is formed through surface-templated polymerization of the aniline monomer initiated by reducing the silver nitrate in the presence of the surfactant SDS. As a result, poly(aniline) is eccentrically deposited on the anisotropically assembled AuNR. The reaction is conducted for 24 hours without mechanical stirring and a bimetal Au core-Ag shell nanorod cluster part and a poly(aniline) part of the asymmetrical Janus nanostructure is prepared by further incubating overnight in an SDS solution. Upon addition of the SDS, the bimetal nanorod cluster part is partially captured by the poly(aniline) part. The surfactant SDS affects the balancing of the interfacial tension ($\sigma$) between the three bimetal, poly(aniline) and water phases, thereby determining the equilibrium state. That is to say, the SDS reduces the interfacial tension $\sigma_{poly(aniline)-water}$ and thereby achieves balanced interaction between the three phases ($\sigma_{Ag-poly(aniline)} > \sigma_{Ag-water} + \sigma_{poly(aniline)-water}$). FIG. 24C describes the oxidative coupling reaction between the aniline monomer and silver nitrate. The oxidation-reduction reaction involves electron transport from the aniline monomer to silver ion as it is oxidized to the poly(aniline). As seen from FIG. 24D, the Janus nanostructure according to the present disclosure can be used as a promising SERS nanoprobe for biosensing. The bimetal nanorod cluster part can exhibit high SERS efficiency, which derives from the hot spot junction between the interparticle gap of the anisotropically assembled AuNR nanocluster. The poly(aniline) part provides an antibody-binding site for detection of a target. In the presence of a target, a sandwich immune complex consisting of the SERS nanoprobe, the target and a magnetic bead is formed and both quantitative and qualitative SERS-based biosensing is achieved as functions of Raman shift.

The present disclosure provides a method for detecting a target material based on surface-enhanced Raman scattering (SERS), including:

a) a step of preparing a sample solution containing a target material to be detected;
b) a step of immobilizing a first antibody for the target material onto a magnetic nanoparticle;
c) a step of immobilizing a second antibody for the target material onto the metal nanoprobe;
d) a step of forming an immune complex wherein the target material and the first antibody of the magnetic nanoparticle are conjugated by adding the first antibody-immobilized magnetic nanoparticle to the sample solution;
e) a step of forming a sandwich immune complex of the second antibody of the metal nanoprobe, the target material and the first antibody of the magnetic nanoparticle by adding the second antibody-immobilized metal nanoprobe to the solution containing the first antibody-conjugated immune complex;
f) a step of separating the magnetic nanoparticle and the metal nanoprobe not forming the sandwich immune complex using a magnetic field; and
g) a step of measuring a Raman signal of the sandwich immune complex.

The target material may be a protein or a pathogen.

The protein may be selected from a group consisting of an antigen, a biological aptamer, a receptor, an enzyme and a ligand.

In the present disclosure, the "sandwich immune complex" refers to an immune complex wherein an antibody, an antigen and an antibody are bound with a sandwich shape in which the antigen is inserted between the antibodies.

The anisotropic bimetal nanorod cluster-polymer Janus nanostructure according to an exemplary embodiment of the present disclosure induces directional self-assembly using the electrostatic attraction between the CTAB-capped AuNR and the organic anion or the electrostatic attraction between the CTAB-capped AuNR and the negatively charged stimulation-responsive copolymer. As a result, the bimetal nanorod cluster part consisting of an AuNR cluster seed having directionality and a metal shell is formed. Due to the hot spot junction between the interparticle gap of the anisotropically assembled AuNR nanocluster, the Raman intensity is improved remarkably. In addition, because the poly(aniline) part provides an antibody-binding site for detection of a target, the anisotropic Janus nanostructure consisting of the bimetal nanoparticle part containing the metal nanorod cluster having directionality and the polymer part can be used as a metal nanoprobe for measuring a surface-enhanced Raman scattering (SERS) signal for detection of a target material.

Advantageous Effects

Invention 1:

A bimetal-polymer Janus nanostructure according to the present disclosure, which consists of a bimetal nanocluster part selectively functionalized by covalently bonding ODA and a conductive polymer part, exhibits remarkably improved SERS intensity as a controlled self-assembled structure is formed. Accordingly, the Janus nanostructure of the present disclosure can be used as a metal nanoprobe for biosensing and/or bioimaging measurement based on surface-enhanced Raman scattering (SERS) or fluorescence for detection of a target material. Also, the bimetal-polymer Janus nanostructure according to the present disclosure and a self-assembled Janus nanostructure cluster thereof may load a drug in the positively charged conductive polymer part through electrostatic interaction with the negatively charged drug, thereby forming a hydrogel containing a concentrated drug-loaded nanoparticle. The release of the drug can be induced by changing voltage or pH conditions. Accordingly, it can be used as a drug delivery system capable of controlling drug release.

Invention 2:

A Janus nanostructure containing a bimetal Au core-Ag satellite nanoparticle part and a polymer part according to the present disclosure may be used as a metal nanoprobe for detecting a target material based on surface-enhanced Raman scattering (SERS) which exhibits remarkably improved SERS intensity by containing a bimetal nanoparticle part modified with a charged polymer or a ligand.

Invention 3:

An asymmetric Janus nanoprobe according to the present disclosure significantly improves SERS characteristics through interparticle coupling between core and shell nanoparticles in the metal nanocluster. By capturing a target with the polymer part and measuring SERS signals with the metal nanocluster part, target detection and optical characteristics can be improved at the same time. Accordingly, the asymmetric Janus nanoprobe of the present disclosure may be utilized as a functional nanoprobe for SERS-based biosensing.

Invention 4:

An anisotropic Janus nanostructure consisting of a bimetal nanoparticle part containing a metal nanorod cluster having directionality and a polymer part according to the present disclosure can be used as a metal nanoprobe for measuring a surface-enhanced Raman scattering (SERS) signal with remarkably improved Raman intensity because it contains the anisotropically assembled bimetal nanorod cluster.

BRIEF DESCRIPTION OF THE DRAWINGS

Invention 1:

FIG. 1A shows a bimetal-polymer Janus nanostructure, self-assembled Janus nanostructure cluster thereof and synthesis method of superparticular structure thereof, FIG. 1B shows a spontaneous oxidation-reduction reaction between aniline monomer and silver nitrate for synthesis of bimetal-polymer Janus nanostructure, FIG. 1C shows a SERS-based biosensing using superparticular structure of self-assembled Janus nanostructure cluster of bimetal-polymer Janus nanostructure.

FIG. 2A shows a UV-Vis absorption peaks of AuNP, bimetal-polymer Janus nanoparticle (hybrid nanostructure) and superparticular structure thereof (nanoclusters I, II and III), FIG. 2B shows a UV-Vis absorption spectra of RBITC-labeled or MGITC-labeled bimetal-polymer Janus nanostructure (hybrid nanostructure with RB/MG) and self-assembled Janus nanostructure cluster superparticular structure thereof (nanocluster with RB/MG) when $10^{-6}$ M Raman dye and 2.968 μM ODA is added, respectively, FIG. 2C shows a hydrodynamic diameter of AuNP, bimetal-polymer Janus nanoparticle (hybrid nanostructure) and superparticular structure thereof (nanoclusters I, II and III). The average diameter of the Au nanoparticle and the bimetal-polymer Janus nanoparticle was 30.1±0.5 nm and 62.8±2.3 nm, respectively, and the average diameter of the superparticular structure at different clustering levels was 168.3±1.3 nm, 192.4±2.4 nm and 266.3±6.0 nm. The z-potential value of the Au nanoparticle, the bimetal-polymer Janus nanoparticle and the self-assembled Janus nanostructure cluster superparticular structure thereof was −29.5±0.7 mV, −28.0±0.6 mV and −11.2±0.9 mV, respectively. FIG. 2D shows a Hydrodynamic diameter of RBITC-labeled or MGITC-labeled bimetal-polymer Janus nanoparticle and self-assembled Janus nanostructure cluster superparticular structure thereof. The average diameter of the RBITC-labeled or MGITC-labeled bimetal-polymer Janus nanoparticle (hybrid nanostructure with RB/MG) was 122.1±2.4 nm and 112.0±15.9 nm, respectively, and the hydrodynamic diameter of the RBITC-labeled or MGITC-labeled superparticular structure (nanocluster with RB/MG) was 450.1±3.1 nm and 401.1±10.0 nm, respectively.

FIG. 3A shows a relative Raman spectra of RBITC-labeled superparticular structure ($R^2$=0.9826), FIG. 3B shows a Raman intensity of RBITC at 1646 $cm^{-1}$, FIG. 3C shows a Relative Raman spectra of MGITC-labeled superparticular structure, FIG. 3D shows a Raman intensity of MGITC at 1617 $cm^{-1}$ ($R^2$=0.9162), FIG. 3E shows a Raman spectra of bimetal-polymer Janus nanoparticle and superparticular structure thereof at ODA concentration of 2.968 μM and RBITC concentration of $10^{-6}$ M, FIG. 3F shows a Raman intensity of bimetal-polymer Janus nanoparticle and superparticular structure thereof at RBITC concentration of $10^{-6}$ M, FIG. 3G shows a Raman spectra of bimetal-polymer Janus nanoparticle and superparticular structure thereof at ODA concentration of 2.968 μM and MGITC concentration of $10^{-6}$ M, FIG. 3H shows a Raman intensity of bimetal-polymer Janus nanoparticle and superparticular structure thereof at MGITC concentration of $10^{-6}$ M.

FIG. 4A shows a colloidal stability of MGITC-labeled superparticular structure with time, FIG. 4B shows a colloidal stability of RBITC-labeled superparticular structure with time, FIG. 4C shows a batch-to-batch (S1-S5) variability MGITC-labeled superparticular structure, FIG. 4D shows a batch-to-batch (S1-S5) variability of RBITC-labeled superparticular structure.

FIG. 5A shows a TEM image of Au nanoparticle, FIG. 5B shows a TEM image of bimetal-polymer Janus nanostructure before further incubation overnight in 3.6 mM SDS solution, FIG. 5C shows a TEM image of bimetal-polymer Janus nanostructure after further incubation overnight in 3.6 mM SDS solution (The dark area is a bimetal cluster part and the bright area is a polymer part), FIGS. 5D-5F show TEM images of superparticular structure depending on clustering level (With increasing clustering level, self-assembled bimetal-polymer Janus nanostructure clusters in the form of dimer, trimer or tetramer were formed), FIG. 5G shows a SEM image of bimetal-polymer Janus nanostructure, FIG. 5H shows a SEM image of self-assembled bimetal-polymer Janus nanostructure cluster superparticular structure. The scale bar of the TEM images is 100 nm shown in FIG. 5A or 200 nm shown in FIGS. 5B-5F and the scale bar of the SEM images is 1.0 μm as shown in FIGS. 5G-5H.

FIG. 6A shows a cumulative release upon electrical stimulation of +1.5 V, FIG. 6B shows a cumulative release upon electrical stimulation of −1.5 V, FIG. 6C shows a UV-vis absorbance of fluorescein-loaded bimetal-polymer Janus nanoparticle at pH 4, 7 and 11, FIG. 6D shows a Raman spectra of MGITC from fluorescein-loaded bimetal-polymer Janus nanostructure. The Raman peaks of MGITC and fluorescein were at 1617 $cm^{-1}$ and 1176 $cm^{-1}$, respectively.

Figure 10A:
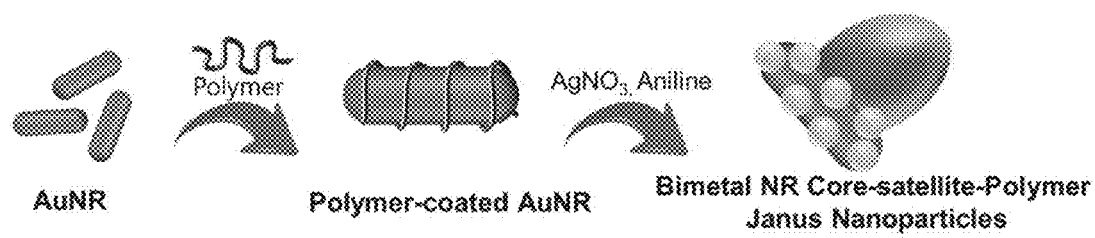
Figure 10B:
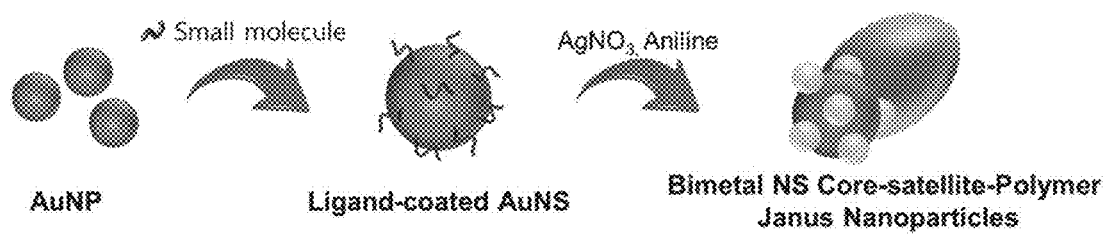
Figure 10C:
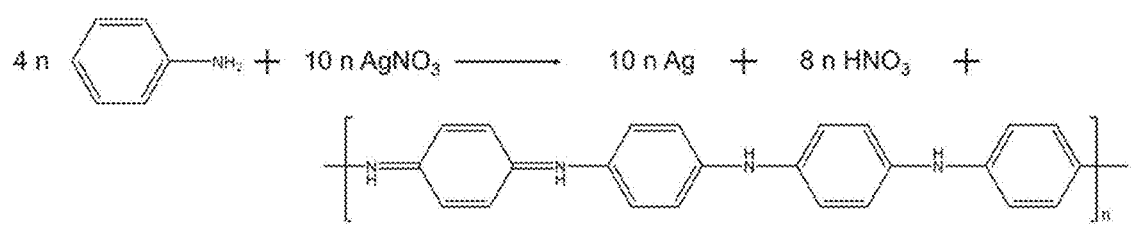
Figure 10D:
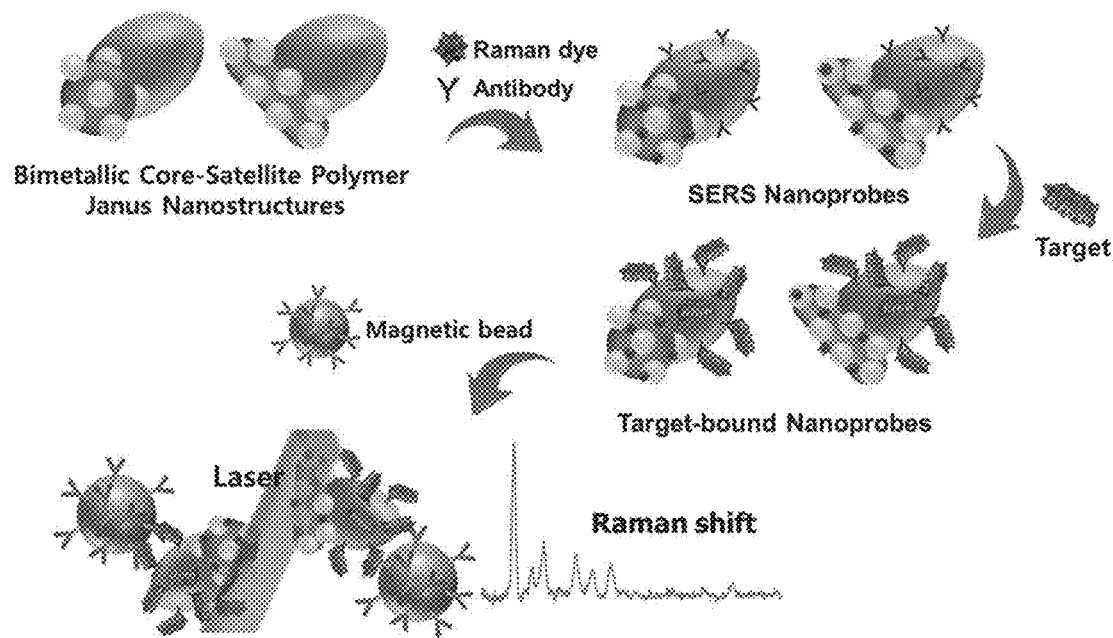

Invention 2:

FIGS. 10A-10D schematically shows preparation of a Janus nanostructure consisting of a core-satellite bimetal nanoparticle part and a polymer part and its application to SERS-based biosensing; FIG. 10A shows a method for preparing Janus nanostructure consisting of AuNR core-Ag satellite bimetal nanoparticle part and polymer part, FIG. 10B shows a method for preparing Janus nanostructure consisting of AuNP core-Ag satellite bimetal nanoparticle part and polymer part, FIG. 10C shows aspontaneous oxidation-reduction reaction between aniline monomer and silver nitrate, FIG. 10D shows a method for detecting target material based on surface-enhanced Raman scattering (SERS) using Janus nanostructure consisting of core-satellite bimetal nanoparticle part and polymer part.

Figure 11A:
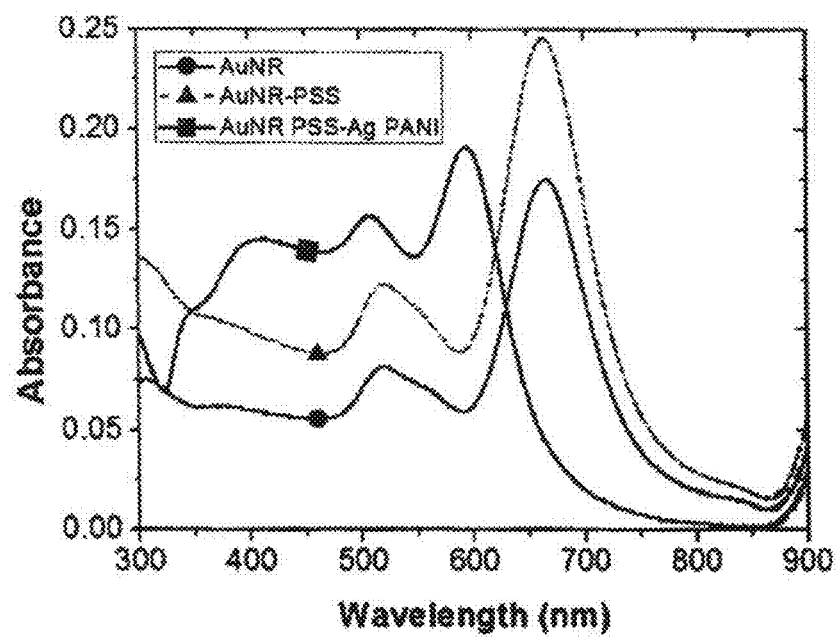
Figure 11B:
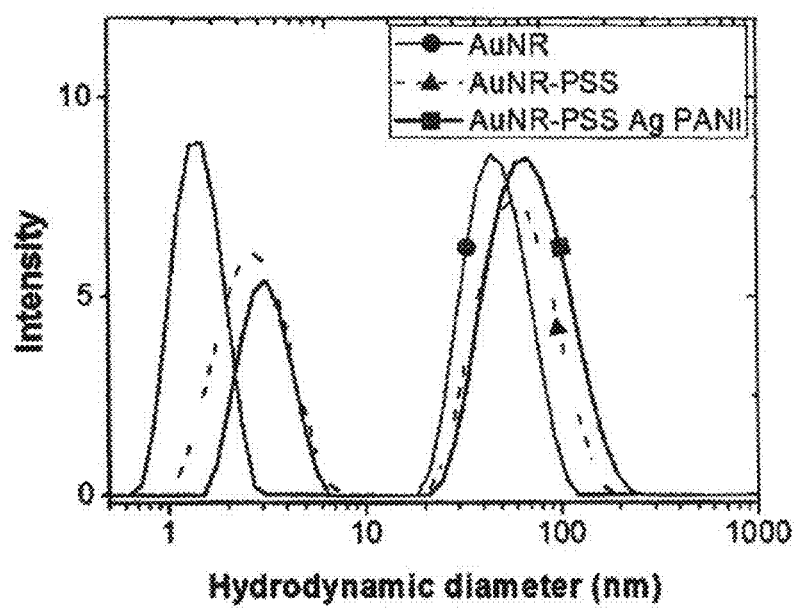
Figure 11C:
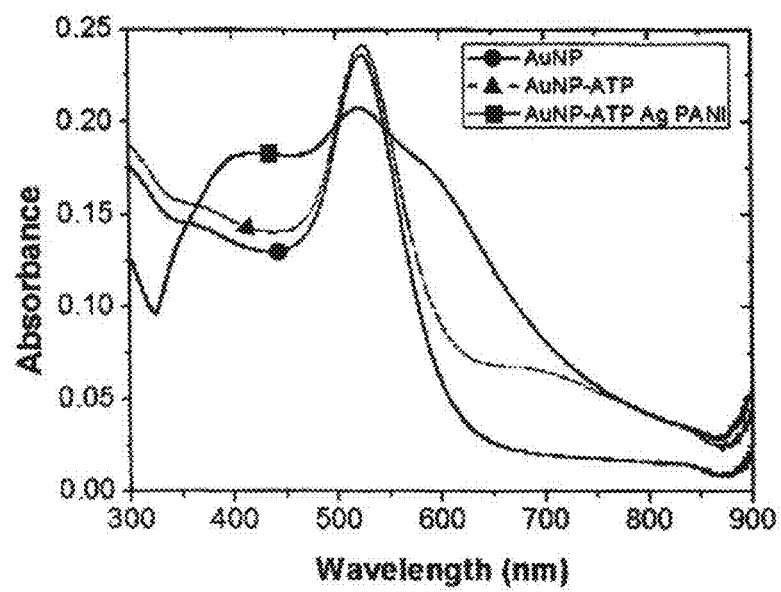
Figure 11D:
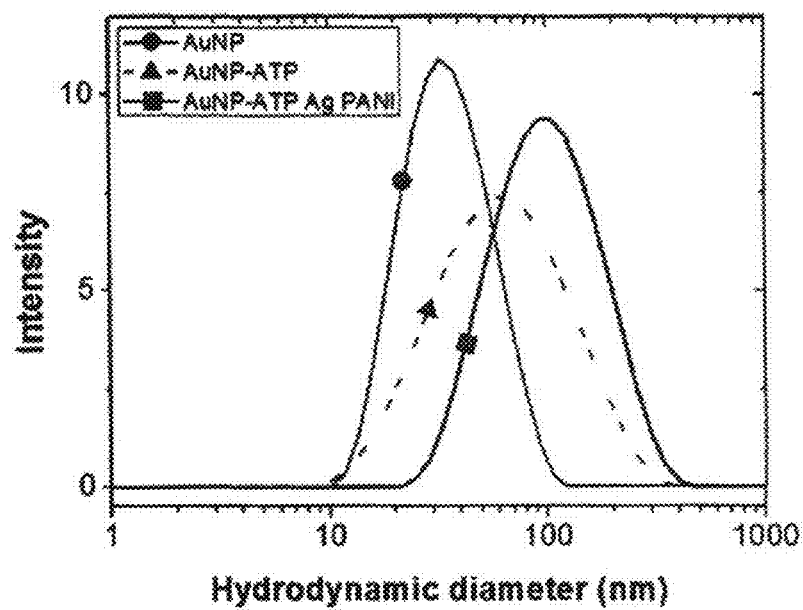

FIGS. 11A-11D shows the UV-Vis absorbance and hydrodynamic diameter of an Au nanoparticle, PSS-coated AuNR (AuNR-PSS) or ATP-coated AuNP (AuNP-ATP) and a Janus nanostructure consisting of an Au core-Ag satellite bimetal part and a polymer part (AuNR-PSS Ag PANI or AuNP-ATP Ag PANI); FIG. 11A shows the absorbance of AuNR, PSS-coated AuNR (AuNR-PSS) and Janus nanostructure consisting of Au core-Ag satellite bimetal part and polymer part (AuNR-PSS Ag PANI) (After the synthesis of the Janus nanostructure consisting of the Au core-Ag satellite bimetal part and the polymer part, new Ag absorption peaks appeared in the range from 380 nm to 480 nm and the longitudinal and transverse LSPR peaks of AuNR at 525 nm and 664 nm were blue-shifted to 508 nm and 595 nm, respectively.), FIG. 11B shows hydrodynamic diameter of AuNR, PSS-coated AuNR (AuNR-PSS) and Janus nanostructure consisting of Au core-Ag satellite bimetal part and polymer part (AuNR-PSS Ag PANI) (The longitudinal and transverse average diameters of AuNR were 1.5±0.1 nm and 49.9±0.9 nm, respectively, the average diameters of PSS-coated AuNR were 2.8±0.1 nm and 63.4±0.5 nm and the average diameters of the bimetal core-satellite Janus nanostructure were 3.1±0.1 nm and 73.0±0.8 nm due to the aspherical shape.), FIG. 11C shows the absorbance of AuNP, ATP-coated AuNP (AuNP-ATP) and Janus nanostructure consisting of Au core-Ag satellite bimetal part and polymer part (AuNP-ATP Ag PANI) (The UV-vis absorption peak of citrate-capped AuNP at 524 nm was red-shifted to 526 nm, suggesting adsorption of ATP on the surface of AuNP.), FIG. 11D shows the hydrodynamic diameter of AuNP, ATP-coated AuNP (AuNP-ATP) and Janus nanostructure consisting of Au core-Ag satellite bimetal part and polymer part (AuNP-ATP Ag PANI) (The average diameter of the AuNP, ATP-coated AuNP and the bimetal core-satellite Janus nanostructure was 19.0±0.8 nm, 33.3±0.4 nm and 72.6±0.6 nm, respectively.).

Figure 12A:
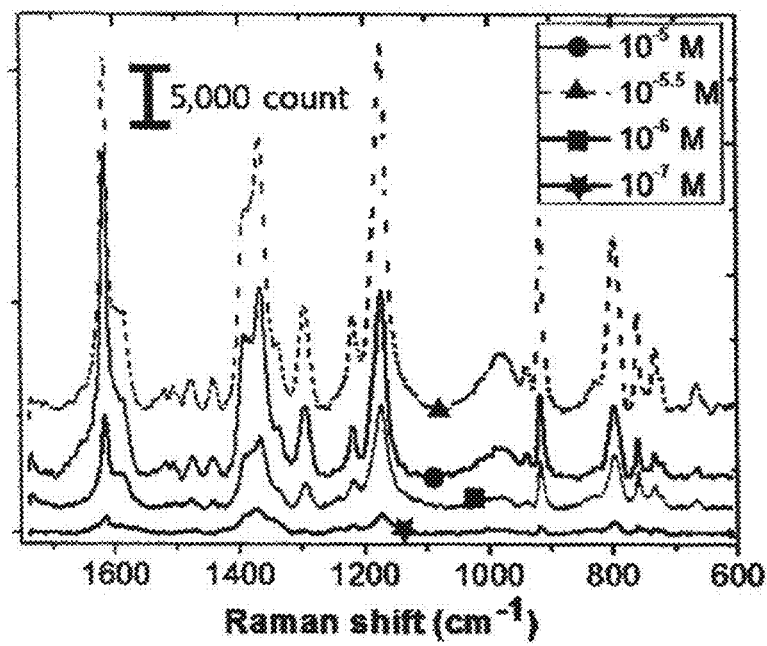
Figure 12B:
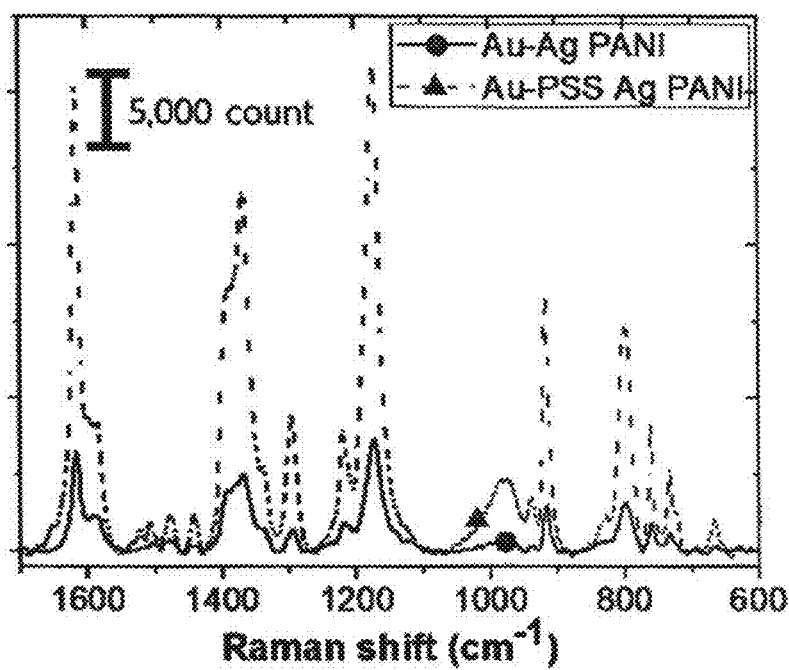
Figure 12C:
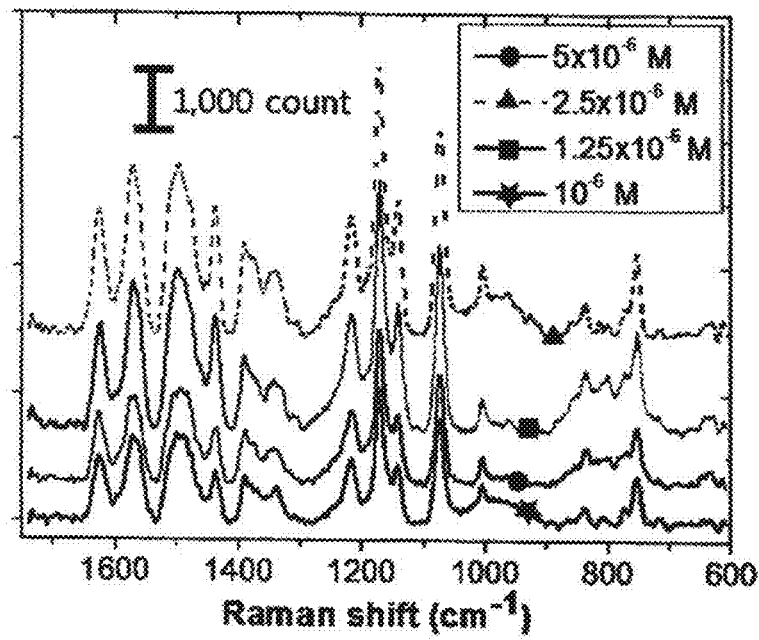
Figure 12D:
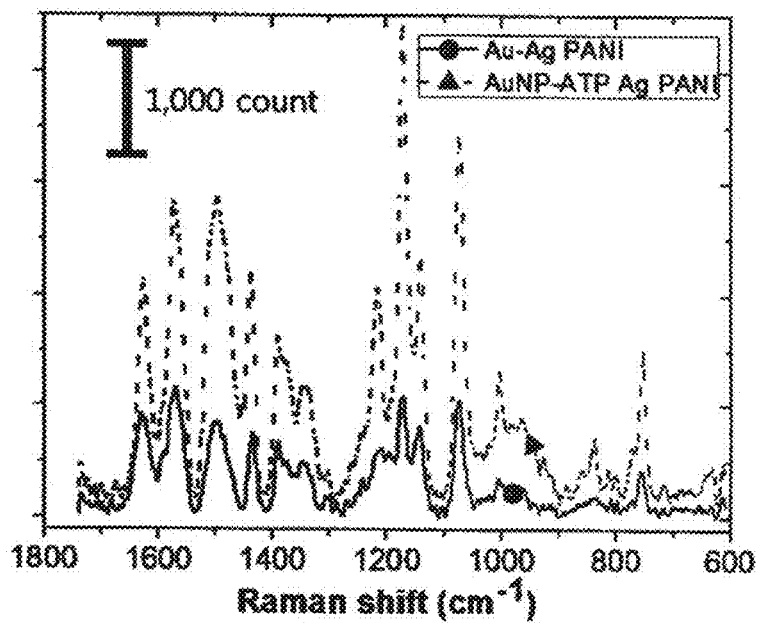

FIGS. 12A-12D shows that FIG. 12A is the relative the Raman shift of MGITC ($10^7$-$10^{-5.5}$ M)-labeled AuNR core-Ag satellite depending on the concentration of the Raman dye, FIG. 12B shows the relative Raman shift of bimetal AuNR core-Ag satellite (Au-PSS Ag PANI, Example 1) or Ag shell nanoparticle (Au—Ag PANI, Comparative Example 1) at MGITC concentration of $10^{-5.5}$ M, FIG. 12C shows the relative the Raman shift of ATP ($10^{-6}$-$5.0 \times 10^{-6}$ M)-labeled AuNP core-Ag satellite depending on the concentration of the Raman dye, FIG. 12D shows the relative the Raman shift of ATP ($2.5 \times 10^{-6}$ M)-labeled AuNP core-Ag satellite (Au-ATP Ag PANI, Example 2) or Ag shell nanoparticle (Au—Ag PANI, Comparative Example 1).

Figure 13A:
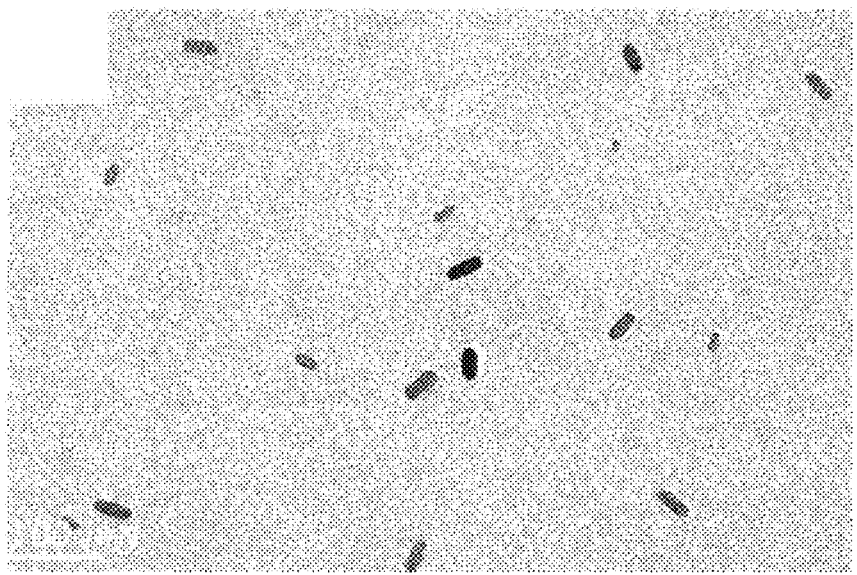
Figure 13B:
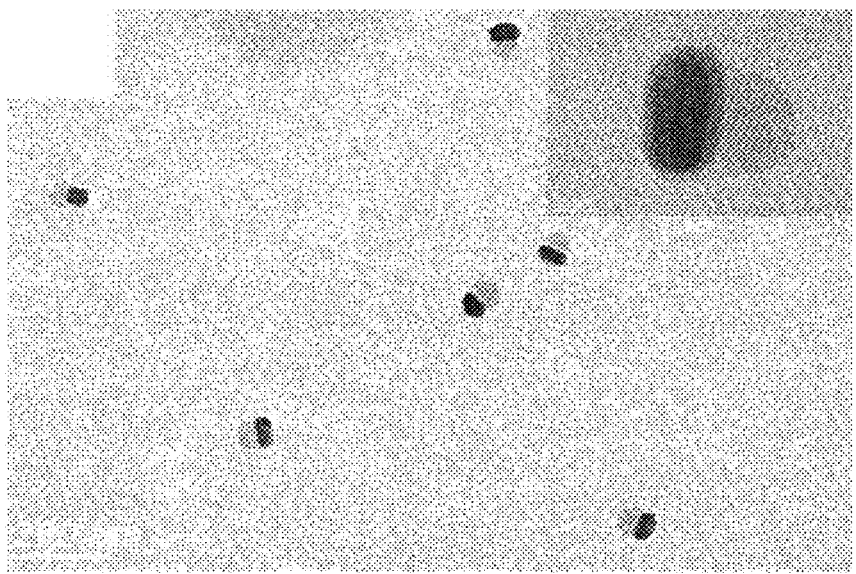
Figure 13C:
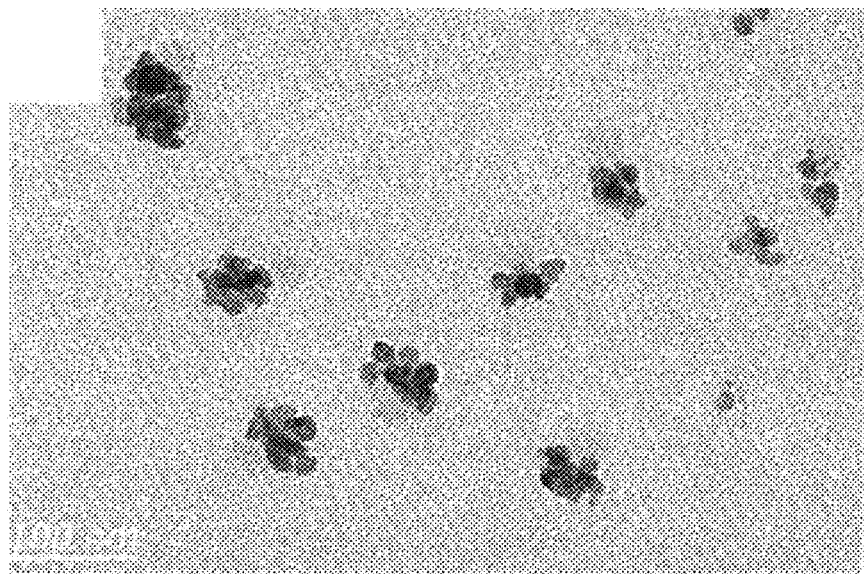
Figure 13D:
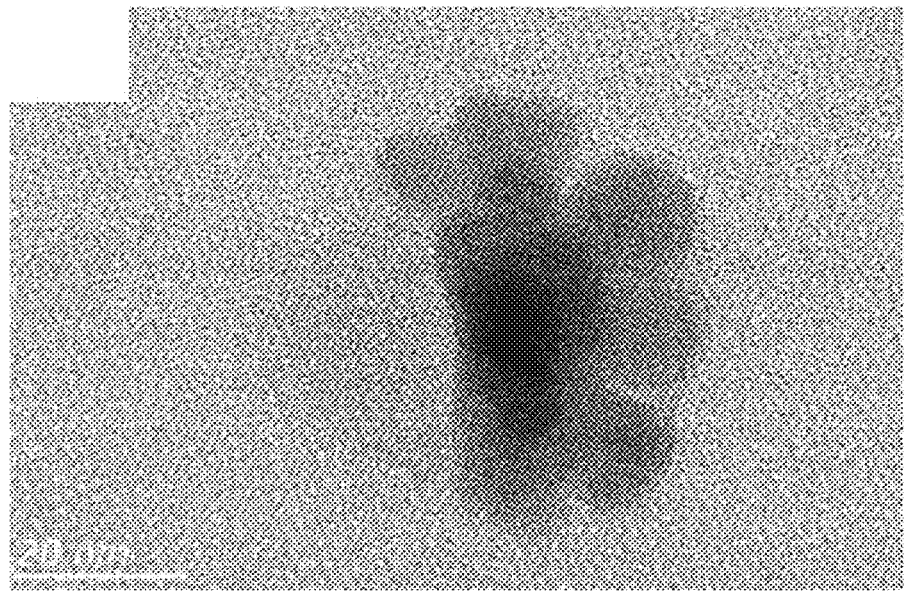
Figure 13E:
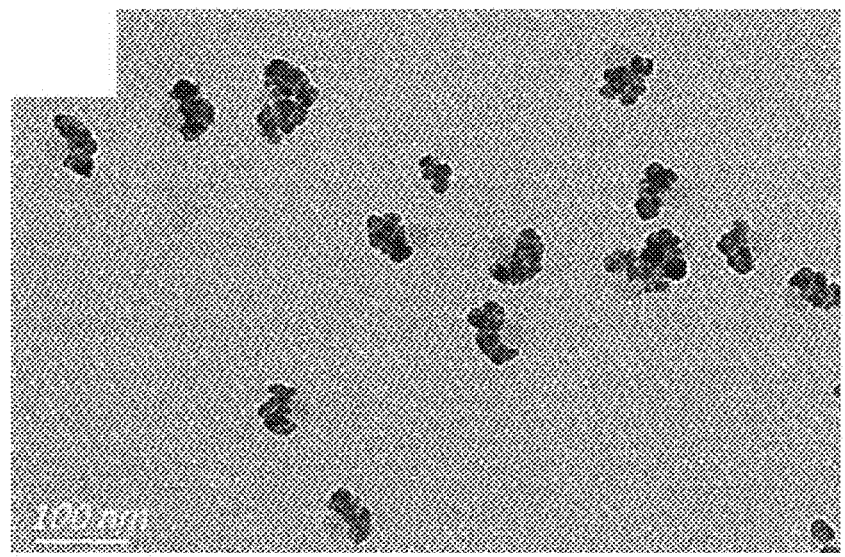
Figure 13F:
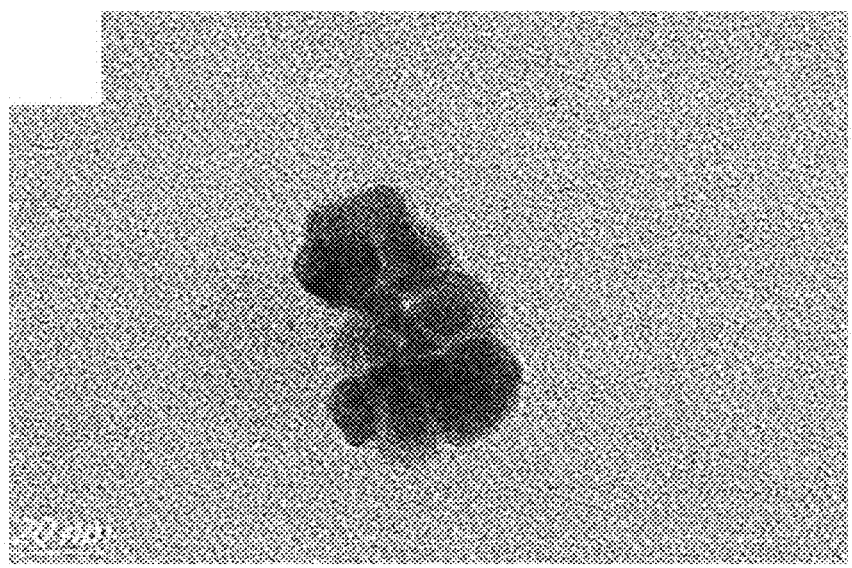
Figure 13G:
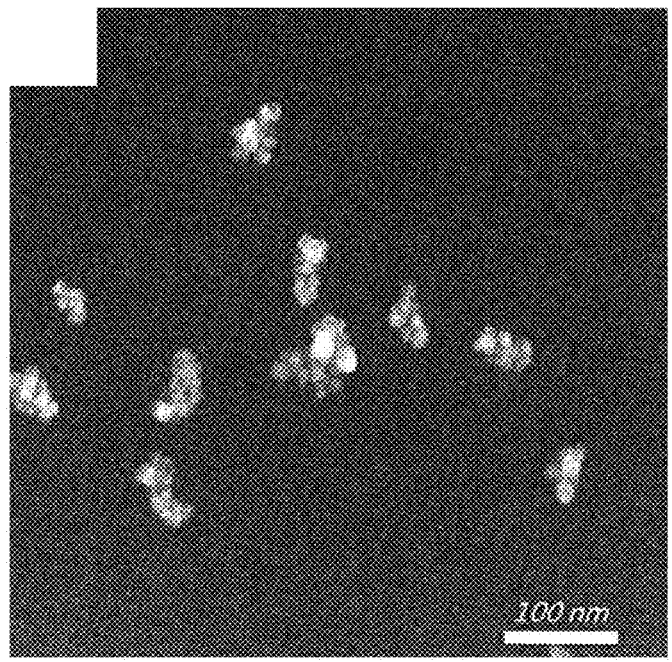
Figure 13H:
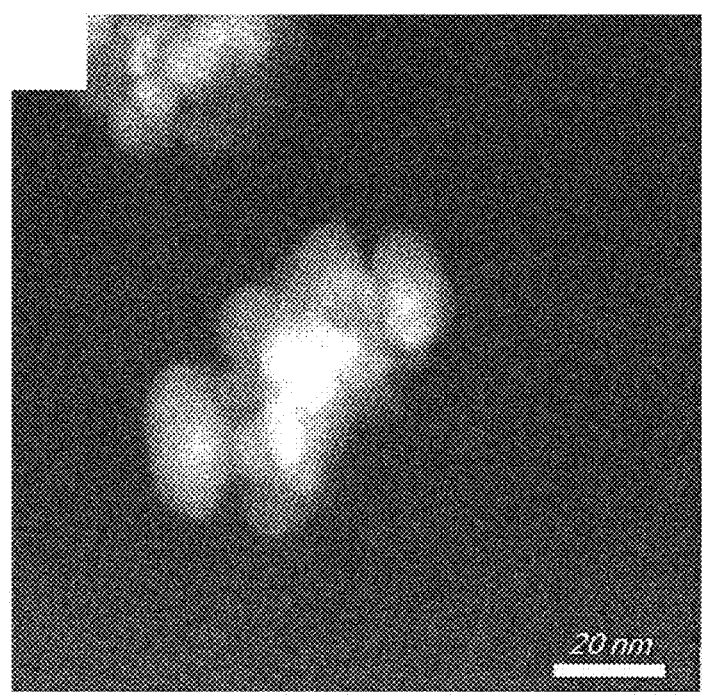

FIGS. 13A-13H shows the transmission electron microscopy (TEM) and high-angle annular dark-field scanning TEM (HAADF-STEM) images of nanoparticles; FIG. 13A shows a TEM image of AuNR, FIG. 13B shows a TEM image of bimetal AuNR core-Ag nanoparticle, FIGS. 13C-13D show TEM images of bimetal AuNR core-Ag satellite nanoparticle at different magnifications, FIGS. 13G-13H show HAADF-STEM images of bimetal AuNR core-Ag satellite nanoparticle at different magnifications. Scale bars: 100 nm (as shown in FIGS. 13A, 13C and 13E), 200 nm (as shown in FIG. 13B and FIG. 13G), and 20 nm (as shown in FIG. 13D, FIG. 13F and FIG. 13H).

Figure 14A:
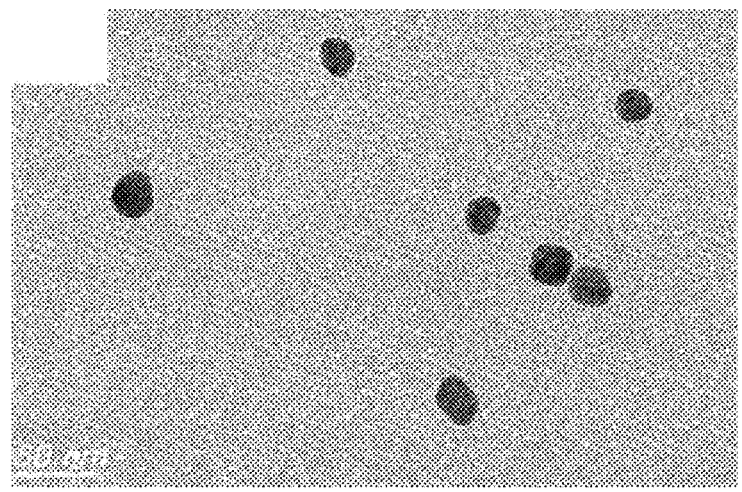
Figure 14B:
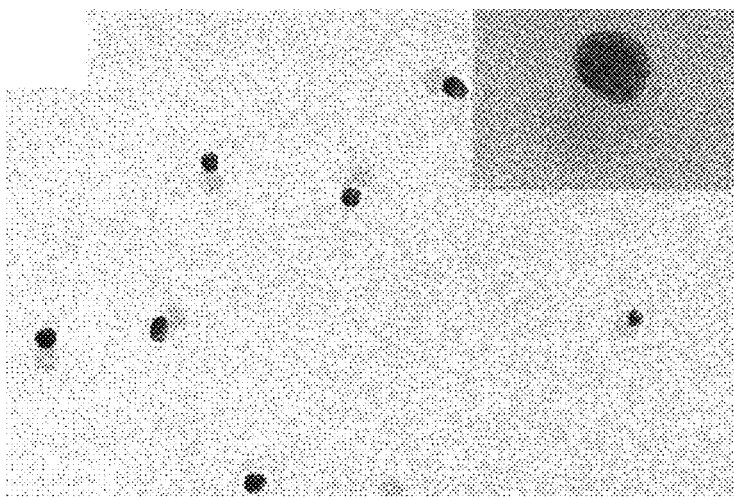
Figure 14C:
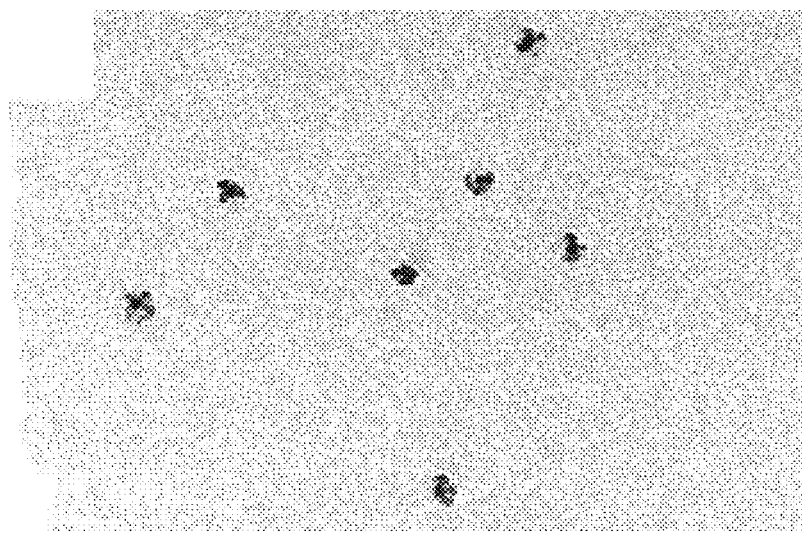
Figure 14D:
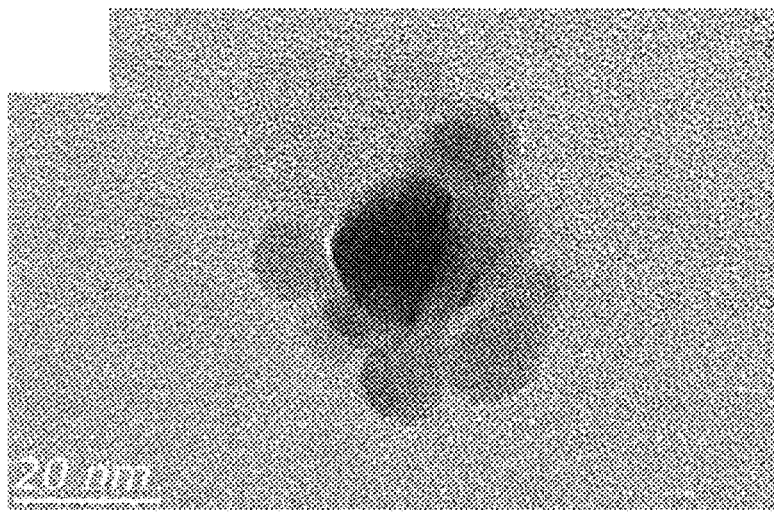
Figure 14E:
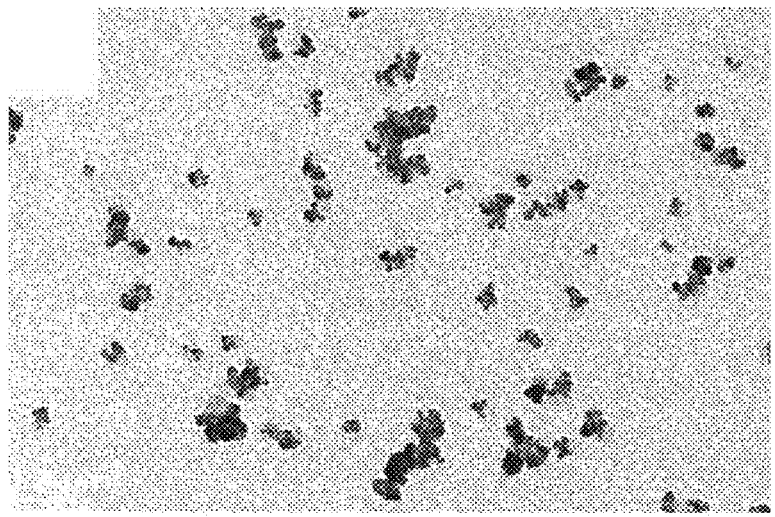
Figure 14F:
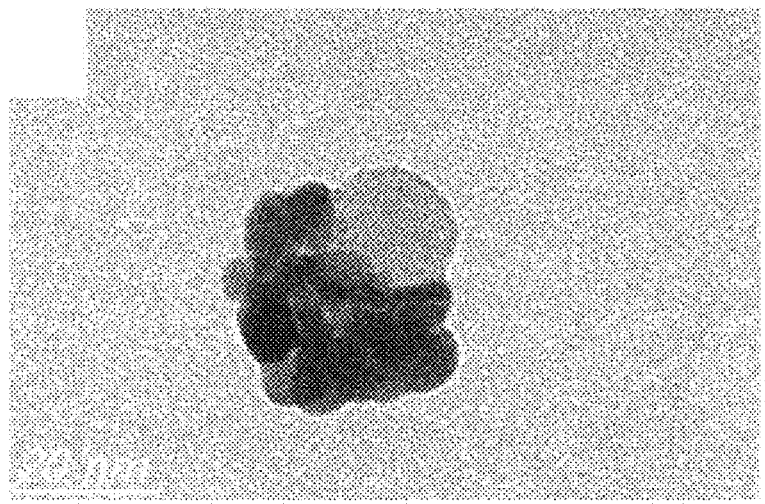
Figure 14G:
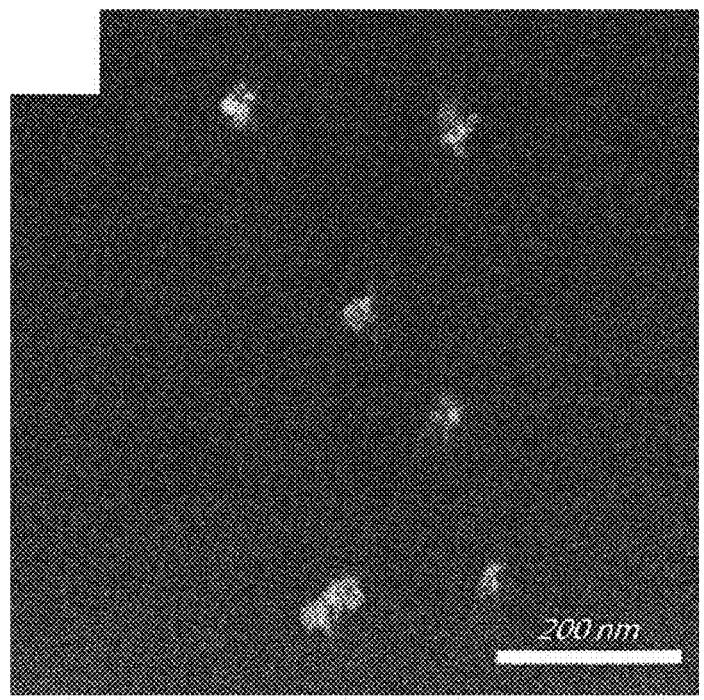
Figure 14H:
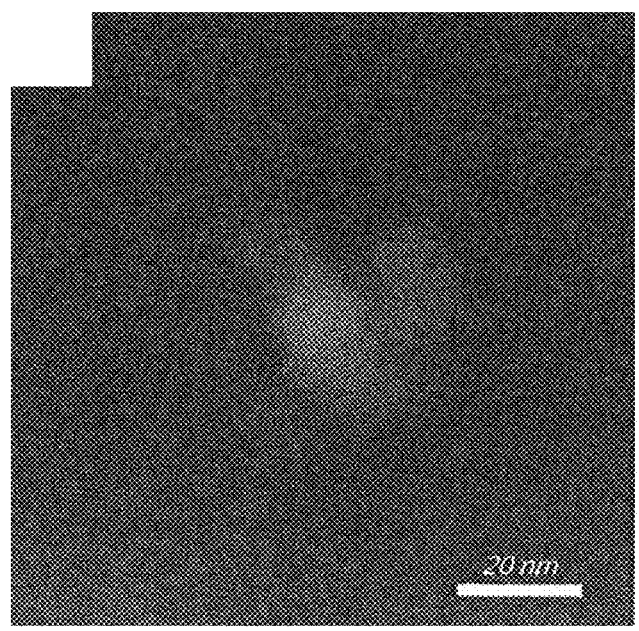

FIGS. 14A-14H shows the transmission electron microscopy (TEM) and high-angle annular dark-field scanning TEM (HAADF-STEM) images of nanoparticles; FIG. 14A shows a TEM image of AuNP, FIG. 14B shows a TEM image of bimetal AuNP core-Ag nanoparticle, FIGS. 14C and 14D show TEM images of bimetal AuNP core-Ag satellite nanoparticle at different magnifications, FIGS. 14G and 14H show HAADF-STEM images of bimetal AuNP core-Ag satellite nanoparticle at different magnifications. Scale bars: 50 nm as seen in FIG. 14A, 200 nm (as seen in FIGS. 14B, 14C, and 14E), and 20 nm (as seen in FIGS. 14D, 14F and 14H).

Figure 15A:
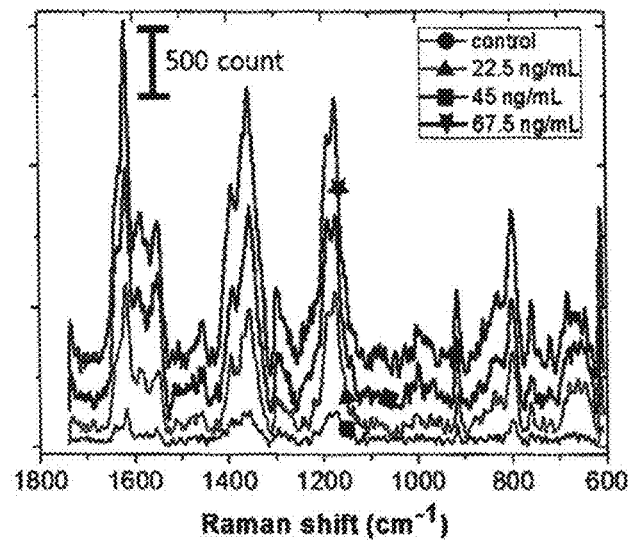
Figure 15B:
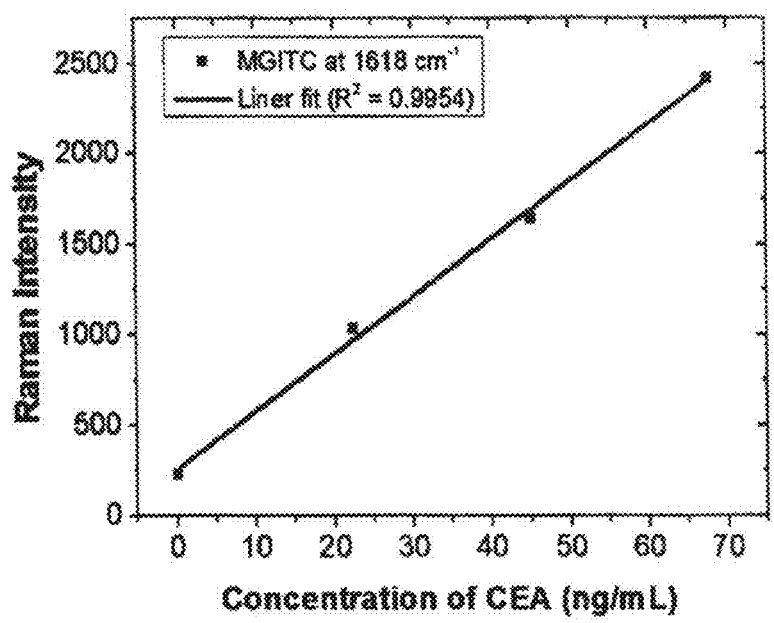

FIGS. 15A and 15B shows the Raman spectra and Raman intensity depending on CEA concentration. The SERS peak intensity of the Janus nanostructure containing the MGITC-labeled bimetal Au core-Ag satellite part and the polymer part at 1618 $cm^{-1}$ increased linearly with the CEA concentration. $R^2$=0.9954. Control is a CEA-free control group.

Figure 16A:
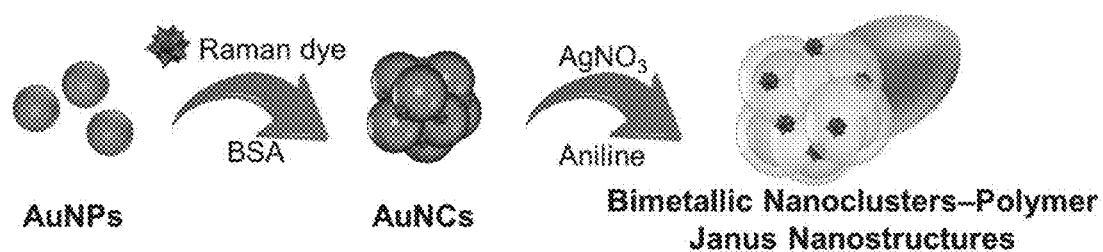
Figure 16B:
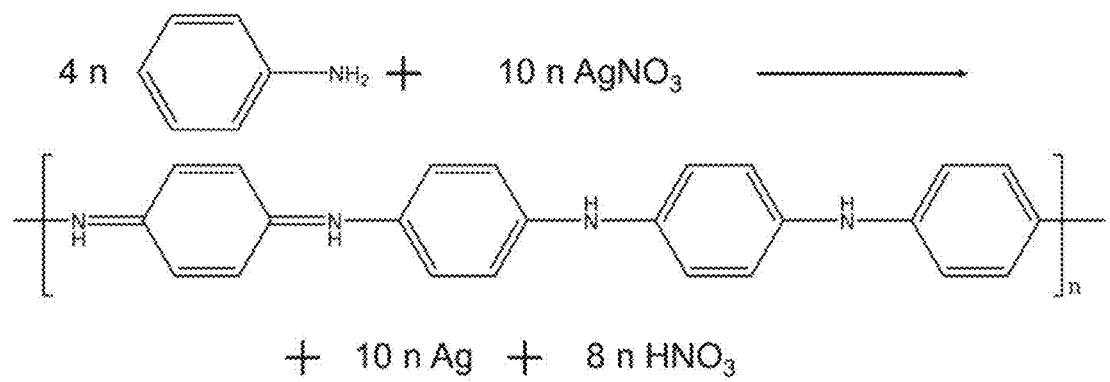
Figure 16C:
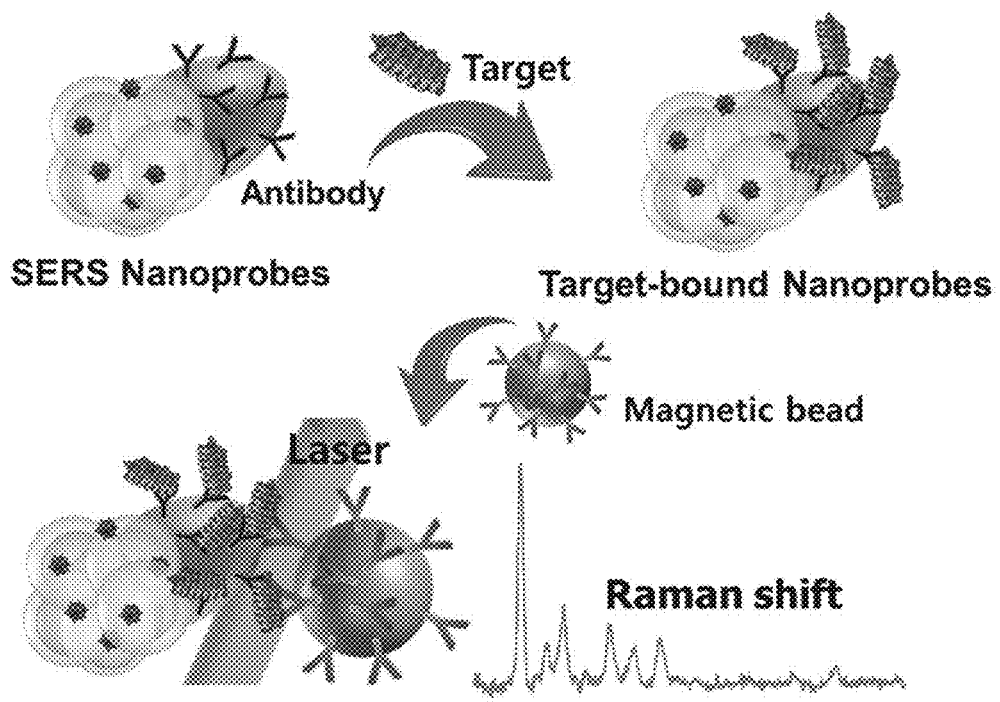

Invention 3:

FIGS. 16A-16C schematically shows the synthesis of an asymmetric Janus nanocluster-polymer nanostructure and its application to SERS-based biosensing; FIG. 16A shows a method for preparing asymmetric Janus nanocluster-polymer nanostructure based on oxidation-reduction reaction, FIG. 16B shows spontaneous oxidation-reduction reaction between silver nitrate and aniline monomer, FIG. 16C shows SERS-based biosensing method using asymmetric Janus nanocluster-polymer nanostructure.

Figure 17A:
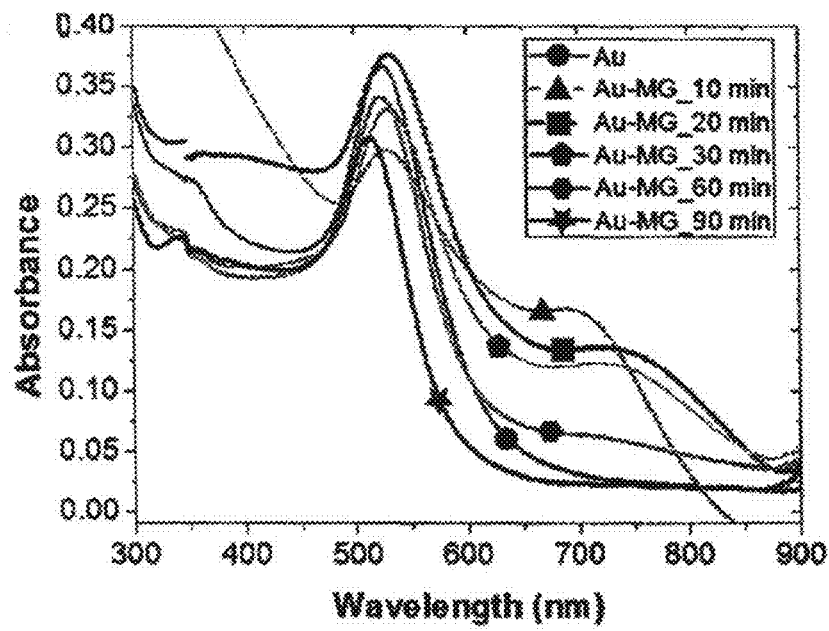
Figure 17B:
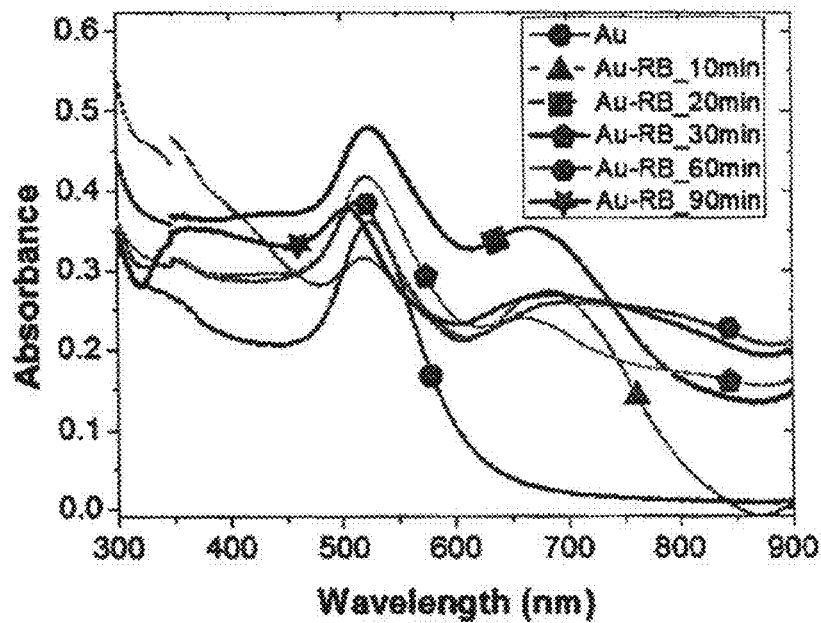
Figure 17C:
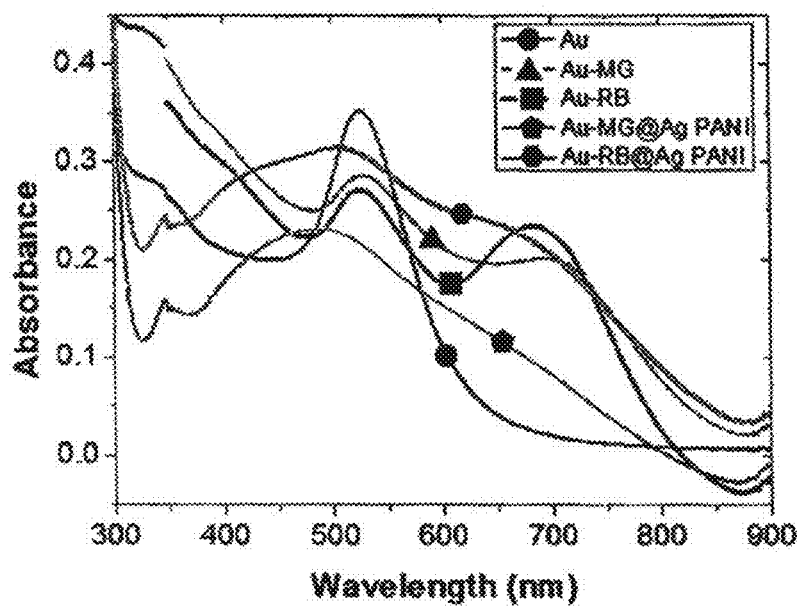
Figure 17D:
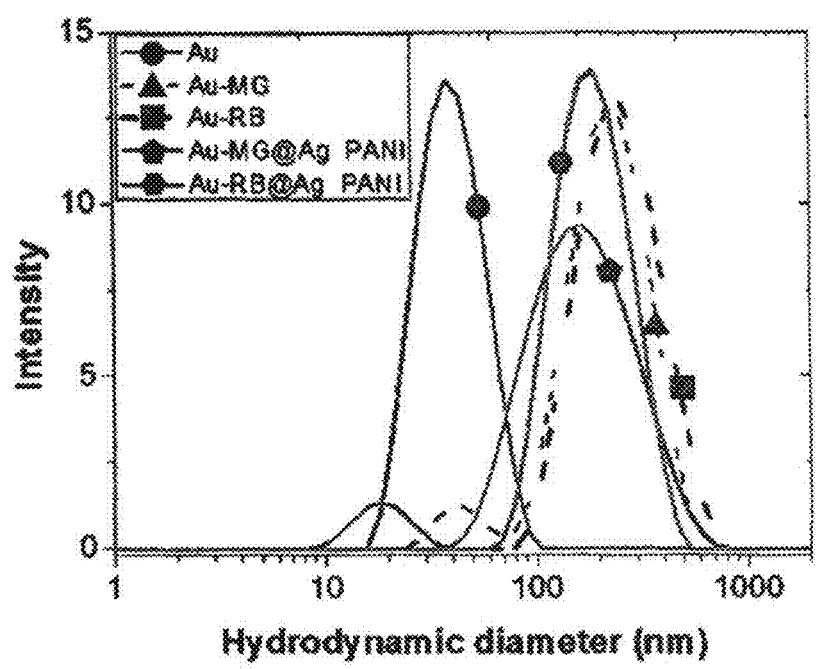

FIGS. 17A-17D shows the UV-Vis absorbance of AuNP, a Raman dye-induced Au nanocluster and an asymmetric Janus nanocluster-polymer nanostructure; FIG. 17A shows a UV-Vis absorption peaks of AuNP (Au) and MGITC-induced Au nanocluster (Au_MG), FIG. 17B shows UV-Vis absorption peaks of AuNP (Au) and RBITC-induced Au nanocluster (Au_RB), FIG. 17C shows UV-Vis absorption peaks of asymmetric Janus nanocluster-polymer nanostructure (Au-MG@Ag PANI or Au-RB@Ag PANI), FIG. 17D shows hydrodynamic diameter and size distribution of AuNP, Au nanocluster and asymmetric Janus nanocluster-polymer nanostructure (Au-MG@Ag PANI or Au-RB@Ag PANI). The average diameter of AuNP and the MGITC- or RBITC-induced Au nanocluster was 18.9±0.4 nm, 152.9±2.8 nm and 115.7±1.8 nm and the average diameter of the MGITC- or RBITC-induced asymmetric Janus nanocluster-polymer nanostructure was 205±4.5 nm and 186.3±2.1 nm.

Figure 18A:
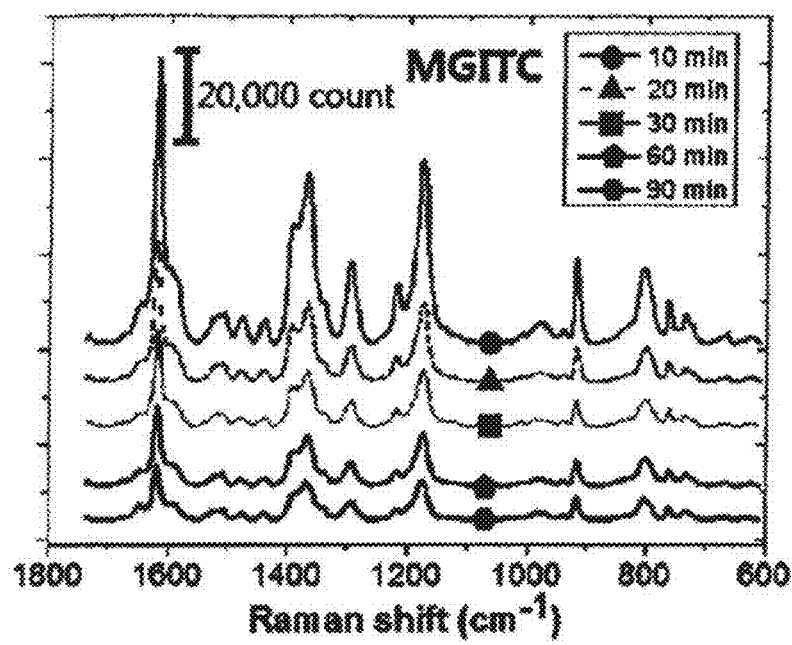
Figure 18B:
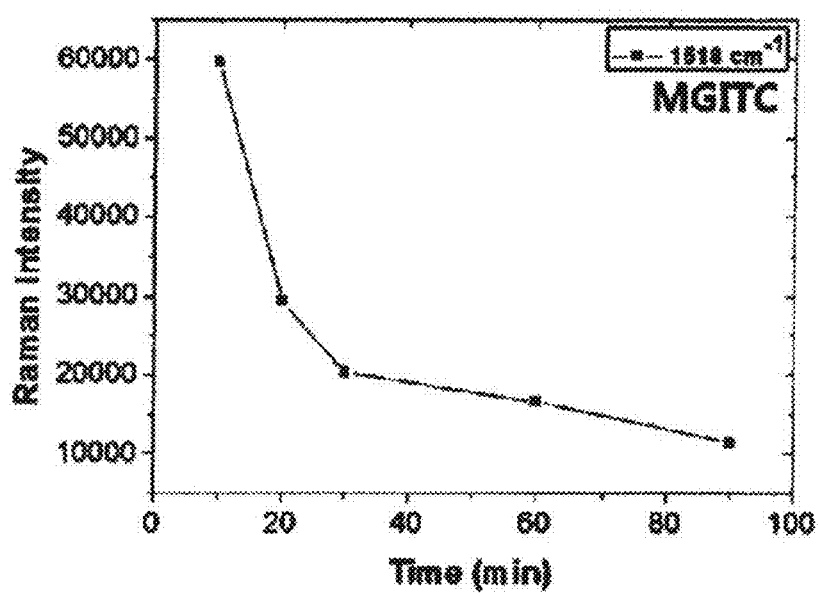
Figure 18C:
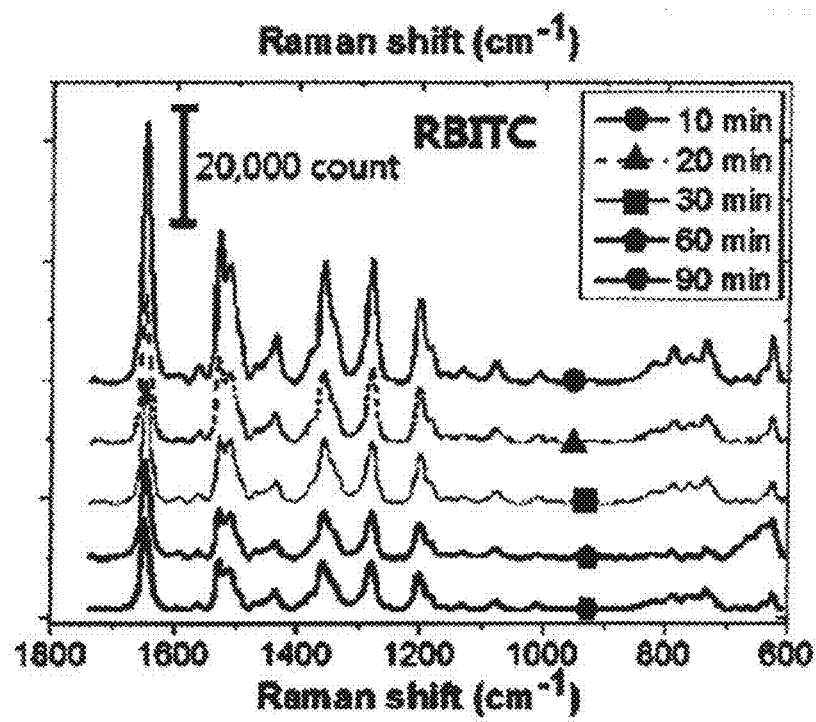
Figure 18D:
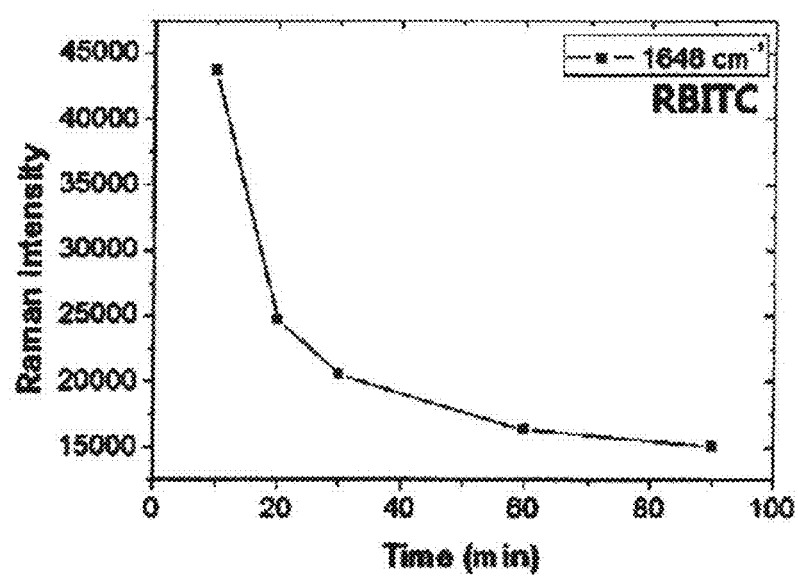
Figure 18E:
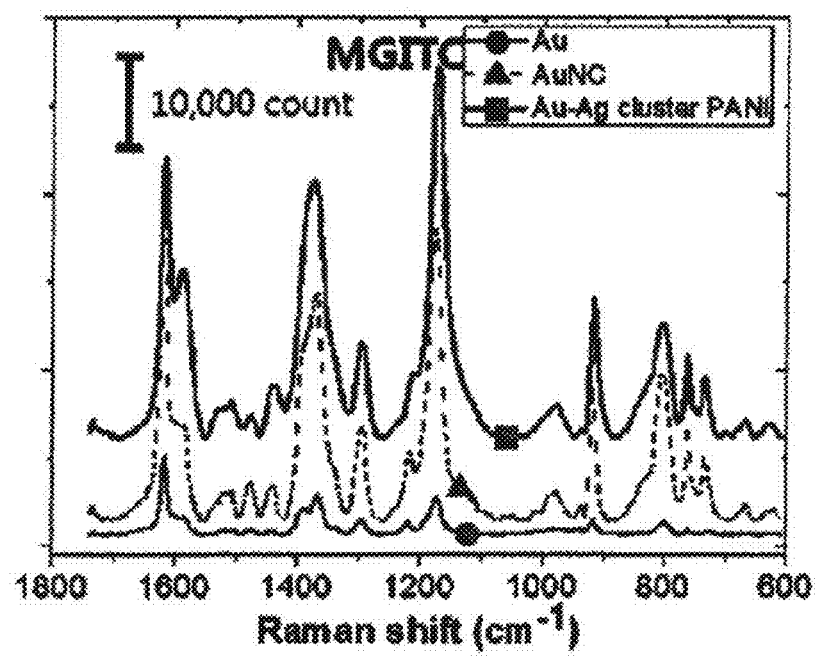
Figure 18F:
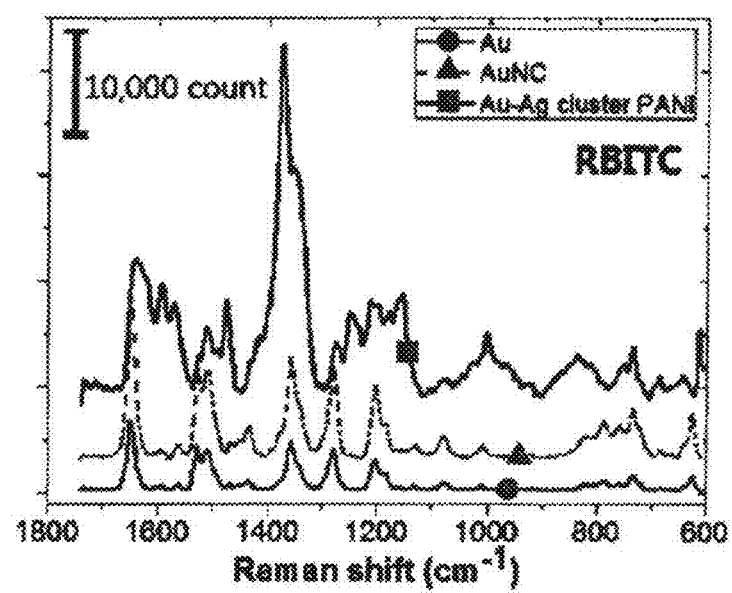

FIGS. 18A-18F shows the relative Raman spectra of an MGITC- or RBITC-induced Au nanocluster during the cluster formation depending on incubation time; FIG. 18A shows a relative Raman spectra of MGITC-induced Au nanocluster, FIG. 18B shows Raman intensity of MGITC-induced Au nanocluster, FIG. 18C shows relative Raman spectra of RBITC-induced Au nanocluster, FIG. 18D shows Raman intensity of RBITC-induced Au nanocluster, FIG. 18E shows relative Raman spectra of MGITC-labeled AuNP (Au), MGITC-induced Au nanocluster (AuNC) and asymmetric Janus nanocluster-polymer nanostructure (Au—Ag cluster PANI, Au-MG@Ag PANI), FIG. 18F shows relative Raman spectra of RBITC-labeled AuNP (Au), RBITC-induced Au nanocluster (AuNC) and asymmetric Janus nanocluster-polymer nanostructure (Au—Ag cluster PANI, Au-RB@Ag PANI).

Figure 19A:
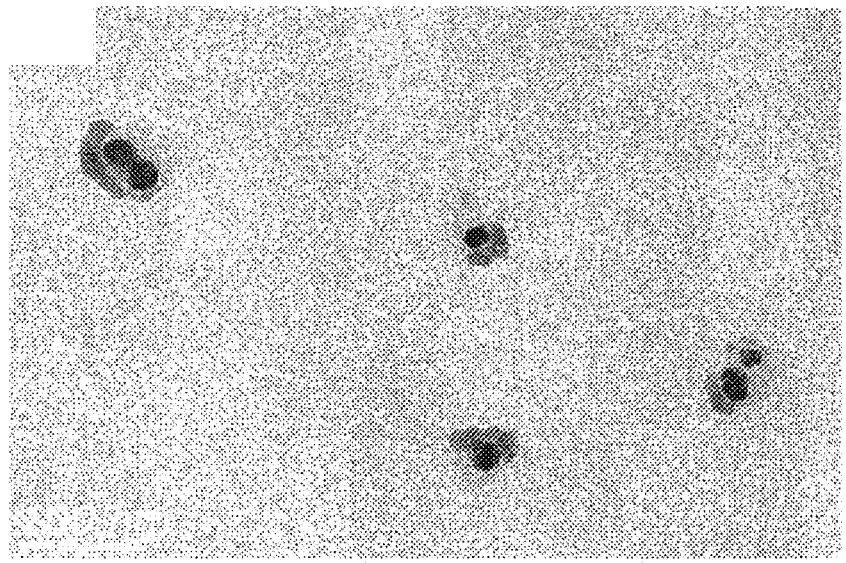
Figure 19B:
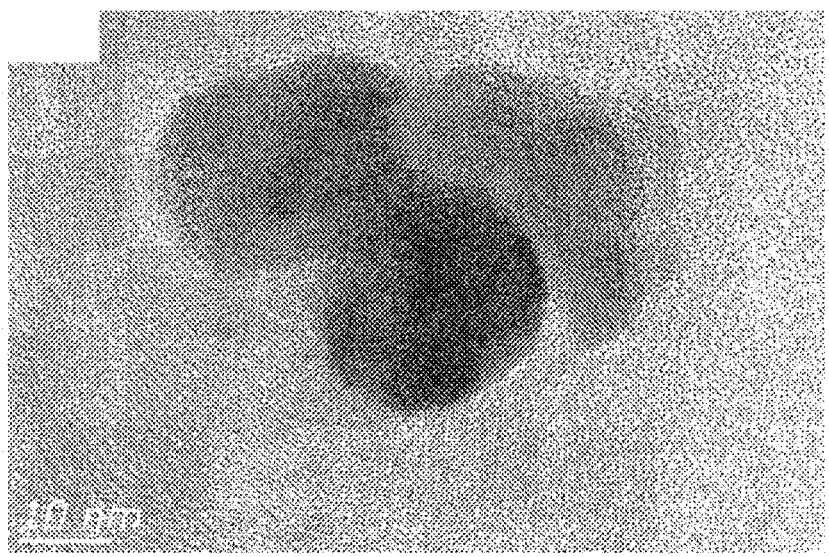
Figure 19C:
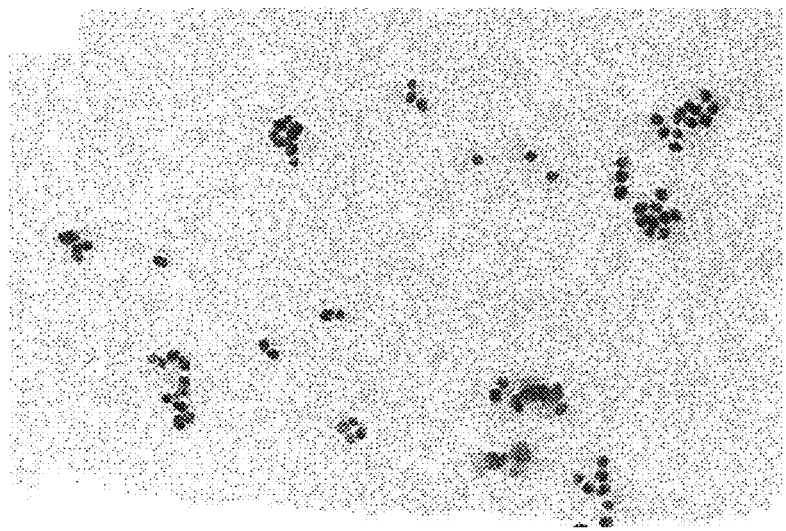
Figure 19D:
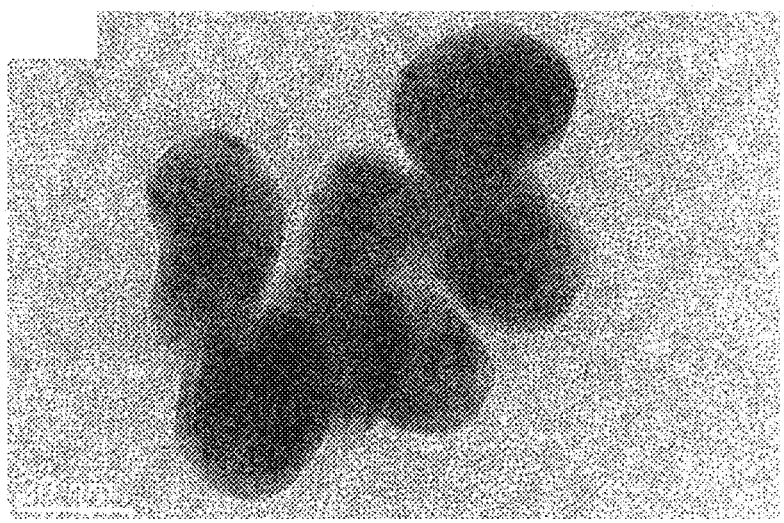

FIGS. 19A-19D shows the TEM images of an asymmetric Janus nanocluster-polymer nanoparticle induced by MGITC at a final concentration of 1.5 μM; FIGS. 19A-19B show asymmetric Janus nanocluster-polymer nanoparticle not stabilized by BSA (The asymmetric Janus nanocluster-polymer nanoparticle was not formed.), FIGS. 19C-19D asymmetric Janus nanocluster-polymer nanoparticle stabilized by BSA. Scale bars: 100 nm as shown in FIG. 19A, 10 nm as shown in FIG. 19B, 200 nm as shown in FIG. 19C, and 20 nm as shown in FIG. 19D.

Figure 20A:
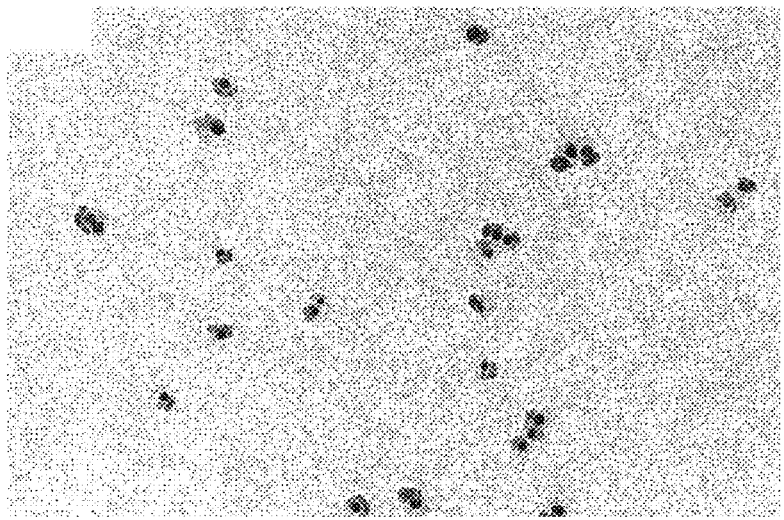
Figure 20B:
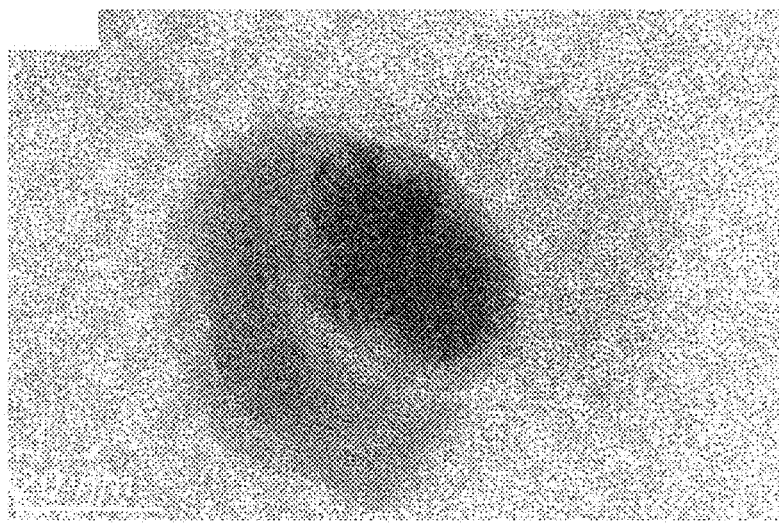
Figure 20C:
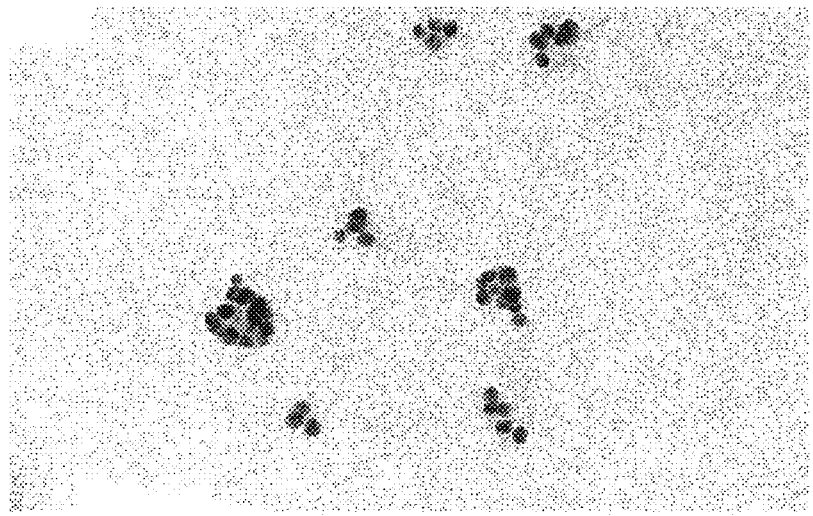
Figure 20D:
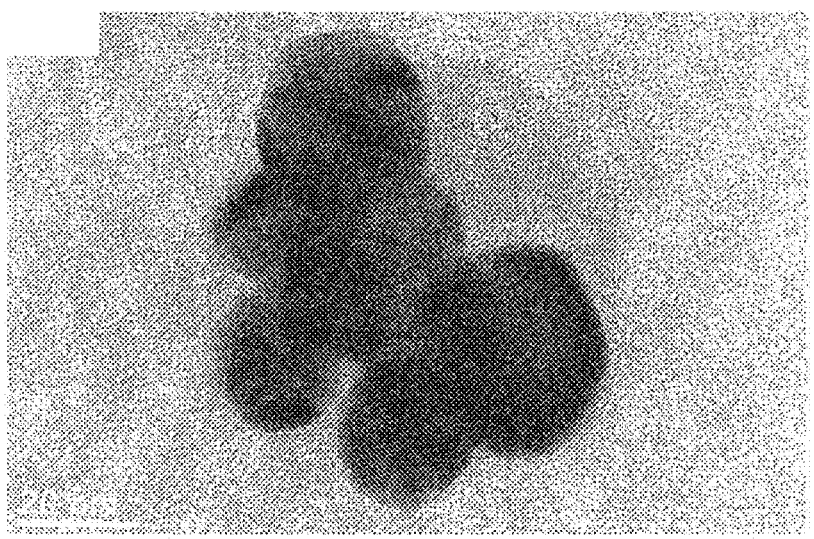

FIGS. 20A-20D shows the TEM images of an asymmetric Janus nanocluster-polymer nanoparticle induced by RBITC at a final concentration of 3.75 μM; FIGS. 20A and 20B show asymmetric Janus nanocluster-polymer nanoparticle not stabilized by BSA (The asymmetric Janus nanocluster-polymer nanoparticle was not formed.), FIGS. 20C and 20D show asymmetric Janus nanocluster-polymer nanoparticle stabilized by BSA. Scale bars: 100 nm as shown in FIGS. 20A and 20C, and 20 nm as shown in FIGS. 20B and 20D.

Figure 21A:
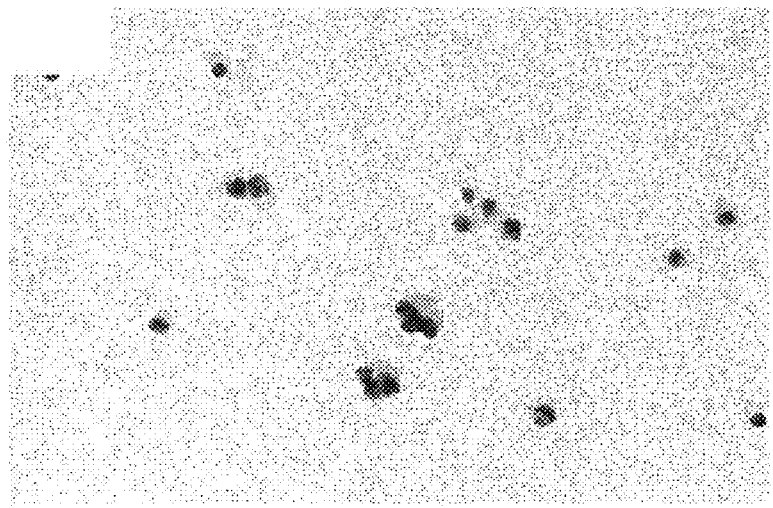
Figure 21B:
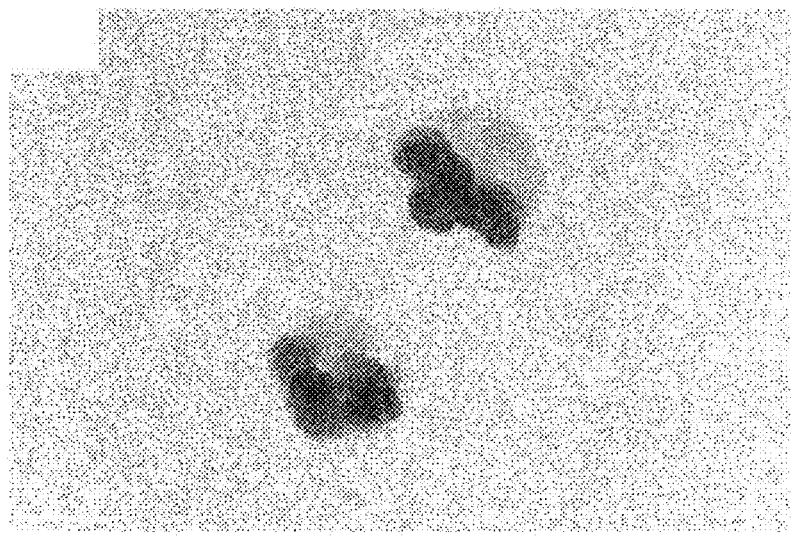
Figure 21C:
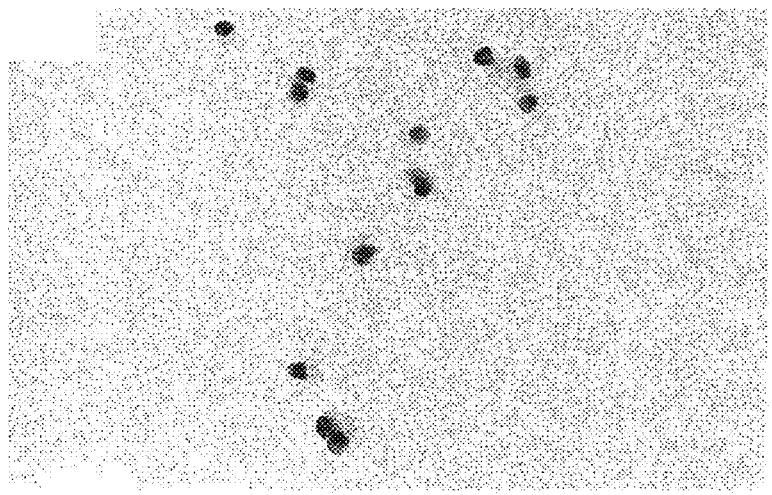
Figure 21D:
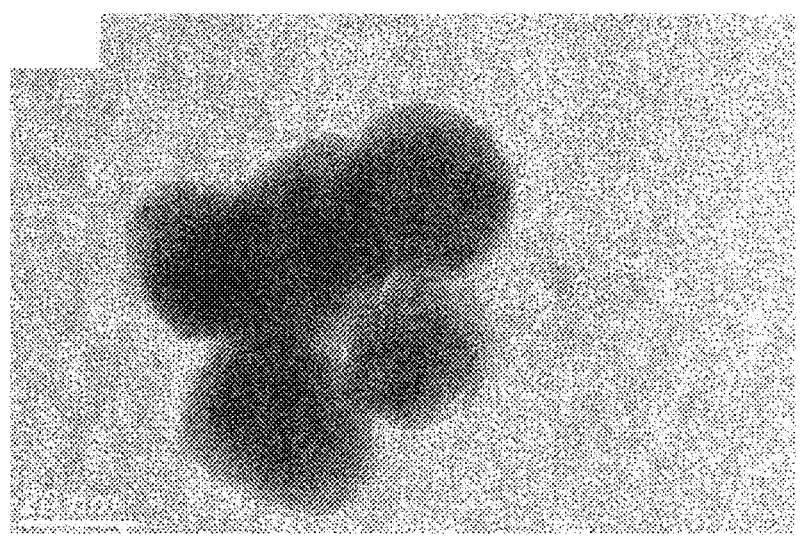

FIGS. 21A-21D shows the TEM images of an asymmetric Janus nanocluster-polymer nanoparticle induced by MGITC at a final concentration of 0.75 μM; FIGS. 21A-21B show asymmetric Janus nanocluster-polymer nanoparticle not stabilized by BSA (The asymmetric Janus nanocluster-polymer nanoparticle was formed without BSA coating due to a low clustering level.), FIGS. 21C and 21D show asymmetric Janus nanocluster-polymer nanoparticle stabilized by BSA. There was no significant difference between the two nanostructures with or without BSA coating. Scale bar: 200 nm as shown in FIGS. 21A and 21C, 50 nm as shown in FIG. 21B, and nm as shown in FIG. 21C.

Figure 22A:
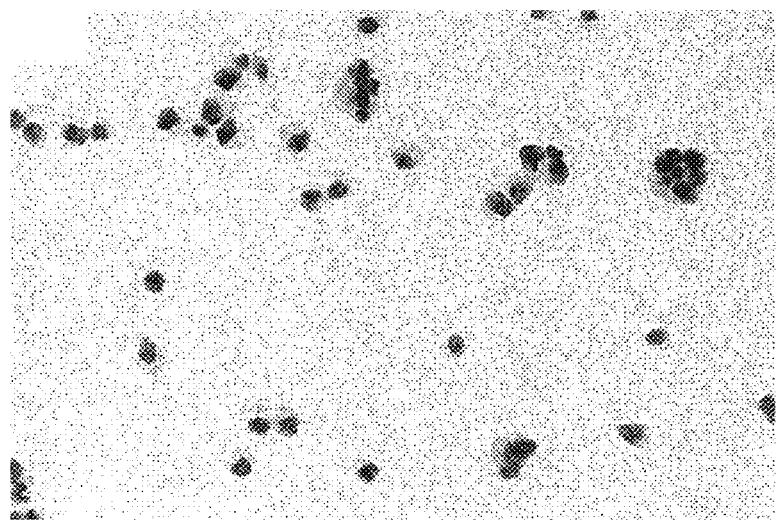
Figure 22B:
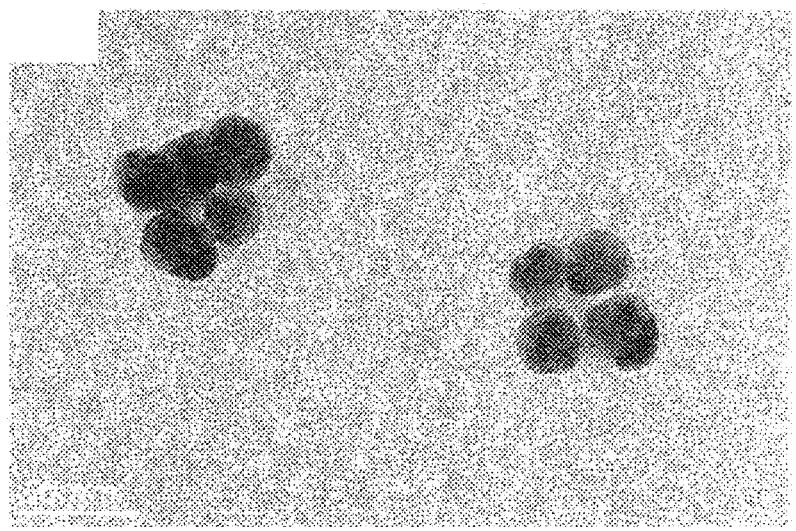
Figure 22C:
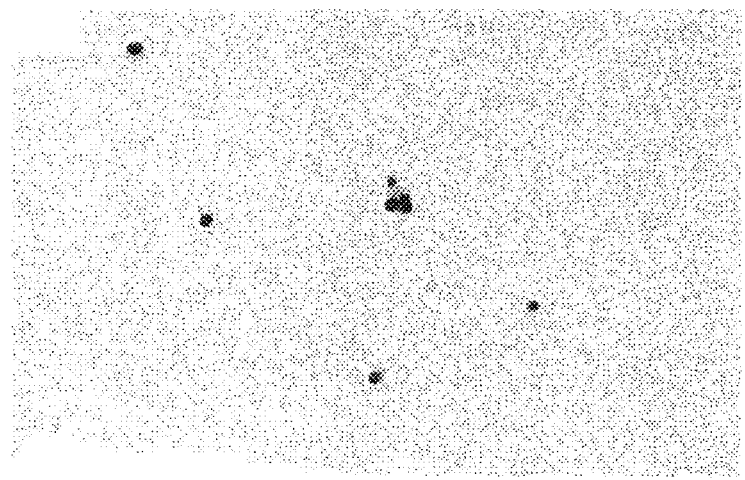
Figure 22D:
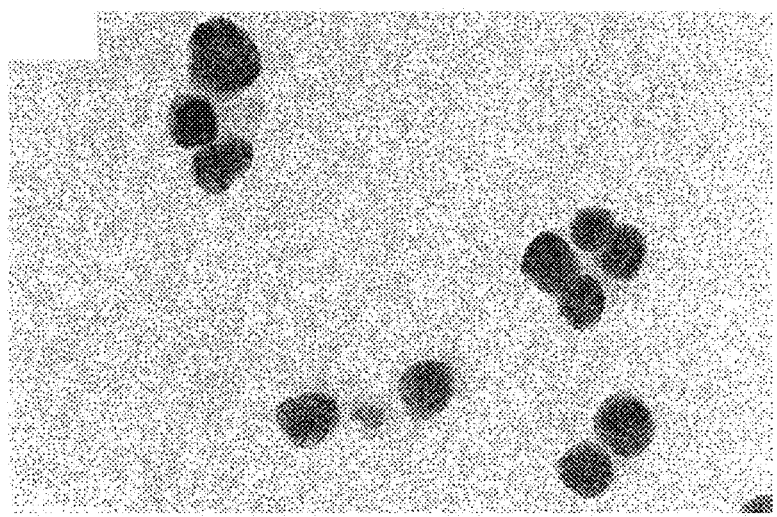

FIGS. 22A-22D shows the TEM images of an asymmetric Janus nanocluster-polymer nanoparticle induced by RBITC at a final concentration of 1.9 μM; FIGS. 22A-22D show asymmetric Janus nanocluster-polymer nanoparticle not stabilized by BSA (The asymmetric Janus nanocluster-polymer nanoparticle was formed without BSA coating due to a low clustering level.), FIGS. 22C and 22D show asymmetric Janus nanocluster-polymer nanoparticle stabilized by BSA. There was no significant difference between the two nanostructures with or without BSA coating. Scale bar: 200 nm as shown in FIGS. 22A and 22C and 20 nm as shown in FIGS. 22B and 22D.

Figure 23A:
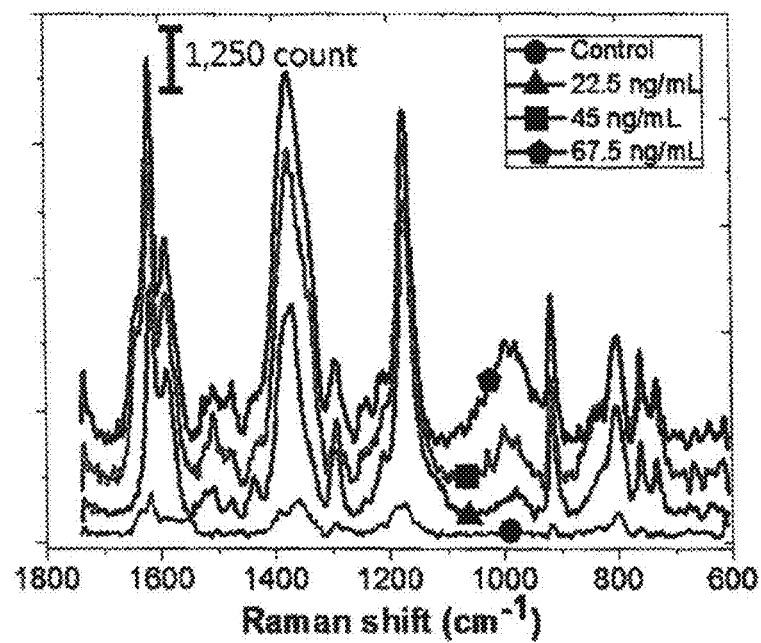
Figure 23B:
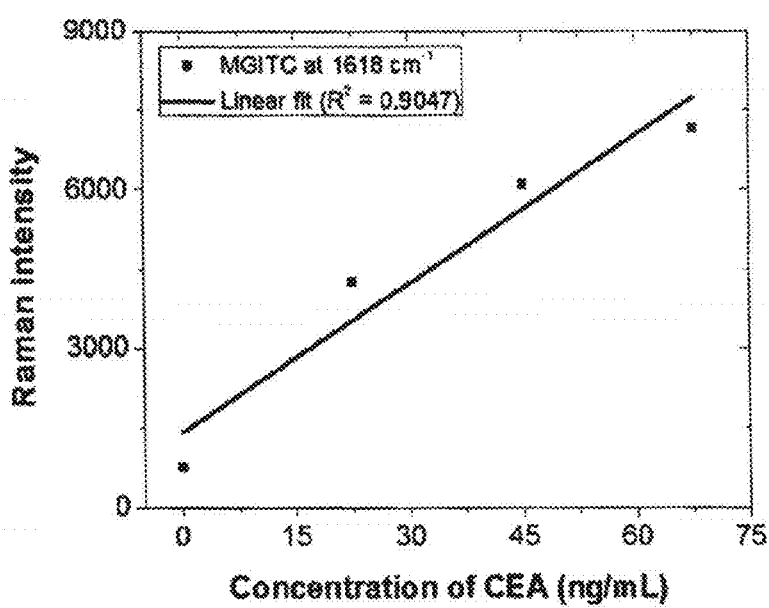

FIGS. 23A-23B shows the Raman spectra and Raman intensity depending on CEA concentration. The SERS peak intensity of an MGITC-induced asymmetric Janus nanocluster-polymer nanoparticle at 1618 $cm^{-1}$ increased linearly with the CEA concentration. $R^2$=0.9047. Control is a CEA-free control group.

Figure 24A:
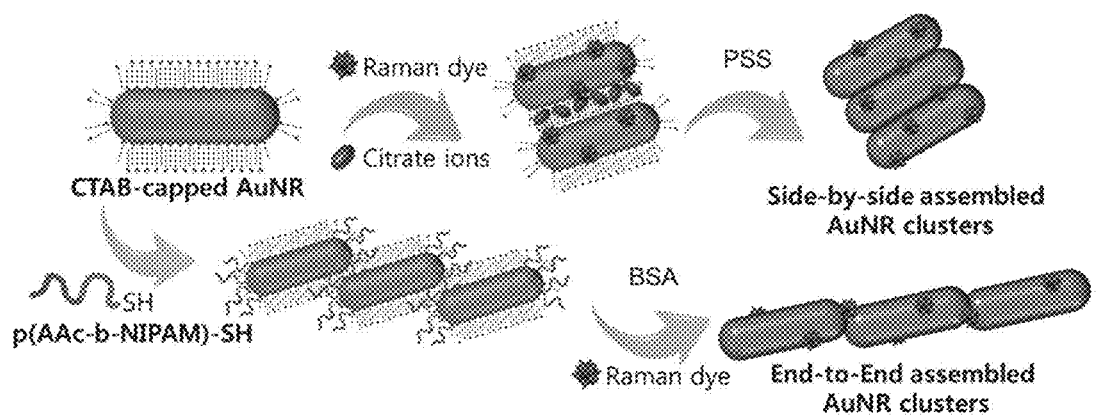
Figure 24B:
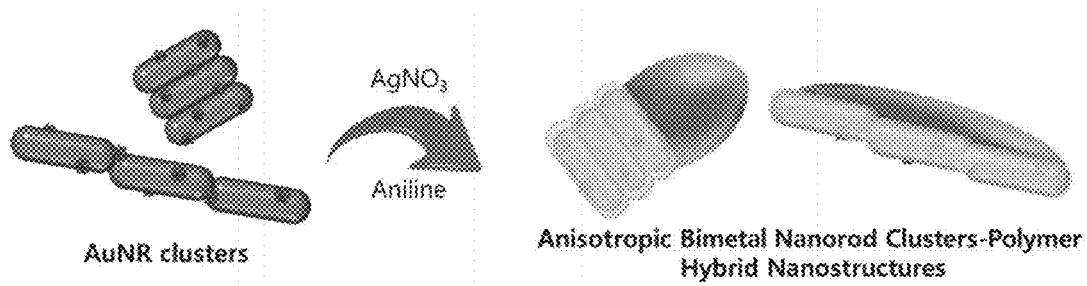
Figure 24C:
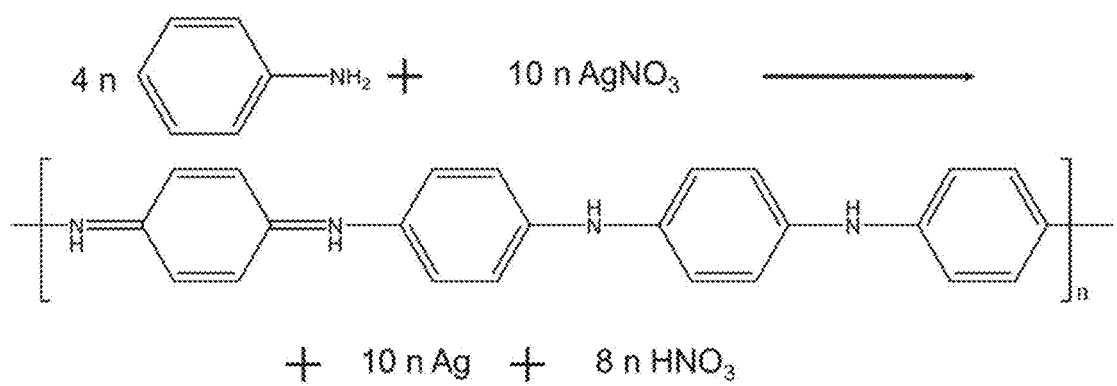
Figure 24D:
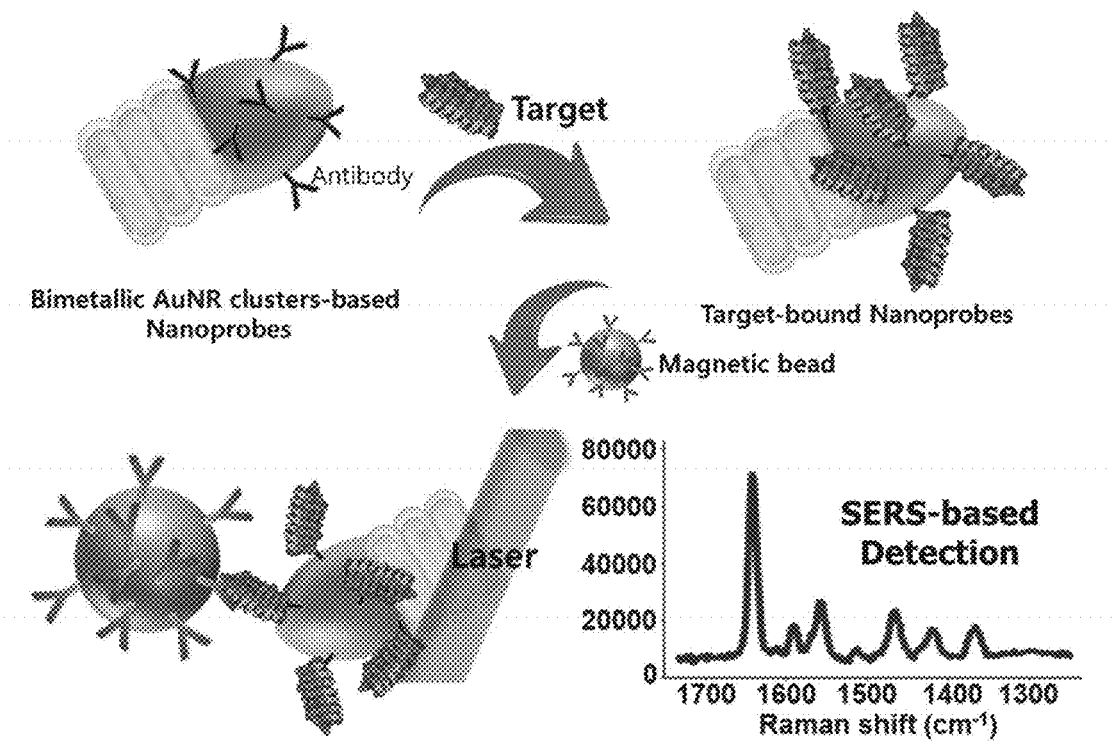

Invention 4:

FIGS. 24A-24D schematically shows the synthesis of an anisotropic side-by-side or end-to-end self-assembled AuNR and a Janus nanostructure thereof and application thereof; FIG. 24A shows controlled assembly of AuNR through electrostatic interaction, FIG. 24B shows synthesis of anisotropic bimetal nanorod cluster-polymer Janus nanostructure using anisotropically self-assembled AuNR cluster as seed, FIG. 24C shows spontaneous oxidation-reduction reaction between aniline monomer and silver nitrate, FIG. 24D shows a method for detecting target material based on surface-enhanced Raman scattering (SERS) using Janus nanostructure.

Figure 25A:
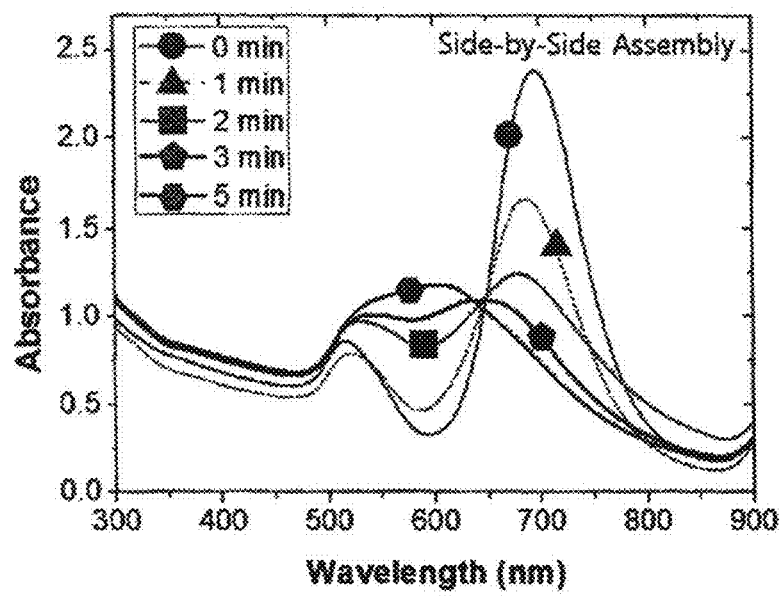
Figure 25B:
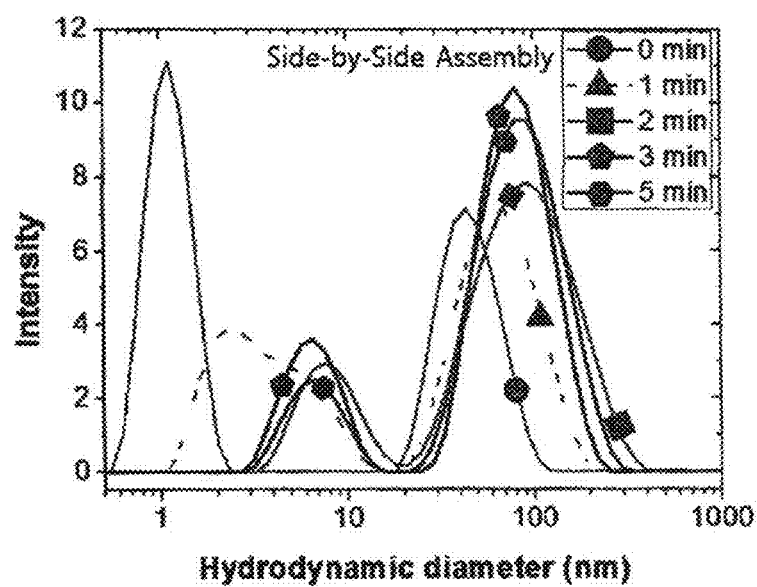
Figure 25C:
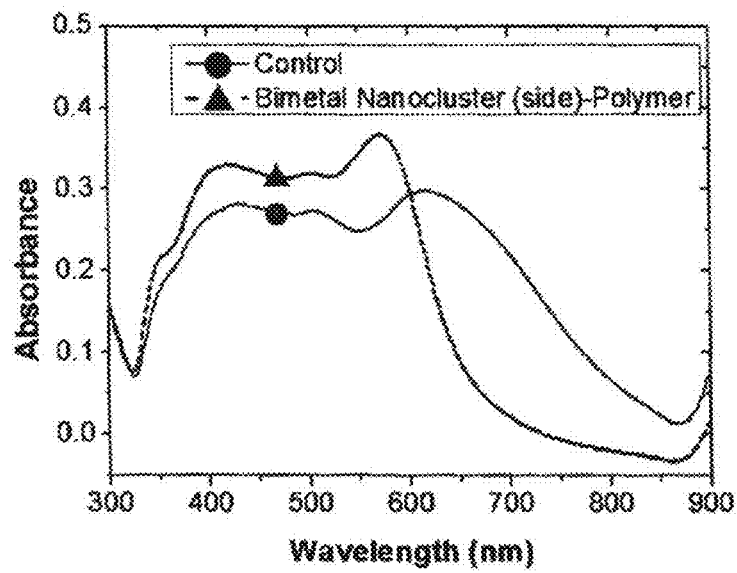
Figure 25D:
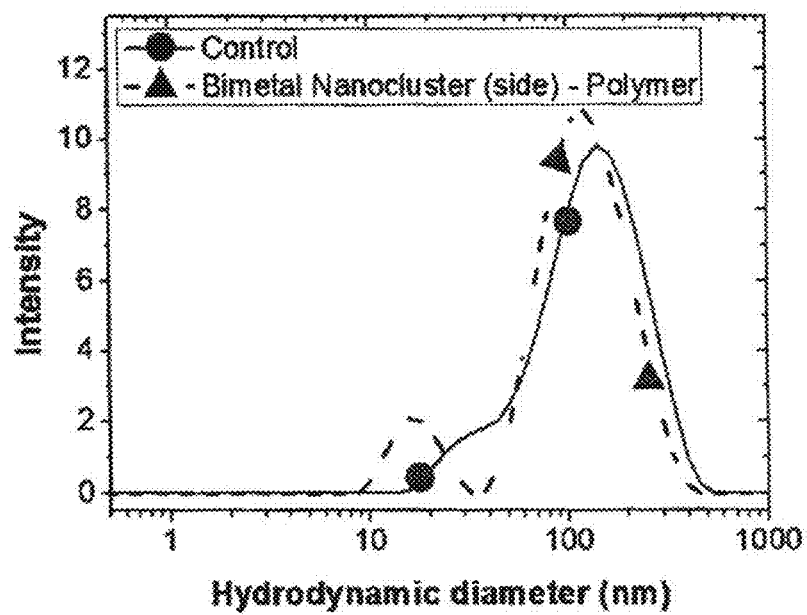

FIGS. 25A-25D shows the UV-Vis absorbance spectra and hydrodynamic diameter of a side-by-side assembled AuNR cluster and an anisotropic Janus nanostructure containing the same; FIG. 25A shows UV-Vis absorbance spectra of side-by-side assembled AuNR cluster with increasing incubation time from 1 minute to 5 minutes, FIG. 25B shows hydrodynamic diameter of side-by-side assembled AuNR cluster with increasing incubation time from 1 minute to 5 minutes, FIG. 25C shows UV-Vis absorbance spectra of anisotropic Janus nanostructure containing side-by-side assembled anisotropic AuNR cluster, FIG. 25D shows hydrodynamic diameter of anisotropic Janus nanostructure containing side-by-side assembled anisotropic AuNR cluster. Control is an AuNR cluster-free bimetal nanorod-polymer Janus nanostructure.

Figure 26A:
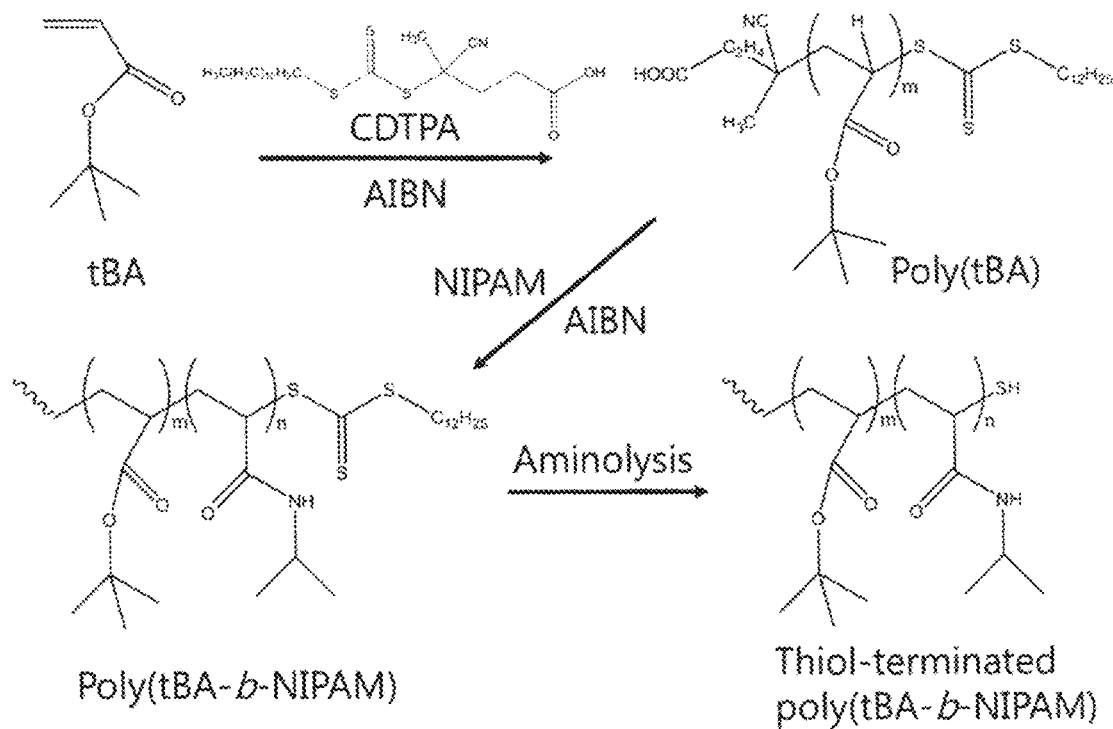
Figure 26B:
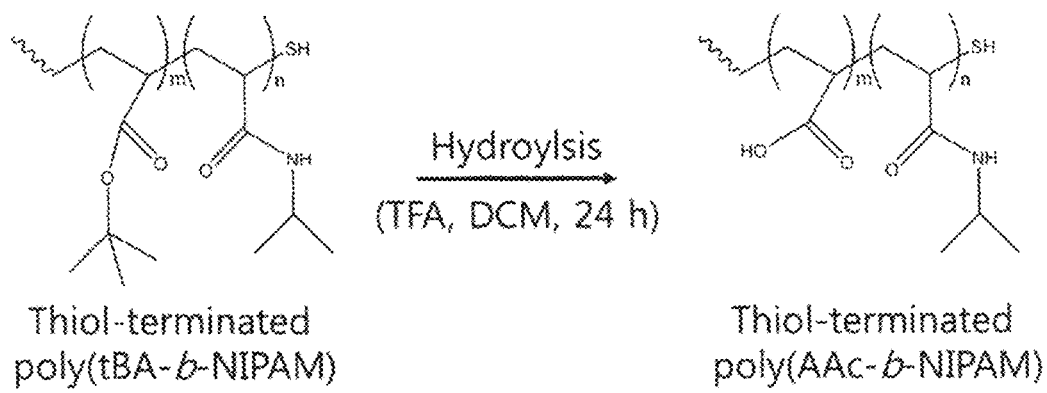

FIGS. 26A-26B schematically shows the synthesis of thiol-terminated poly(tBA-b-NIPAM), as seen in FIG. 26A and poly(AAc-b-NIPAM) as seen in FIG. 26B.

Figure 27A:
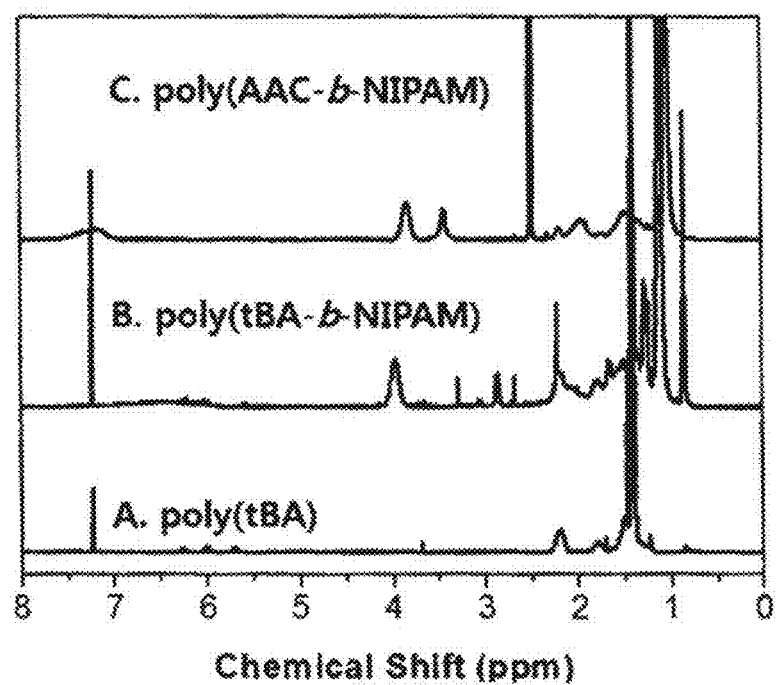
Figure 27B:
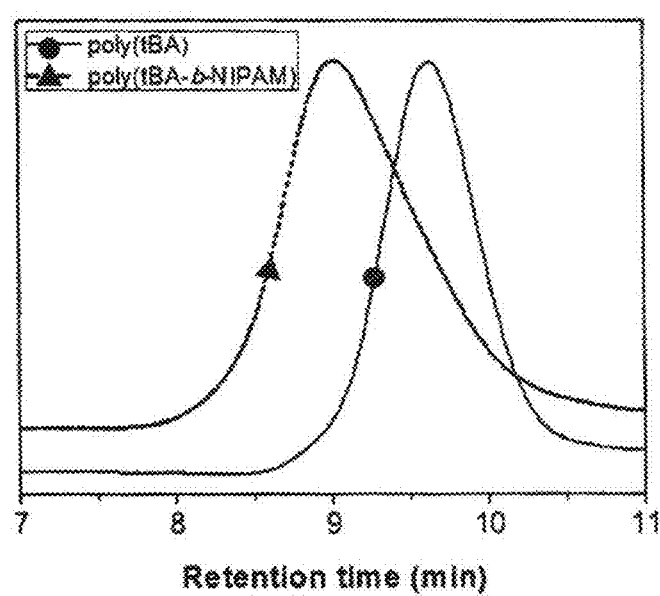
Figure 27C:
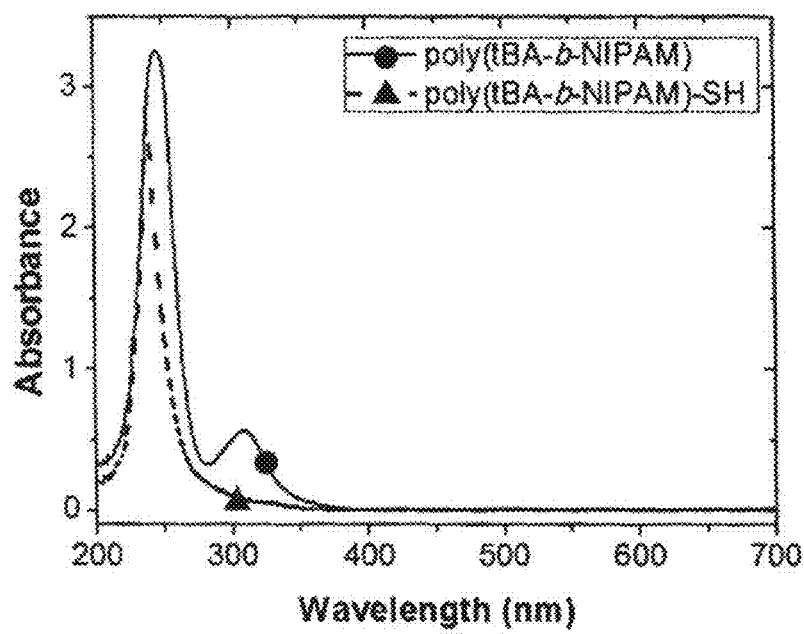
Figure 27D:
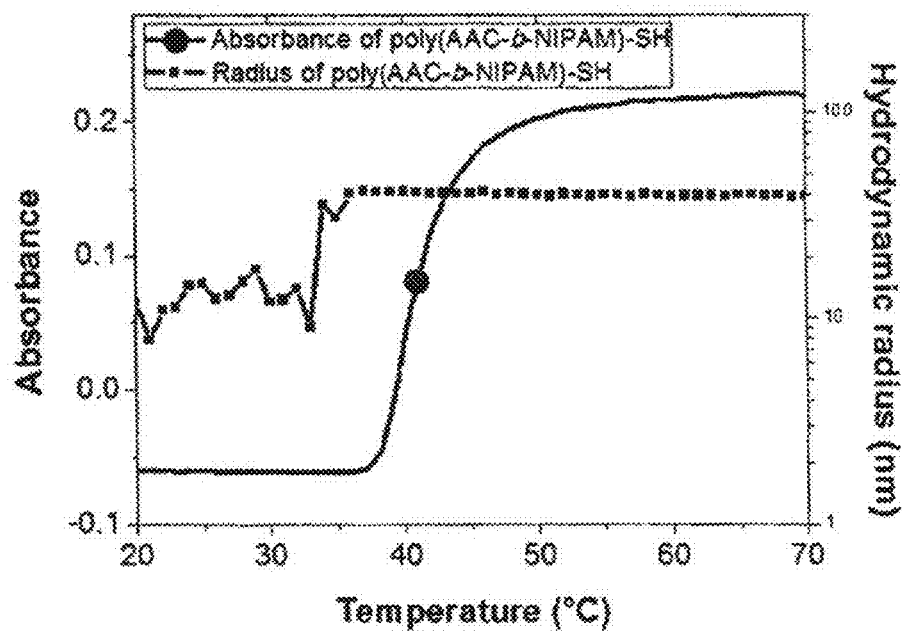

FIGS. 27A-27D first shows FIG. 27A the $^1$H NMR spectra of poly(tBA) and poly(tBA-b-NIPAM) measured in CDCl$_3$ and poly(AAc-b-NIPAM) measured at 400 MHz in DMSO-d$_6$, FIG. 27B which shows the GPC trace of poly (tBA) and poly(tBA-b-NIPAM) depending on retention time, FIG. 27C which shows the UV-Vis absorption spectra of poly(tBA-b-NIPAM) before and after aminolysis and FIG. 27D which shows the intrinsic thermal deformation characteristics of poly(AAc-b-NIPAM) in 0.05 w/v % PBS (10 mM) depending on temperature.

Figure 28A:
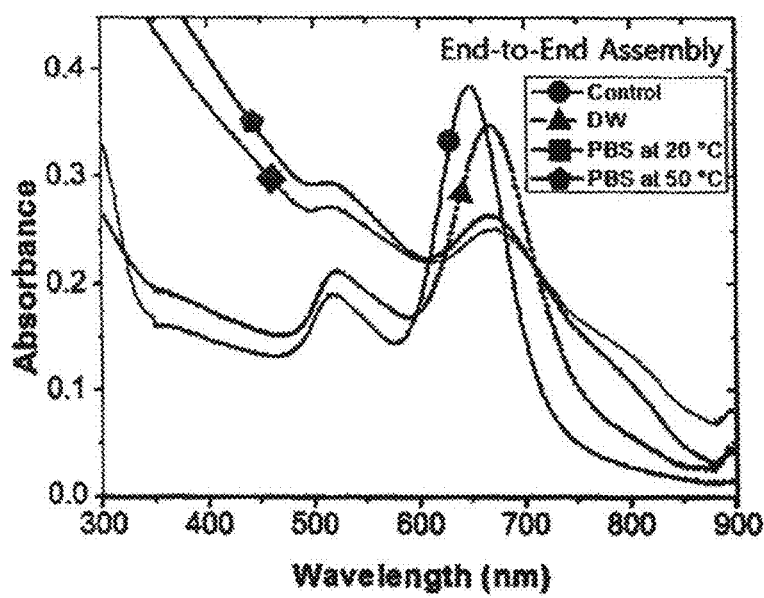
Figure 28B:
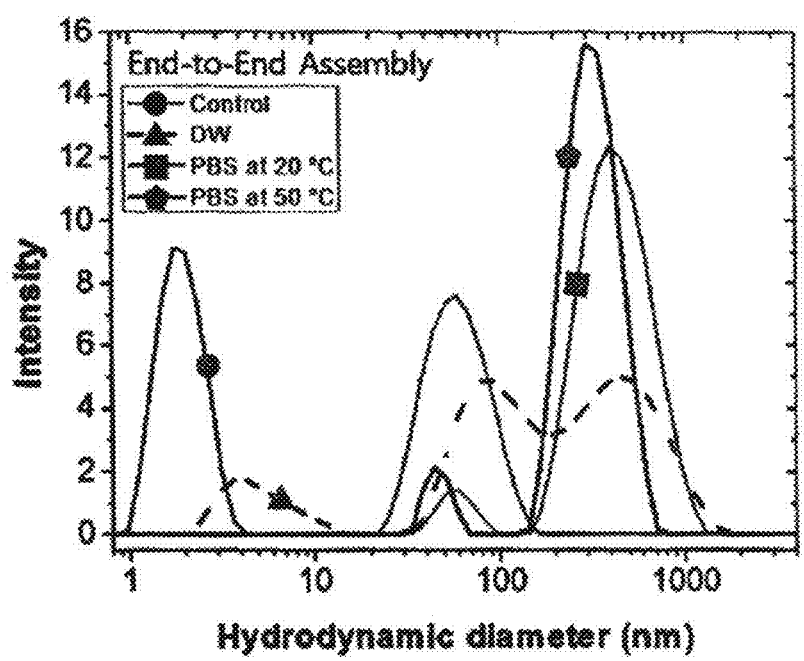
Figure 28C:
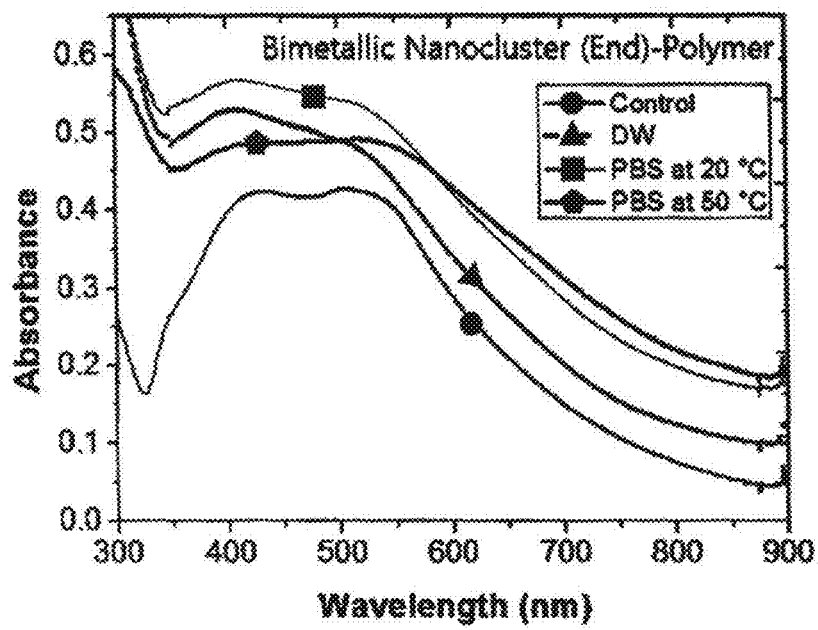
Figure 28D:
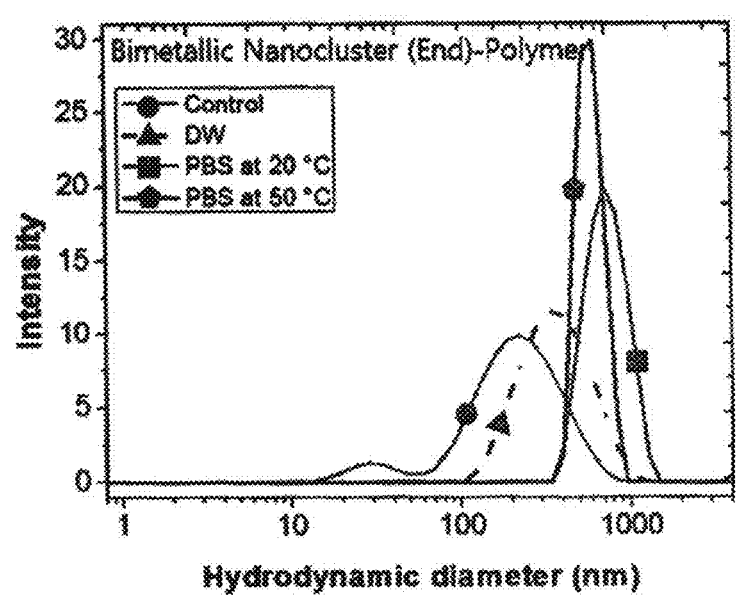

FIGS. 28A-28D shows the UV-Vis absorbance spectra and hydrodynamic diameter of an end-to-end assembled AuNR cluster and an anisotropic Janus nanostructure containing the same; FIG. 28A shows UV-Vis absorbance spectra of end-to-end assembled AuNR cluster in deionized water or PBS at different temperatures, FIG. 28B shows hydrodynamic diameter of end-to-end assembled AuNR cluster in deionized water or PBS at different temperatures, FIG. 28C shows UV-Vis absorbance spectra of anisotropic Janus nanostructure containing end-to-end assembled anisotropic AuNR cluster in deionized water or PBS at different temperatures, FIG. 28D shows hydrodynamic diameter of anisotropic Janus nanostructure containing end-to-end assembled anisotropic AuNR cluster in deionized water or PBS at different temperatures. Control is an AuNR cluster-free bimetal nanorod-polymer Janus nanostructure.

Figure 29A:
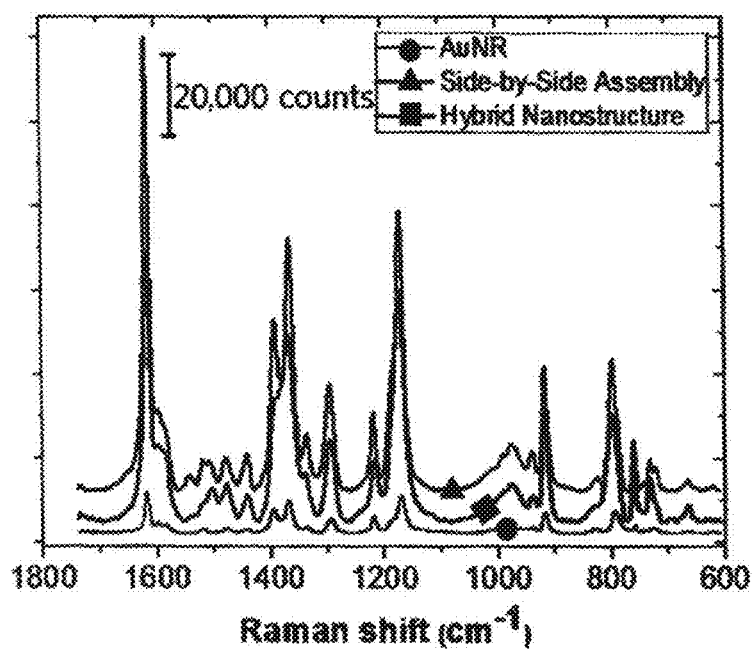
Figure 29B:
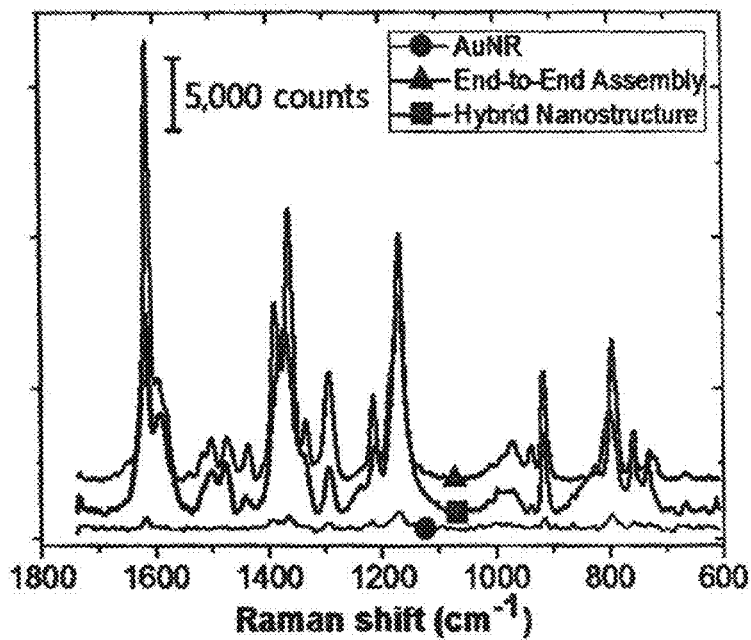

FIGS. 29A-29B first shows FIG. 29A the relative Raman shift of a side-by-side assembled AuNR cluster labeled with $10^{-6}$ M MGITC and an anisotropic Janus nanostructure containing the same in deionized water and FIG. 29B the relative Raman shift of a Janus nanostructure containing an end-to-end assembled AuNR nanocluster in deionized water or PBS at room temperature. Control is an individual AuNR.

Figure 30A:
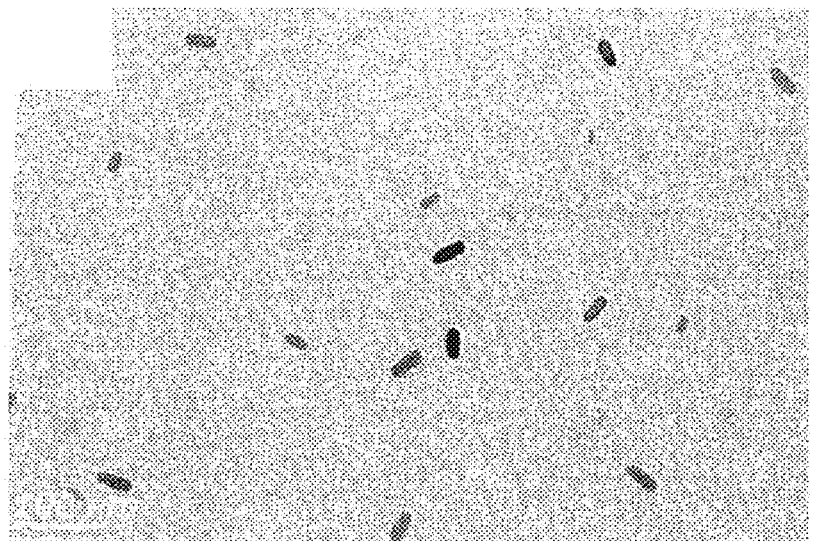
Figure 30B:
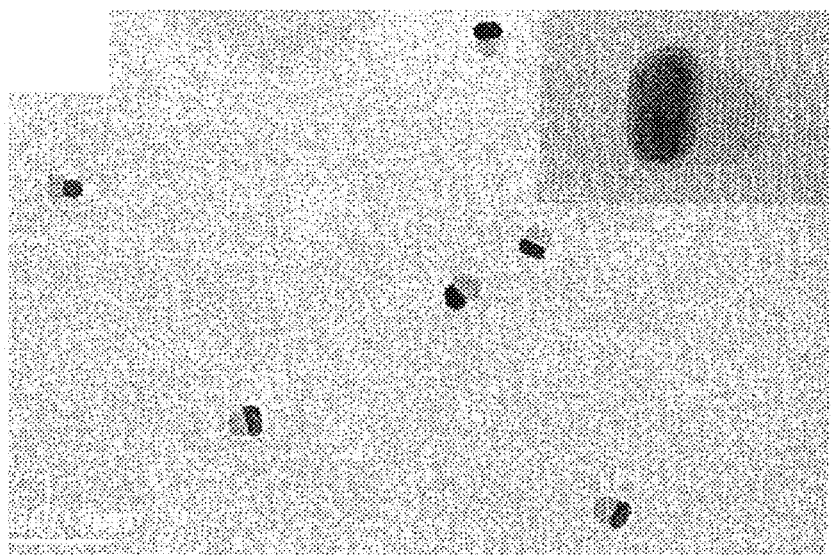
Figure 30C:
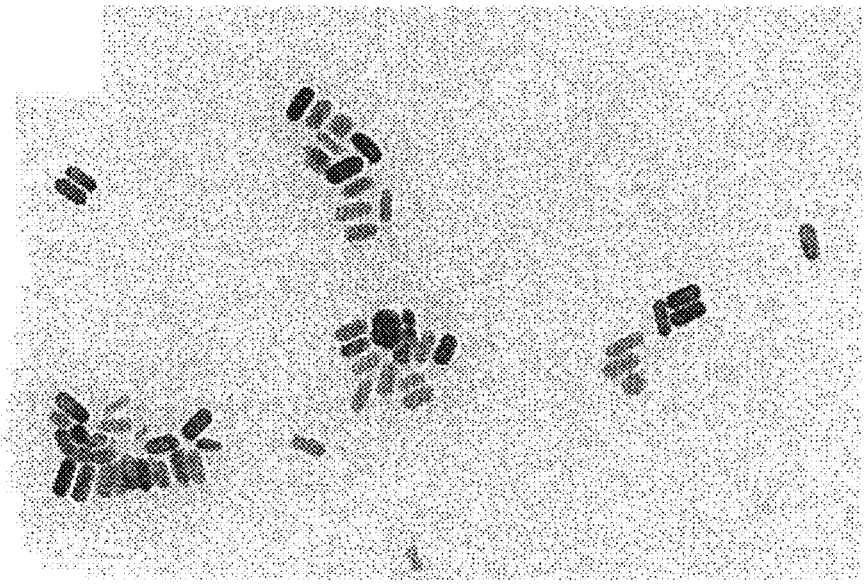
Figure 30D:
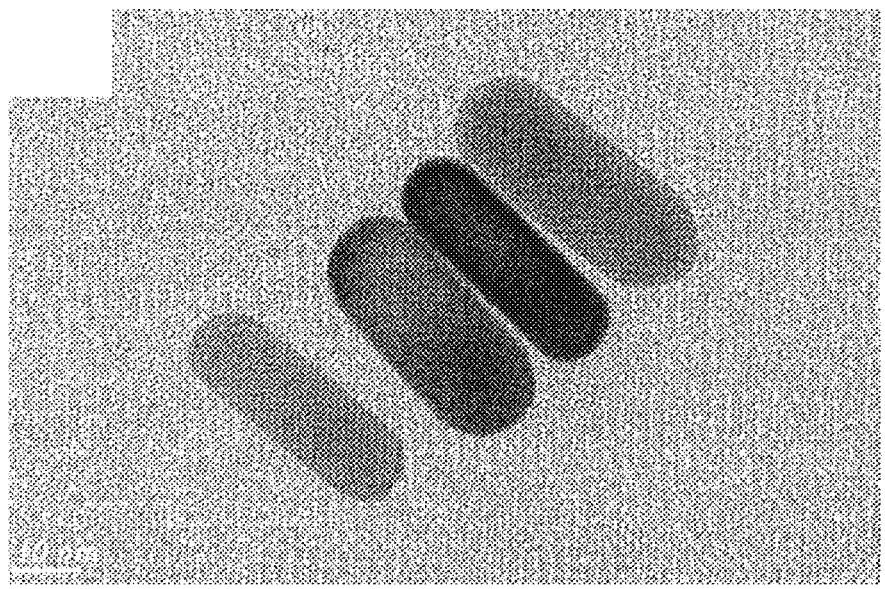
Figure 30E:
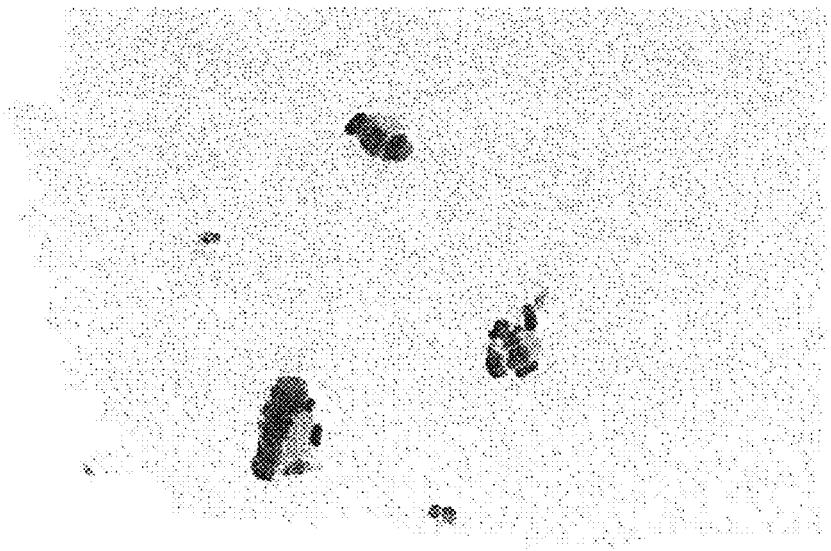
Figure 30F:
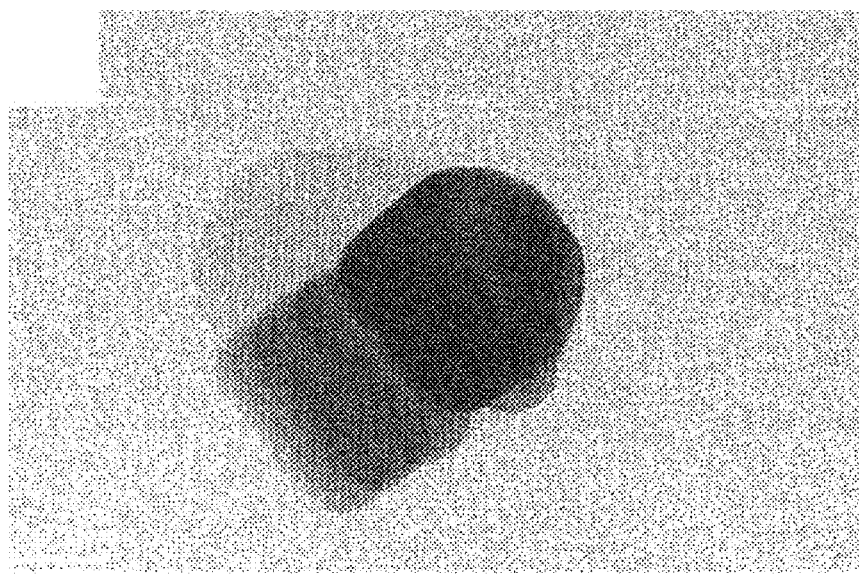

FIGS. 30A-30F shows transmission electron microscopy (TEM) images of nanoparticles; FIG. 30A shows individual AuNR, FIG. 30B shows AuNR cluster-free bimetal nanorod-polymer Janus nanoparticle, FIGS. 30C and 30D show side-by-side assembled AuNR cluster, and FIGS. 30E and 30F show anisotropic Janus nanostructure containing side-by-side assembled AuNR cluster. Scale bars: 100 nm as seen in FIG. 30A, 200 nm as seen in FIGS. 30B, 30C and 30W, 10 nm as shown in FIG. 30D, and 20 nm as shown in FIG. 30F.

Figure 31A:
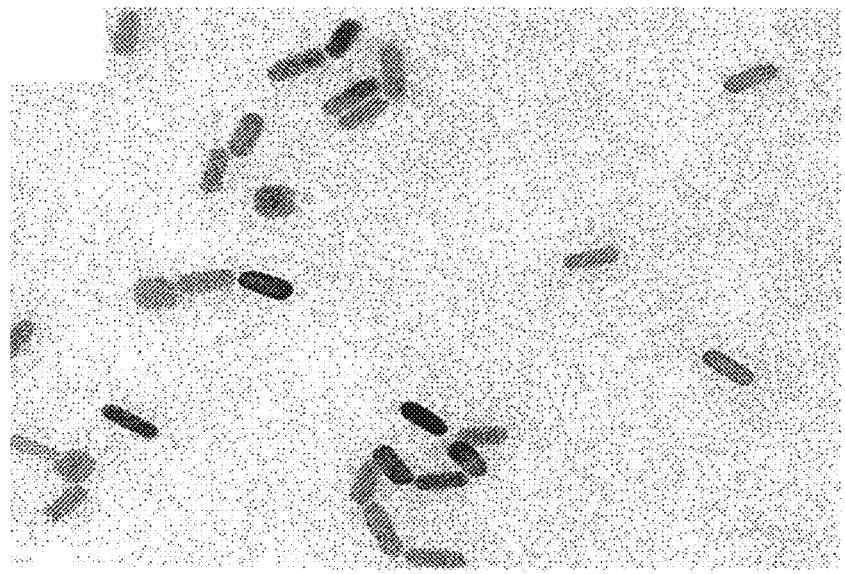
Figure 31B:
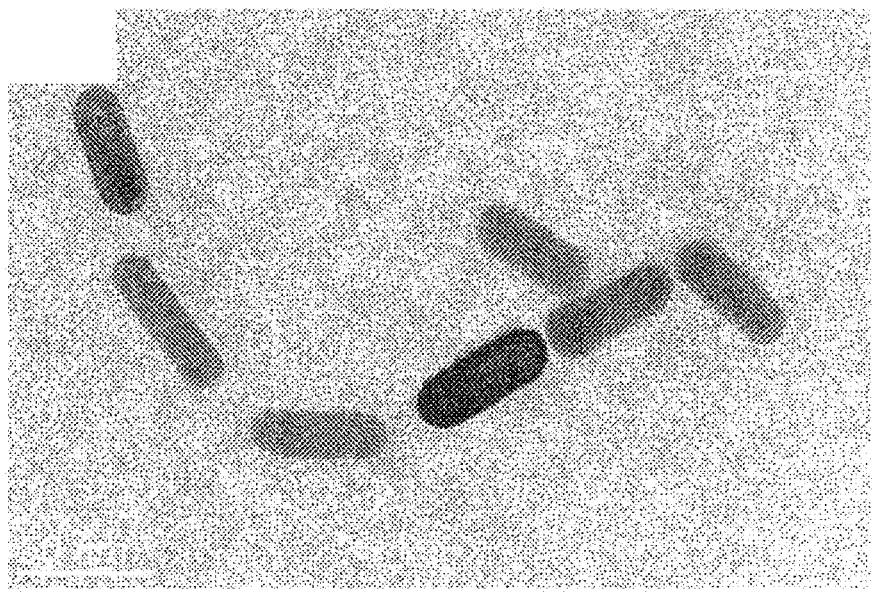
Figure 31C:
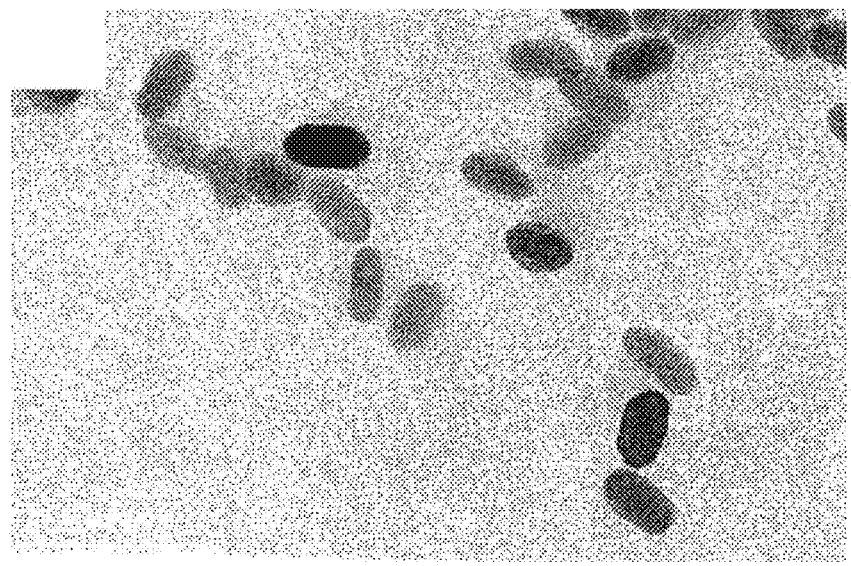
Figure 31D:
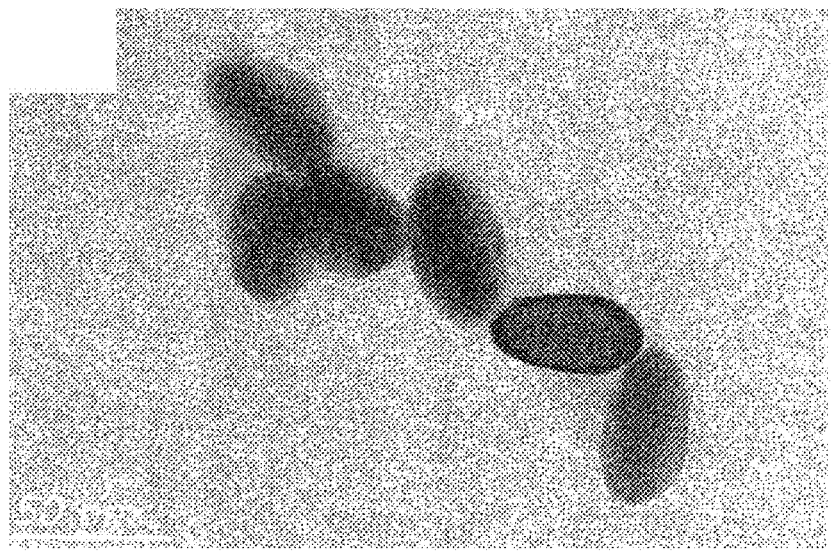

FIGS. 31A-31D show the transmission electron microscopy (TEM) images of nanoparticles; FIGS. 31A and 31B show end-to-end assembled AuNR cluster, and FIGS. 31C and 31D show anisotropic Janus nanostructure containing end-to-end assembled AuNR cluster. Scale bar: 100 nm as shown in FIGS. 31A and 31C and 50 nm as shown in FIGS. 31B and 31D.

Figure 32A:
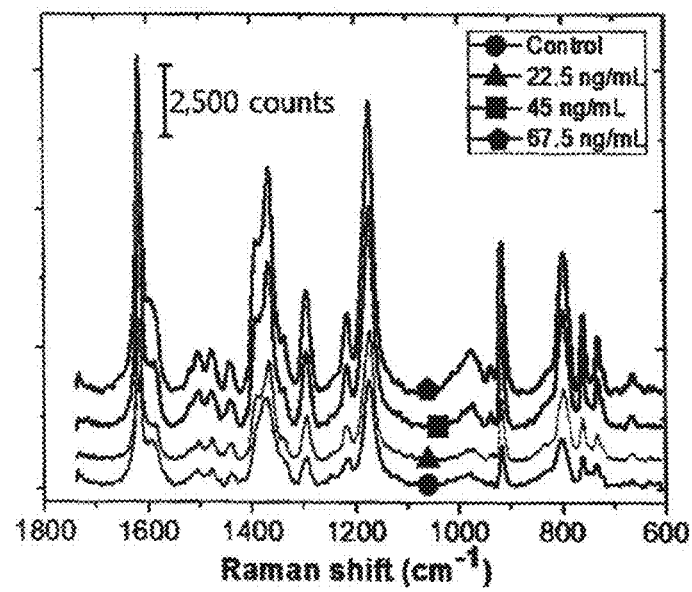
Figure 32B:
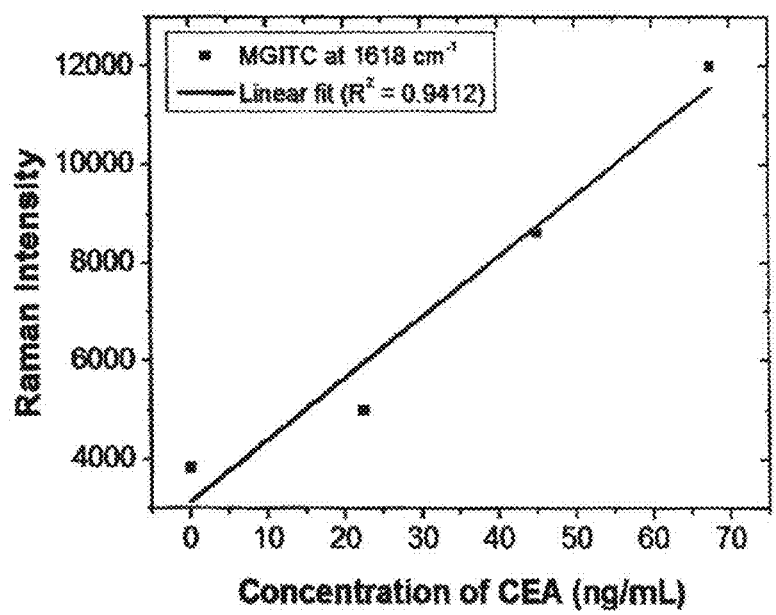

FIGS. 32A and 32B shows the Raman spectra and Raman intensity depending on CEA concentration. The SERS peak intensity of an anisotropic Janus nanostructure containing an MGITC-induced side-by-side assembled AuNR cluster at 1618 cm$^{-1}$ increased linearly with the CEA concentration. $R^2=0.9412$. Control is a CEA-free control group.

DETAILED DESCRIPTION OF THE INVENTION

Hereinafter, specific examples are presented to help understanding the present disclosure. However, the following examples are given only as examples of the present disclosure and it will be obvious to those of ordinary skill in the art that various changes and modifications can be made within the scope of the present disclosure. Also, it will be obvious that such changes and modifications belong to the scope of the appended claims. The references cited in the present disclosure are incorporated herein by reference.

Invention 1

<Example 1> Synthesis of Bimetal-Polymer Janus Structure

A citrate-capped gold nanoparticle (AuNP) was synthesized by citrate reduction. Specifically, a stock solution of gold(III) chloride hydrate (HAuCl$_4$·3H$_2$O) was added to 100 mL of deionized water to a concentration of 0.01%. After heating the solution under stirring, 1.5 mL of a 1% sodium citrate solution was added to the boiling solution while stirring continuously. The solution turned red within 5 minutes, which is indicative of reduction of gold ion. The reaction was conducted further for 20 minutes. Then, the solution was cooled to room temperature. A bimetal-polymer Janus nanostructure consisting of a bimetal Au core-Ag shell part and a poly(aniline) part was prepared through surface-templated polymerization based on oxidation-reduction. Specifically, 15 mL of the citrate-capped AuNP solution was concentrated by centrifuging at 10,000 rpm for 15 minutes and the supernatant was removed. Aniline and SDS were dissolved in 7.5 mL of deionized water to final concentrations of 5 mM and 0.9 mM, respectively. After adding the concentrated AuNP to the solution and vortexing shortly, 2.5 mL of a silver nitrate solution was added and mixed to a final concentration of 2.5 mM. By conducting reaction under a dark condition at room temperature for 24 hours without stirring, a bimetal consisting of an Au seed (first metal) and Ag (second metal) surrounding the seed metal was synthesized. A polymer part was formed by eccentrically depositing poly(aniline) on only one side of the bimetal by incubating the reaction solution overnight in a 3.6 mM SDS solution. A bimetal-polymer Janus nanostructure consisting of a bimetal nanocluster part and a polymer part was prepared by purifying the resulting solution by centrifuging at 8,000 rpm for 10 minutes and resuspending in a 3.6 mM SDS solution to prevent aggregation.

Figure 1A:
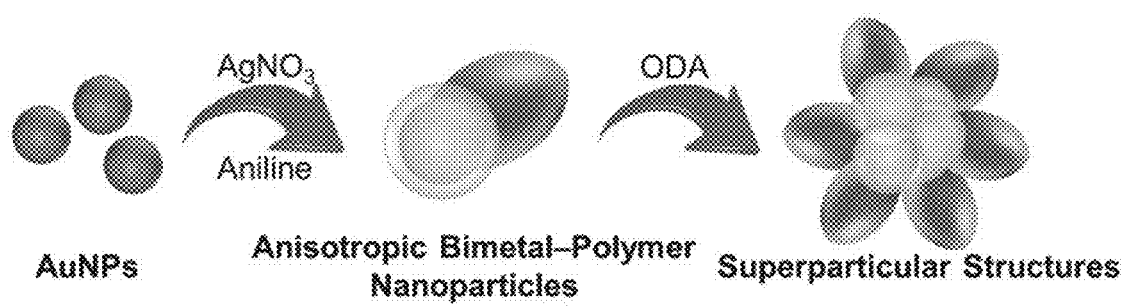
FIGS. 1A-1C schematically show a bimetal-polymer Janus nanostructure, a self-assembled Janus nanostructure cluster thereof, an experimental method for preparing a superparticular structure thereof and an experimental method for application to SERS-based biosensing.
Figure 1B:
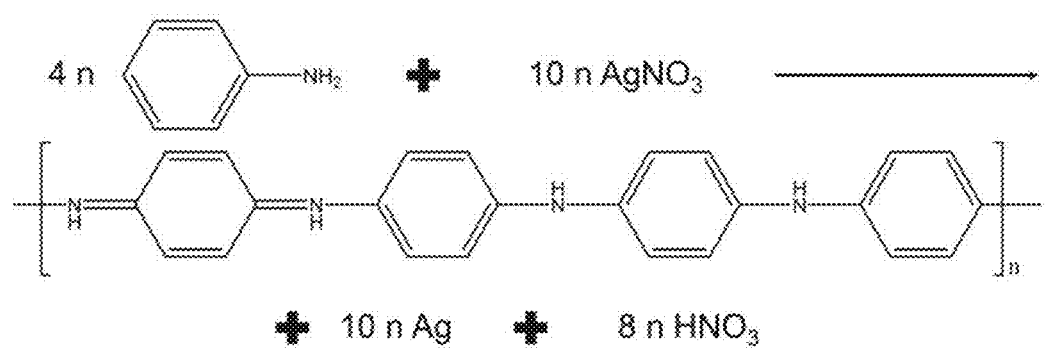

<Example 2> Synthesis of Self-Assembled Bimetal-Polymer Janus Nanostructure Cluster Superparticular Structure Consisting of Bimetal Nanocluster Core and Polymer Shell Located Radially Around the Core Two Raman reporters, RBITC (rhodamine B isothiocyanate) and MGITC (malachite green isothiocyanate), were selectively introduced to a bimetal-polymer Janus nanocluster part and directional self-assembly into a superparticular structure was achieved through noncovalent interaction. A superparticular structure was prepared as the bimetal in the bimetal-polymer Janus nanostructure of Example 1 was self-assembled through hydrophobic interaction to form a bimetal nanocluster core and the polymer part extended in a direction opposite to the bimetal nanocluster and was located radially to form a polymer shell (as seen in FIG. 1A. Specifically, 1 mL of the bimetal-polymer Janus nanoparticle solution was centrifuged at 10,000 rpm for 10 minutes and then transferred to 1 mL of deionized water. The colloid solution was mixed with freshly prepared RBITC or MGITC at a concentration of $10^{-5}$-$10^{-8}$ M and then incubated for 2 hours, respectively. In addition, in order to covalently bond ODA (octadecylamine) containing a long hydrophobic alkyl chain to the bimetal cluster part through selective functionalization, 0.46 mM EDC (1-ethyl-3-(3-dimethylaminopropyl)carbodiimide) was added to the nanoparticle solution to activate the residual carboxyl group on the bimetal cluster part, followed by stirring for 1 hour. After slowly adding ODA dissolved in THF (tetrahydrofuran) to the reaction solution to 0.742 µM, 1.484 µM or 2.968 µM, the mixture was stirred for 1 hour to form amide bonding between the carboxyl group and the amine group of the ODA. Finally, the reaction solution was centrifuged at 10,000 rpm for 10 minutes and then resuspended in deionized water or PBS (phosphate-buffered saline) for later experiment.

<Example 3> Synthesis of Magnetic Nanoparticle (MNP) and Magnetic Bead Through Electrohydrodynamic (EHD) Jetting A magnetic nanoparticle (MNP) was synthesized using an iron chloride precursor. An iron oxide nanoparticle (Fe$_3$O$_4$) was prepared by chemical coprecipitation using a 1:2 (molar ratio) mixture of Fe$^{2+}$ and Fe$^{3+}$ in an aqueous ammonia solution as a precipitating agent. Specifically, 0.86 g of iron(II) chloride (FeCl$_2$) tetrahydrate and 2.35 g of iron(III) chloride (FeCl$_3$) were mixed by stirring in 40 mL of deionized water and degassed with nitrogen gas for 30 minutes. After raising temperature to 80° C. and adding 5 mL of ammonium hydroxide (NH₄OH) using a syringe, the mixture was heated for 30 minutes. After adding 1 g of citric acid to a reaction flask and heating to 90° C., the reaction solution was stirred for 90 minutes. Finally, the $Fe_3O_4$ magnetic nanoparticle (MNP) was washed twice with deionized water under a static magnetic field of hundreds of Gauss. Also, a magnetic bead was prepared by concentrating a small aliquot of a MNP solution using a magnetic field, adding to a polymer solution and conducting electrohydrodynamic (EHD) jetting. 4.5 w/v % of poly(acrylamide-co-acrylic acid) (poly(AAm-co-AA)) was prepared in a 3:1 (volume ratio) mixture of deionized water and ethylene glycol and the concentrated MNP was uniformly suspended in the polymer solution. For electrohydrodynamic (EHD) dispersion, the suspension of the dispersed MNP was put in a 1.0-mL syringe (BD, Franklin Lakes, USA) having a 23-gauge stainless steel capillary tube. To achieve a stable Taylor cone and a cone-jet mode, an optimized viscosity was obtained by dissolving the polymer in a viscous solvent such as ethylene glycol without increasing the polymer concentration. The microsyringe pump KDS-100 (KD Scientific, Inc., USA) allowing the flow of the MNP suspension at a constant rate was equipped at the syringe. A 0.018-mm thick aluminum foil (Fisherbrand; Thermo Fisher Scientific, USA) was used as a collecting plate. A high voltage was applied between the capillary tube connected to an anode and the aluminum foil connected to a cathode using the high-voltage power source NNC HV 30 (Nano NC, Korea). The distance between the two electrodes was 20-25 cm. The high voltage was maintained at 15-20 kV and the flow rate of the two solutions was maintained at 0.08-0.15 mL/hour. During the EHD jetting, the single-phase Taylor cone, jet stream and jet break-up were visualized and captured using a high-resolution digital camera (D-90, Nikon Corporation, Japan). After the EHD jetting, the formed magnetic bead was thermally crosslinked overnight at 175° C. Finally, the magnetic bead in the form of a powder was collected by scraping from the foil and used for the following experiments.

<Example 4> Characterization of Bimetal-Polymer Janus Nanoparticle and Superparticular Structure The UV-Vis spectra of the bimetal-polymer Janus nanoparticle were obtained in a wavelength range of 300-900 nm using a UV-Vis spectrophotometer (UV-1800, Shimadzu, Japan) in a single scan mode with a medium scan spped at room temperature with a fixed slit width of 1 nm. The baseline was calibrated using two cells filled with deionized water. The hydrodynamic diameter and size distribution of the colloid solution were characterized by dynamic light scattering (DLS) (Zeta-sizer Nano ZS90, Malvern Instruments, UK) equipped with a Ne—He laser at a wavelength of 633 nm and a maximum output power of 5 mW as a light source at a scattering angle of $90^2$. The temperature was controlled to 25° C. After diluting the sample 2-fold with deionized water at a volume ratio of 1:1, the average size was measured for at least 20 scan cycles. In addition, the zeta potential (ξ-potential) was measured for characterization of surface charge in deionized water. The individual AuNP, the bimetal-polymer Janus nanoparticle and a superparticular structure thereof were analyzed by transmission electron microcopy using JEM-2100F FE-STEM (JEOL, Germany) operating at an accelerating voltage of 80-200 kV. The sample was deposited on a 400-mesh copper grid with ultrathin carbon coating (Ted Pella, Inc., USA). The average diameter, size distribution and surface morphology were measured by scanning electron microscopy (SEM) (VEGA-SB3, TESCAN, Czech Republic) operating at 0.5-30 kV with a focused beam. A small amount of the nanoparticle solution was placed on a silicon wafer and dried at room temperature. The sample was coated with a thin conductive platinum layer using a coater (K575X Turbo Sputter Coater, Emitech Ltd., UK). The average particle size was analyzed for about 50-100 particles randomly selected from the TEM and SEM images using the ImageJ software developed by the National Institutes of Health (USA). All SERS measurements were performed using a Renishaw inVia Raman microscope system equipped with a Renishaw He—Ne laser operating at a wavelength (A) of 632.8 nm in response to a stimulation source having a laser output of 12.5 mW. The Rayleigh line was removed from the collected SERS spectra using a holographic notch filter located in the collection path. Raman scattering was collected using a charge-coupled device (CCD) camera at a spectral resolution of 1 cm⁻¹ and all the SERS spectra were calibrated to the 520 cm⁻¹ silicon line. The colloid solution of the RBITC- or MGITC-labeled nanostructure was put in a small glass capillary tube (Kimble Chase, plain capillary tube, soda-lime glass, inner diameter: 1.1-1.2 mm, wall thickness: 0.2±0.02 mm, length: 75 mm). A 20× objective lens was used to focus the laser spot on the glass capillary tube in a wavelength range of 608-1738 cm⁻¹. The SERS spectra were collected for 1 second of exposure time.

The hydrodynamic diameter and zeta potential of the nanoparticles are shown in Table 1.

TABLE 1

|  | AuNP | ABP NP* | Superparticular nanostructure | ABP NP with RB | ABP NP with MG | Superparticular nanostructure with RB | Superparticular nanostructure with MG |
|---|---|---|---|---|---|---|---|
| Hydrodynamic diameter (nm) | 30.1 ± 0.5 | 62.8 ± 2.3 | 266.3 ± 6.0 | 122.1 ± 2.4 | 112.0 ± 15.9 | 450.1 ± 3.1 | 401.1 ± 10.0 |
| ξ-potential (mV) | −29.5 ± 0.7 | −28.0 ± 0.6 | −11.2 ± 0.9 | −32.2 ± 0.2 | −37 ± 1.1 | −5.9 ± 0.2 | −9.8 ± 0.2 |

*ABP NP (anisotropic bimetal-polymer nanoparticle): bimetal-polymer Janus nanostructure.

Figure 2A:
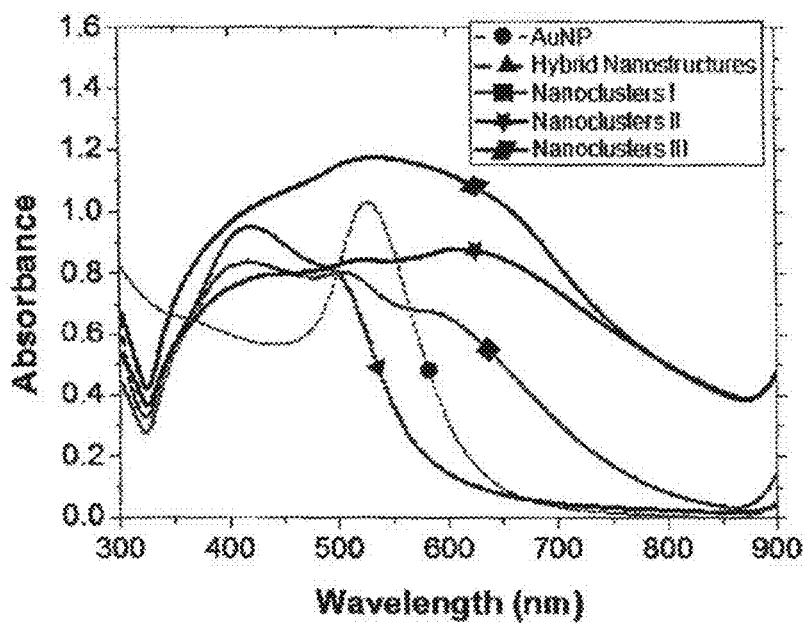
FIGS. 2A-2D show the UV-Vis absorbance and hydrodynamic diameter of an Au nanoparticle, a bimetal-polymer Janus nanostructure, a self-assembled Janus nanostructure cluster thereof and a superparticular structure thereof.
Figure 2B:
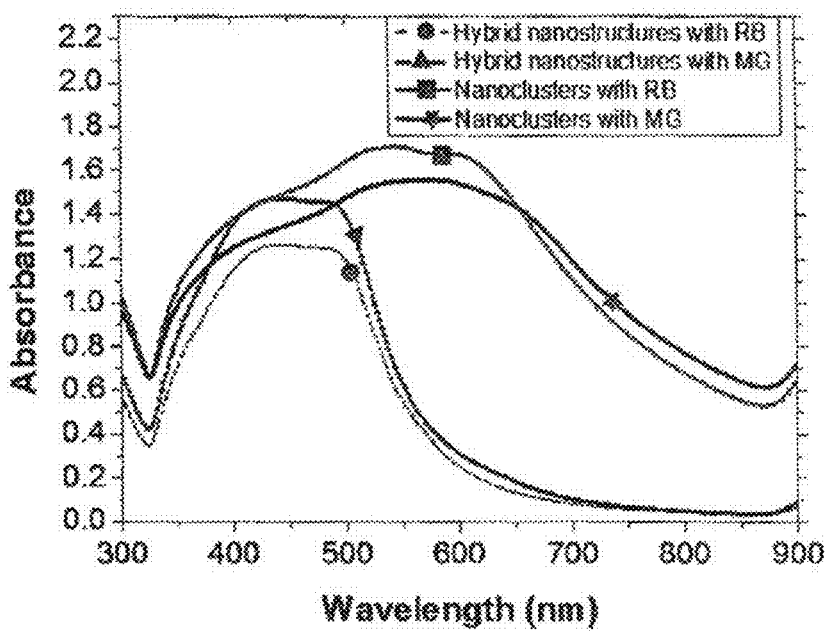
Figure 2C:
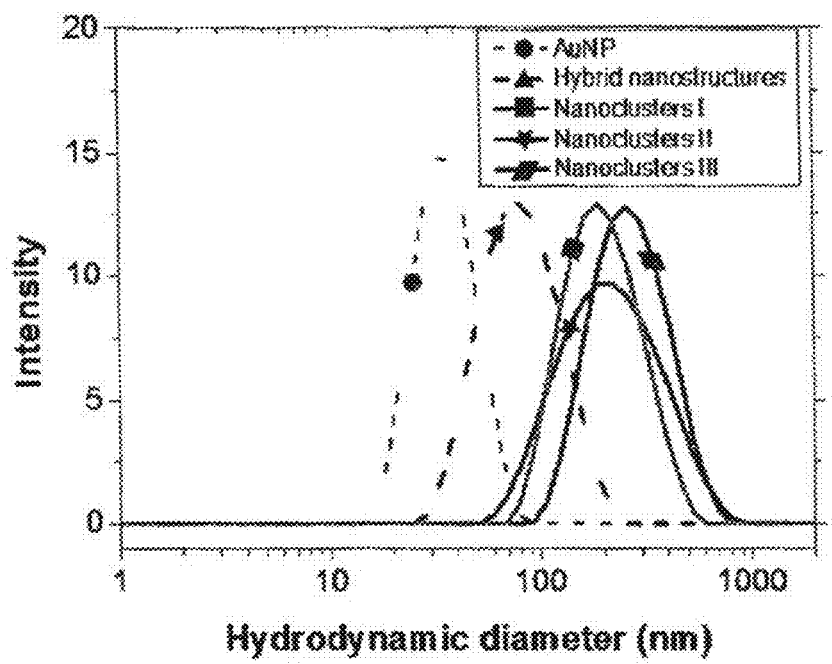
Figure 2D:
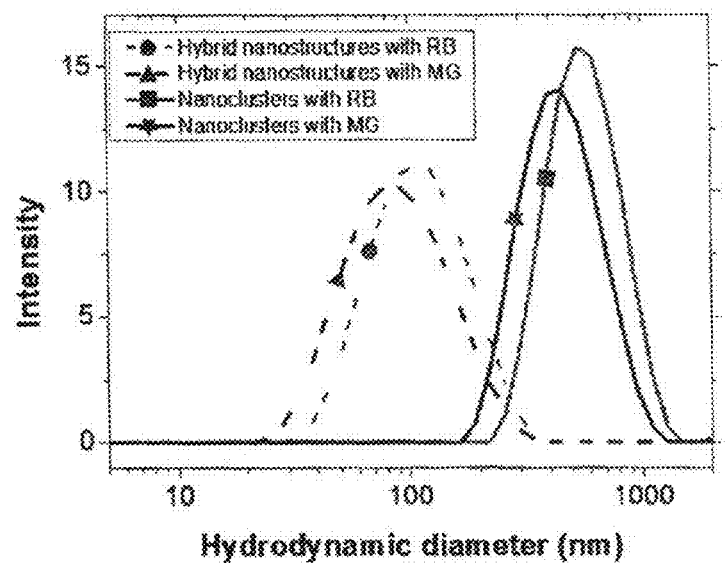

FIGS. 2A-2D show the UV-Vis absorbance and hydrodynamic diameter of the AuNP, the bimetal-polymer Janus nanoparticle and the self-assembled bimetal-polymer Janus nanostructure cluster superparticular structure. As seen from FIG. 2A, the UV-Vis absorption peak of the AuNP appeared at 520 nm. After the synthesis of the bimetal-polymer Janus nanostructure, news absorption peaks appeared in the range from 410 nm to 490 nm and the Au absorption peak was blue-shifted to 480 nm, suggesting the presence of the Au core-Ag shell bimetal nanocluster. This change in plasmon absorption was consistent with the color change of the colloid solution from red to brown. In addition, due to the plasmon absorption bands of the aggregated metal nanostructure, an additional peak appeared at 650 nm after the directional self-assembly into the superparticular structure. FIG. 2B shows the UV-Vis absorption spectra of the RBITC-labeled or MGITC-labeled bimetal-polymer Janus nanoparticle and the Janus nanocluster superparticular structure of the self-assembled bimetal-polymer thereof when $10^{-6}$ M Raman dye and 2.968 µM ODA were added, respectively. Due to the low concentration of the introduced Raman reporter, there was no significant difference in the UV-Vis absorption spectrum in the presence or absence of the Raman reporter. However, after the absorption of the Raman dye by the bimetal nanocluster part, broad peaks relevant with the UV-vis absorption wavelengths of RBITC and MGITC appeared in the range from 410 nm to 500 nm. Also, as seen from FIG. 2C and Table 1, the average diameter of the Au nanoparticle and the bimetal-polymer Janus nanostructure was 30.1±0.5 nm and 62.8±2.3 nm, respectively, and the average diameter of the superparticular structure with different clustering levels was 168.3±1.3 nm, 192.4±2.4 nm and 266.3±6.0 nm. The zeta potential value of the Au nanoparticle, the bimetal-polymer Janus nanostructure and the self-assembled bimetal-polymer Janus nanostructure cluster superparticular structure thereof in deionized water was −29.5±0.7 mV, −28.0±0.6 mV and −11.2±0.9 mV, respectively. It can be seen that ODA was bound well to the bimetal cluster part through amide coupling because the surface charge of the bimetal-polymer Janus nanostructure cluster superparticular structure was greatly decreased. FIG. 2D shows the hydrodynamic diameter of the RBITC-labeled or MGITC-labeled bimetal-polymer Janus nanostructure and the bimetal-polymer Janus nanostructure cluster superparticular structure thereof. The average diameter of the RBITC-labeled and MGITC-labeled bimetal-polymer Janus nanostructures was 122.1±2.4 nm and 112.0±15.9 nm, respectively. This result suggests that the absorption of the positively charged Raman dye induces formation of small aggregates although there was no significant change in the surface charge as seen from Table 1. It is due to the low concentration of the Raman dye, which is not enough to cover the whole surface of the bimetal cluster part, and the anions $Cl^-$ and $ClO_4^-$. In addition, the positively charged Raman dye may increase the net charge by connecting the bimetal nanocluster part with each other. After the directional clustering, the hydrodynamic diameter of the RBITC-labeled and MGITC-labeled superparticular structures was 450.1±3.1 nm and 401.1±10.0 nm, respectively. Due to the relatively more hydrophobic characteristics of the RBITC, the level of self-assembly of the superparticular structures labeled with the Raman dyes was significantly different even at the same concentration of the Raman dyes.

Figure 3A:
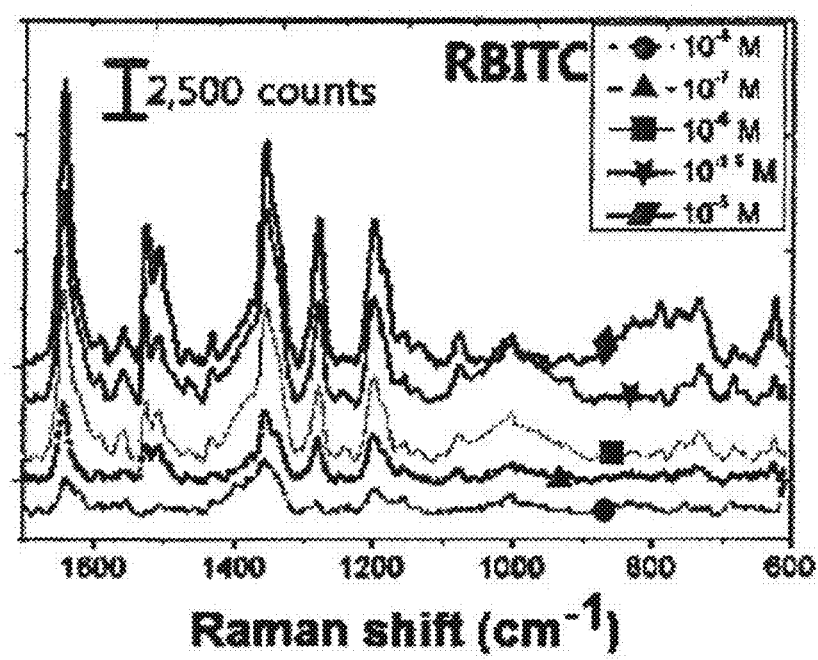
FIGS. 3A-3H show relative Raman spectra and Raman intensities for optimizing the concentration of a Raman dye in the range from $10^{-5}$ to $10^{-8}$ M.
Figure 3B:
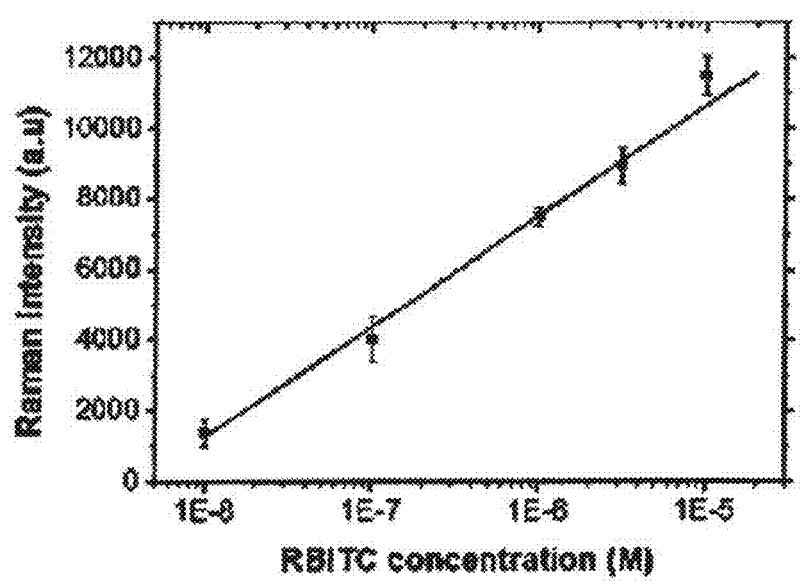
Figure 3C:
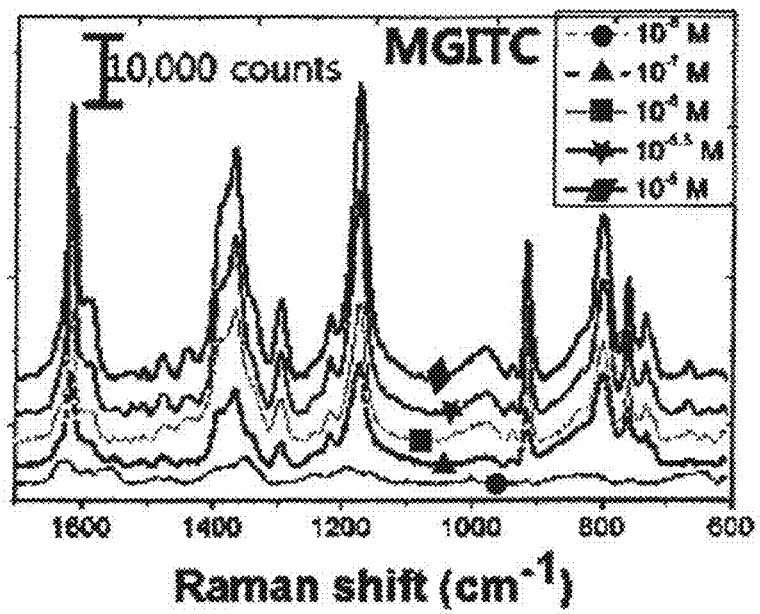
Figure 3D:
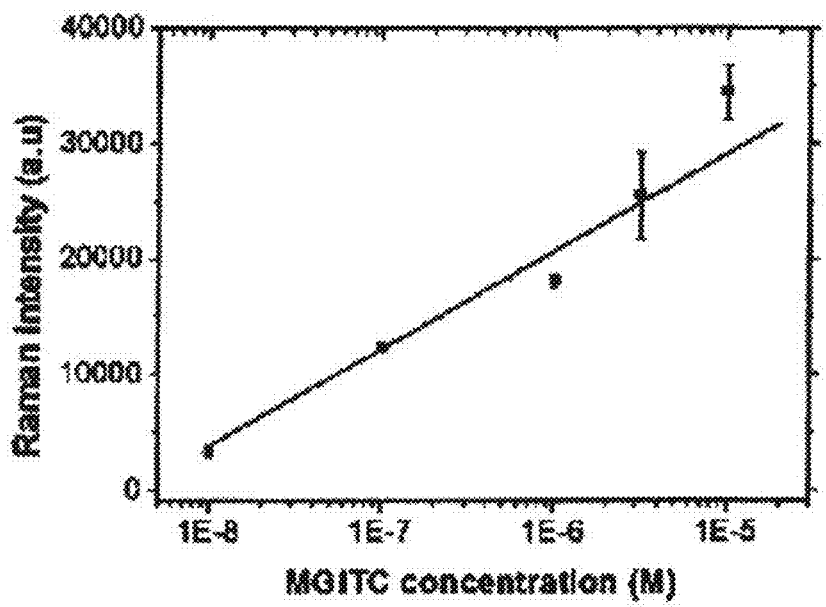
Figure 3E:
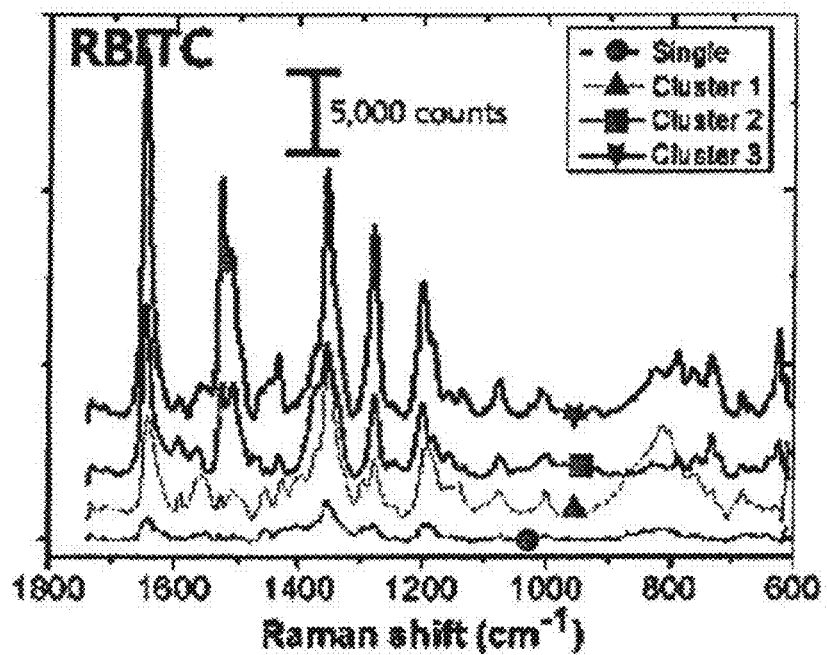
Figure 3F:
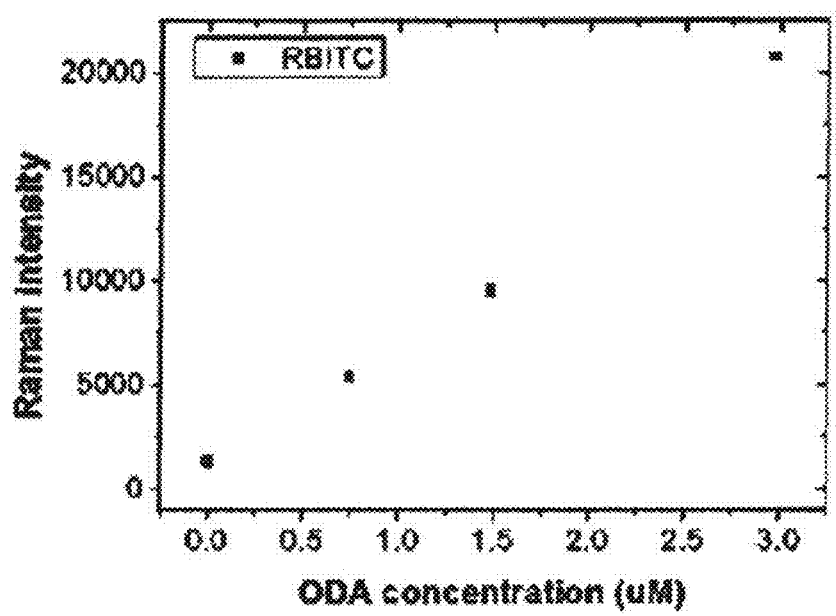
Figure 3G:
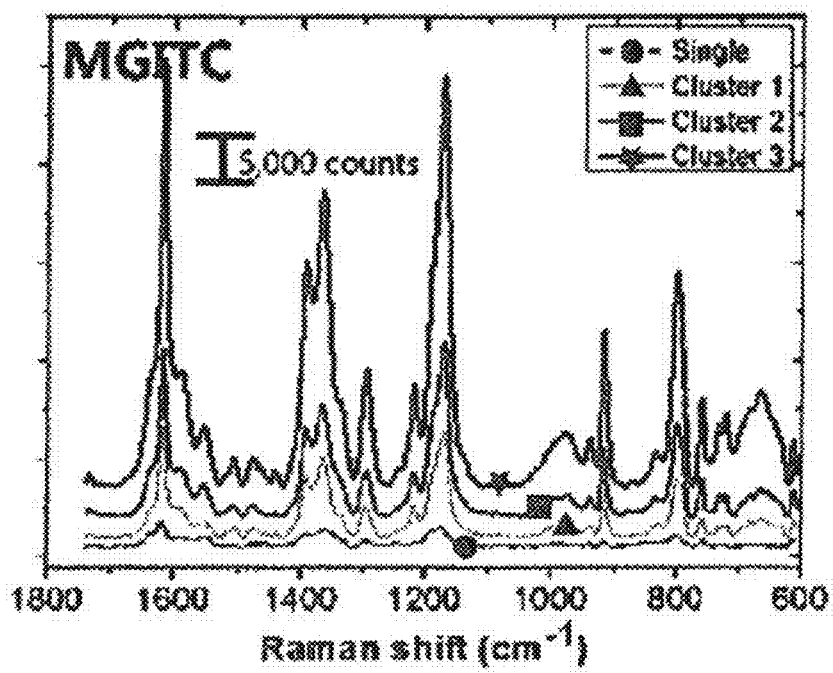
Figure 3H:
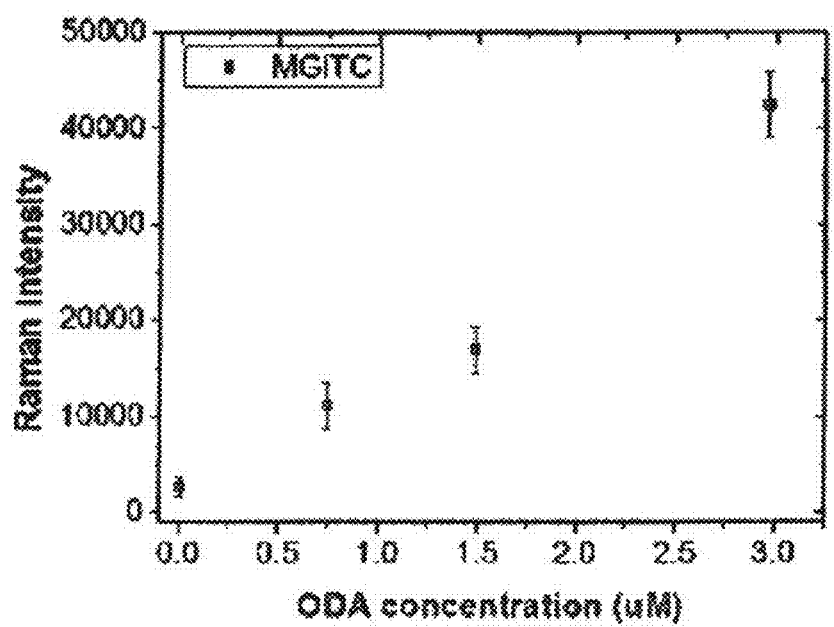
Figure 4A:
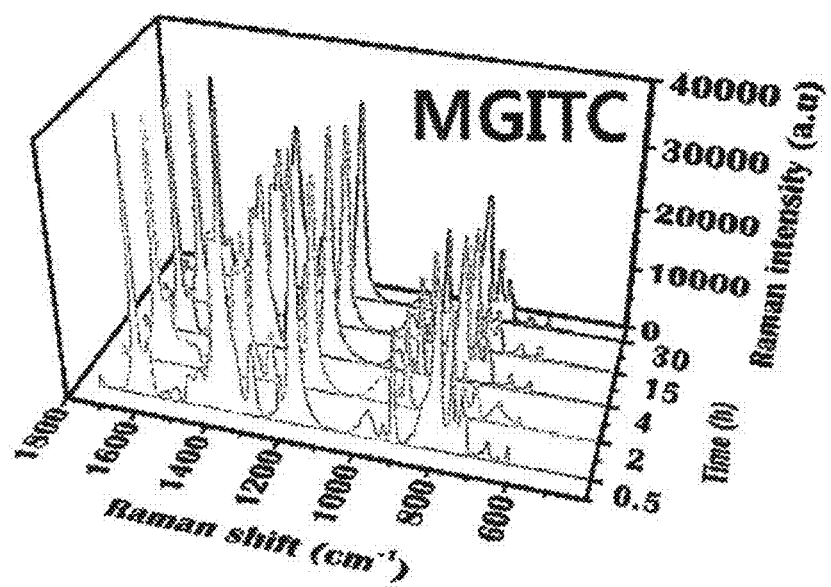
FIGS. 4A-4D show the colloidal stability with time and batch-to-batch variability of a superparticular structure.
Figure 4B:
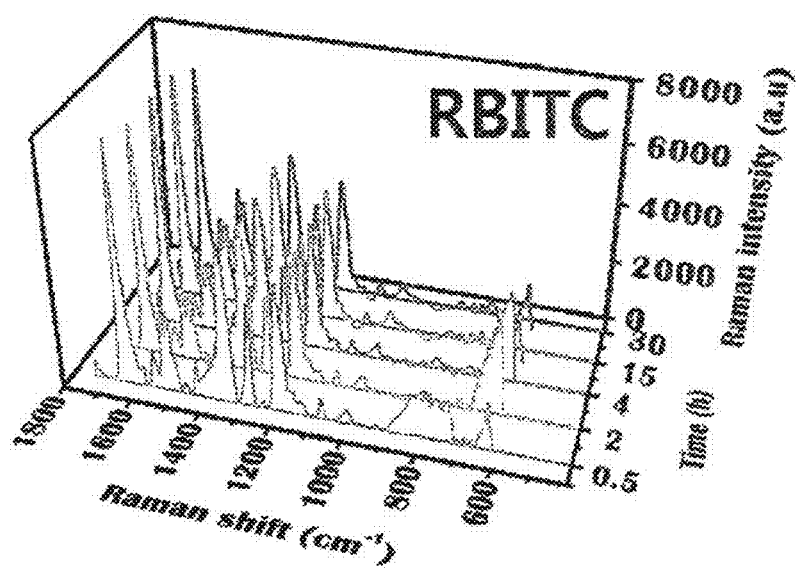
Figure 4C:
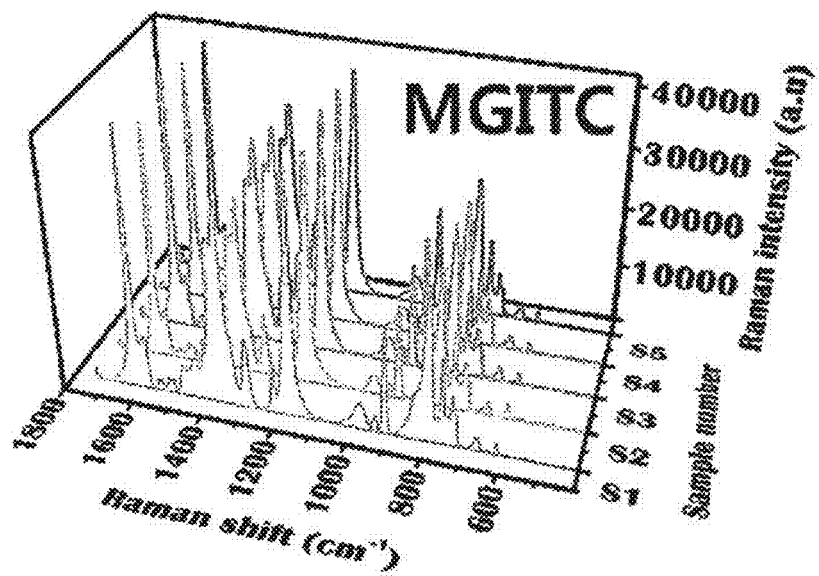
Figure 4D:
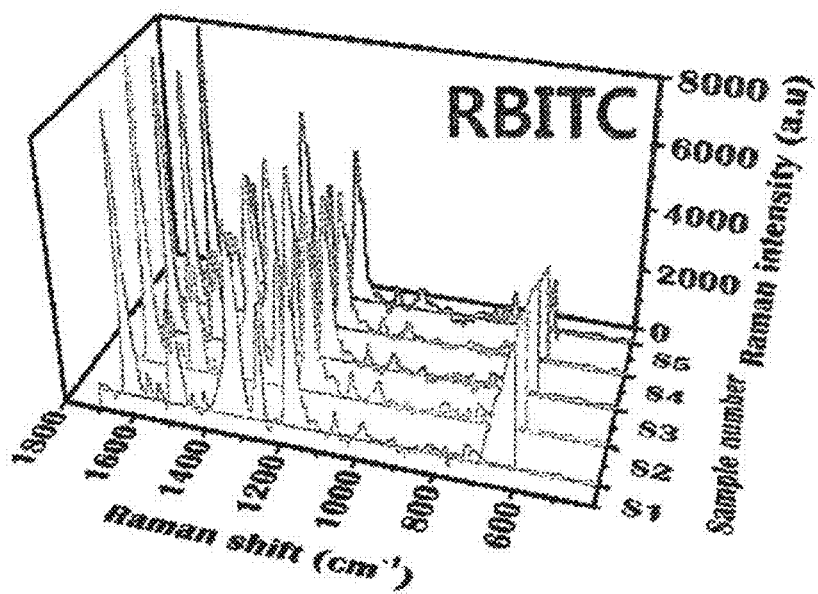

FIGS. 3A-3H shows the relative Raman spectra of the RBITC-labeled FIG. 3A and MGITC-labeled FIG. 3C superparticular structures for optimizing the optimum concentration of the Raman dye for very sensitive ERS-based biosensing. The Raman intensity of the RBITC as seen in FIG. 3B and the MGITC as seen in FIG. 3D at 1646 $cm^{-1}$ and 1617 $cm^{-1}$ was linearly proportional to the concentration of the Raman dye in the range of $10^{-5}$ to $10^{-8}$ M. That is to say, the Raman scattering intensity increased linearly with the concentration of the Raman dye ($R^2$=0.9826 for RBITC, $R^2$=0.9162 for MGITC). In particular, the intensity of the RBITC reached the maximum at $10^{-5}$ M and then decreased due to decreased colloid stability of the large aggregate. This was highly consistent with the DLS profile of FIG. 2D. As seen from FIGS. 3E-3H the Raman spectra of the bimetal-polymer Janus nanostructure and the bimetal-polymer Janus nanostructure cluster superparticular structure thereof at the RBITC FIG. 3E and MGITC FIG. 3G concentration of $10^{-6}$ M was measured for comparison of Raman intensity depending on clustering level. The bimetal-polymer Janus nanostructure showed a relatively lower Raman intensity, suggesting that insufficient absorption of the Raman dye interferes with the generation of strong Raman signals due to the thickness of the polymer part (polymer shell) despite the localized high surface plasmon resonance performance of the bimetal Au core-Ag shell. In contrast, after the directional self-assembly through selective modification of the bimetal nanocluster part, the Raman intensity was enhanced significantly due to increased electromagnetic field at the gap between the nanoparticles. The Raman intensity of the RBITC- and MGITC-labeled superparticular structures at 1646 $cm^{-1}$ and 1617 $cm^{-1}$ was about 15.92 and 15.59 times higher, respectively, than that of the superparticular structures at the ODA concentration of 2.968 µM.

FIGS. 4A-4D shows the colloidal stability with time (FIGS. 4A-4B) and batch-to-batch variability (FIGS. 4C-4D) of the MGITC (FIGS. 4A,4C) or RBITC (FIGS. 4B,4D)-labeled superparticular structure. The Raman spectra were measured in aqueous solutions for 5 different batches (S1-S5). The directional self-assembly of the bimetal nanocluster part was induced by exposing the polymer part under an aqueous condition for several days in order to achieve reproducible SERS signals through good colloidal stability and stabilization of the superparticular structure.

Figure 5A:
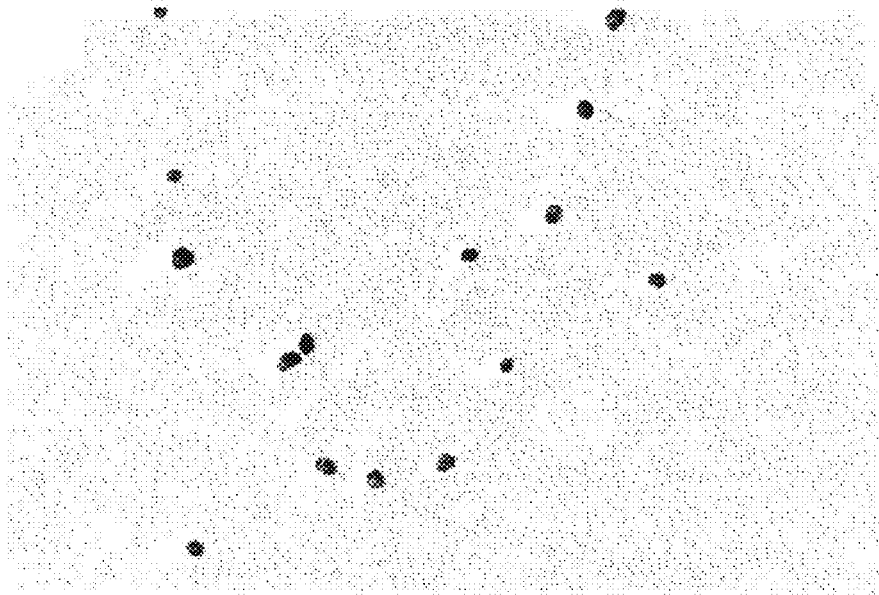
FIGS. 5A-5H shows TEM and SEM images for identifying size and morphology.
Figure 5B:
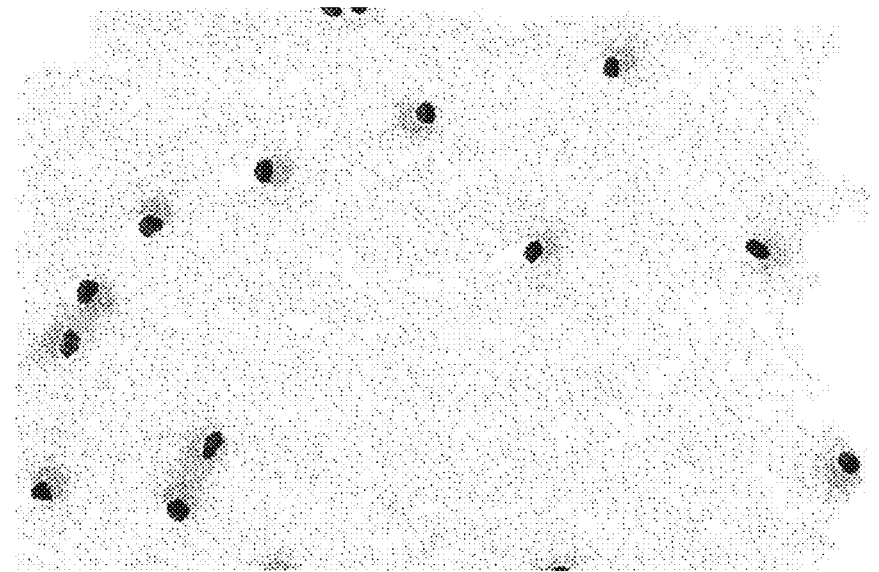
Figure 5C:
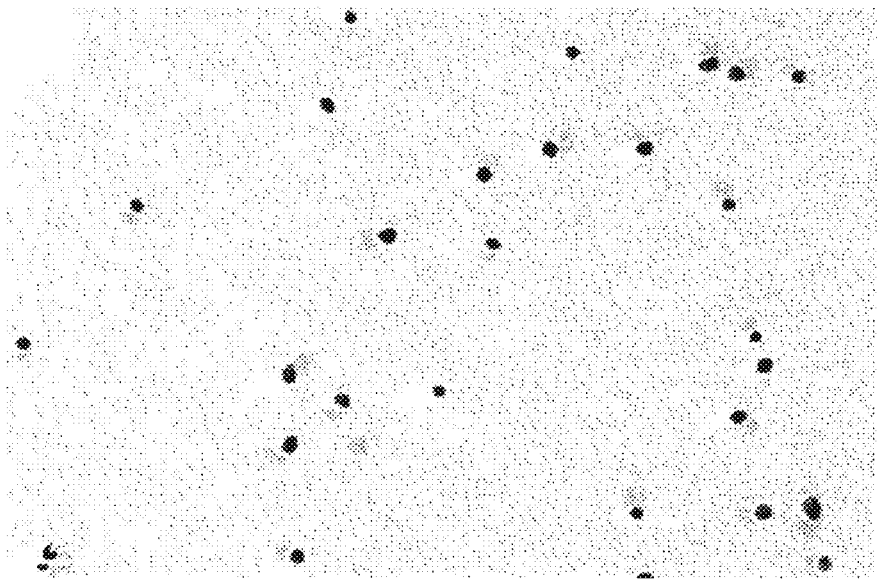
Figure 5D:
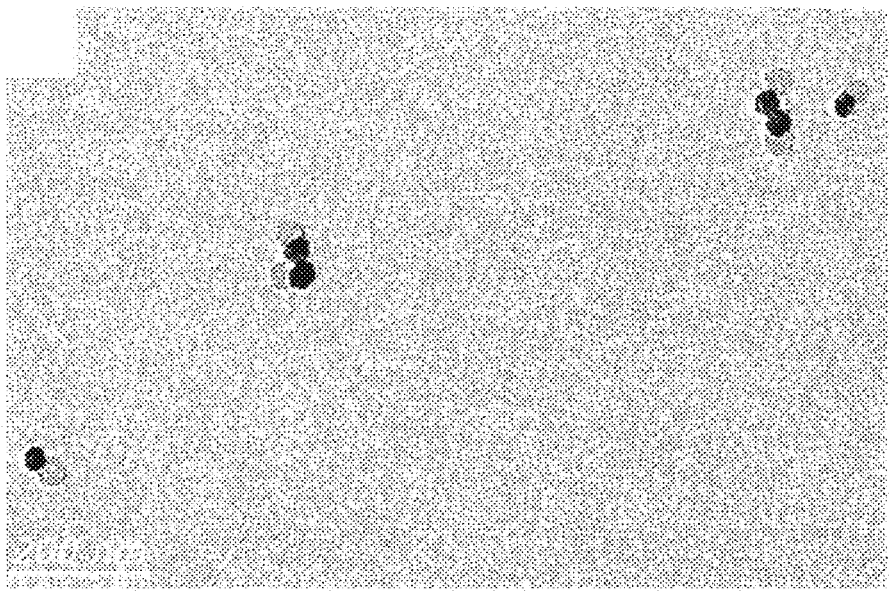
Figure 5E:
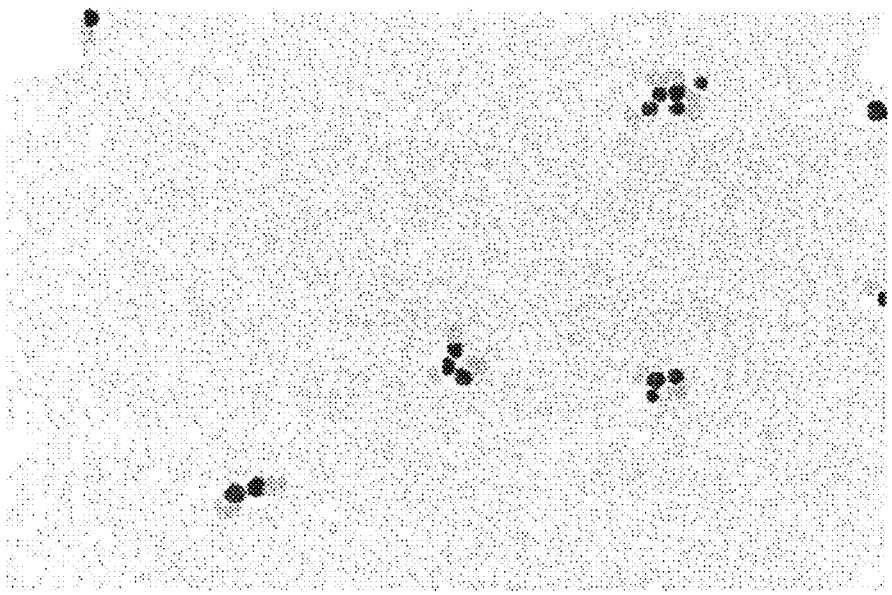
Figure 5F:
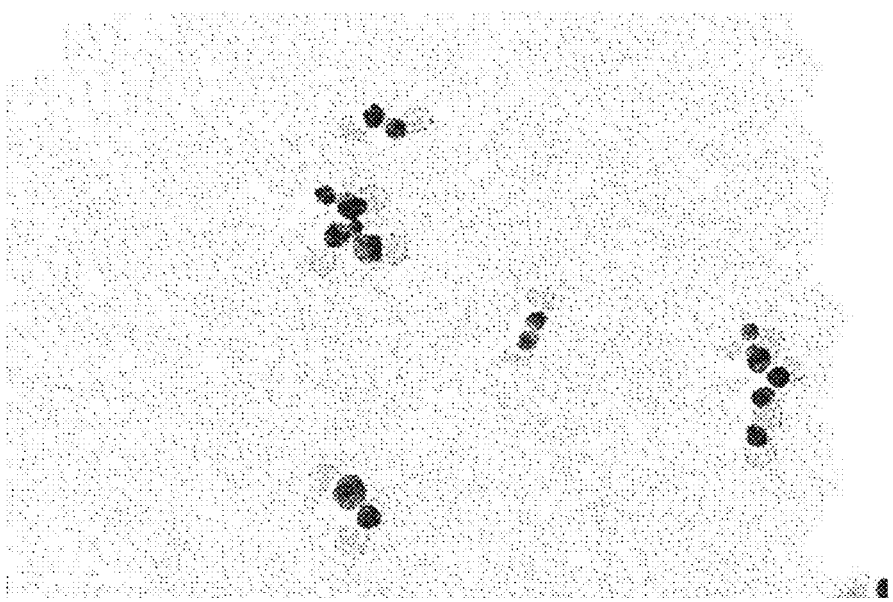
Figure 5G:
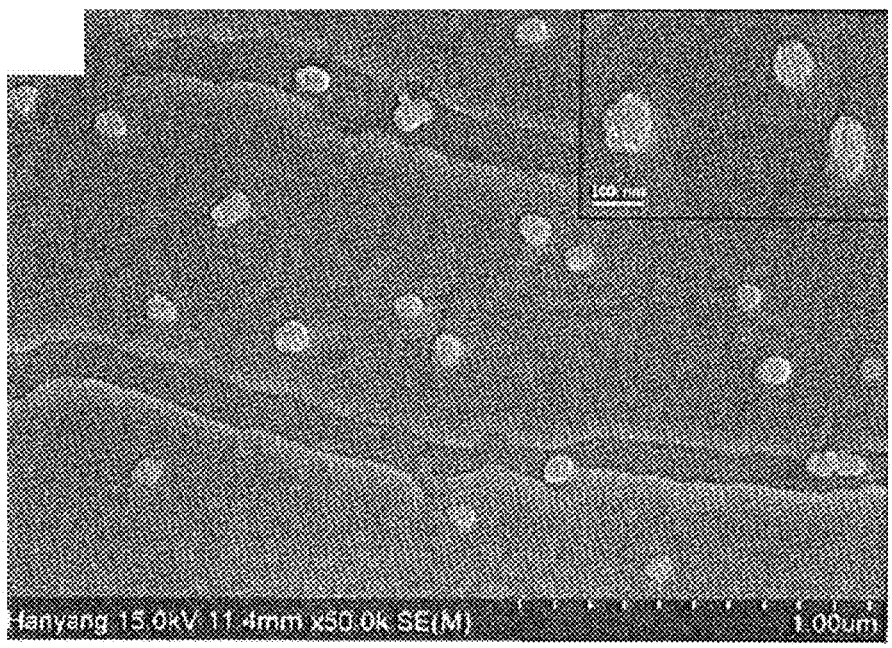
Figure 5H:
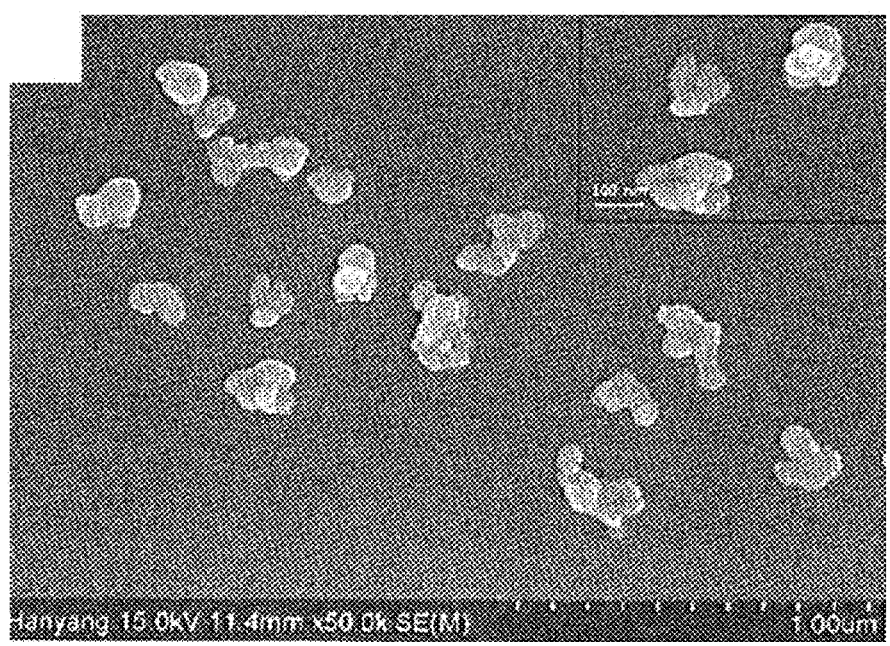

FIG. 5 shows the TEM and SEM images of the Au nanoparticle FIG. 5A, the bimetal-polymer Janus nanoparticle (FIG. 5B, FIG. 5C, FIG. 5G) and the self-assembled bimetal-polymer Janus nanostructure cluster superparticular structure thereof (FIG. 5D, FIG. 5E, FIG. 5F, FIG. 5H) at different magnifications for investigation of size and 3-dimensional morphology. The average size of the Au nanoparticle was 21.82±2.59 nm. The produced nanoparticle consisted of two different parts containing bimetal Au core-Ag shell and poly(aniline), as shown in FIG. 5B. After incubation of the nanoparticle overnight in a 3.6 mM SDS solution, the polymer part was formed through eccentric deposition on the Au nanoparticle, as seen from FIG. 5C. When the ODA containing a long hydrophobic alkyl chain was selectively introduced into the bimetal nanocluster part at various concentrations, directional self-assembly occurred as seen from FIG. 5D-5F. The degree of self-assembly was controlled by the concentration of the ODA. FIG. 5G and (h) are the SEM images clearly showing the 3-dimensional surface morphology of the bimetal-polymer Janus nanostructure and the self-assembled bimetal-polymer Janus nanostructure cluster superparticular structure thereof. The average diameter of the bimetal-polymer Janus nanostructure and the cluster structure thereof was 69±15 nm and 148±24 nm, respectively.

Figure 6A:
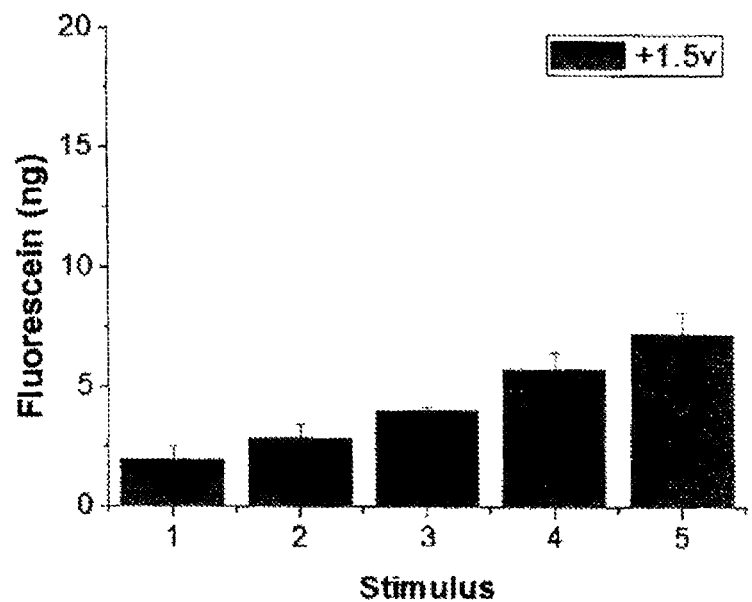
FIGS. 6A-6D shows cumulative fluorescein release from a bimetal-polymer Janus nanostructure contained in a PEG hydrogel measured by applying an electric field of +1.5 V or −1.5 V for 30 seconds with 1-minute intervals.
Figure 6B:
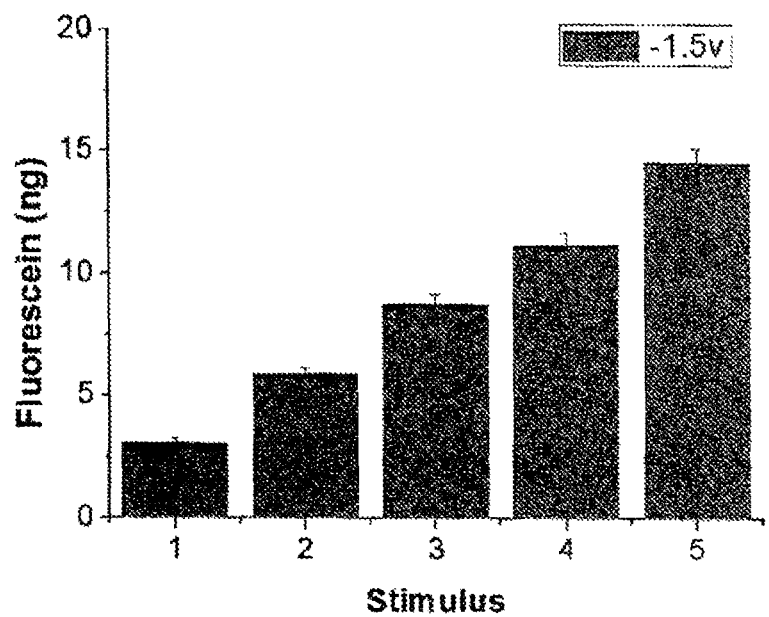
Figure 6C:
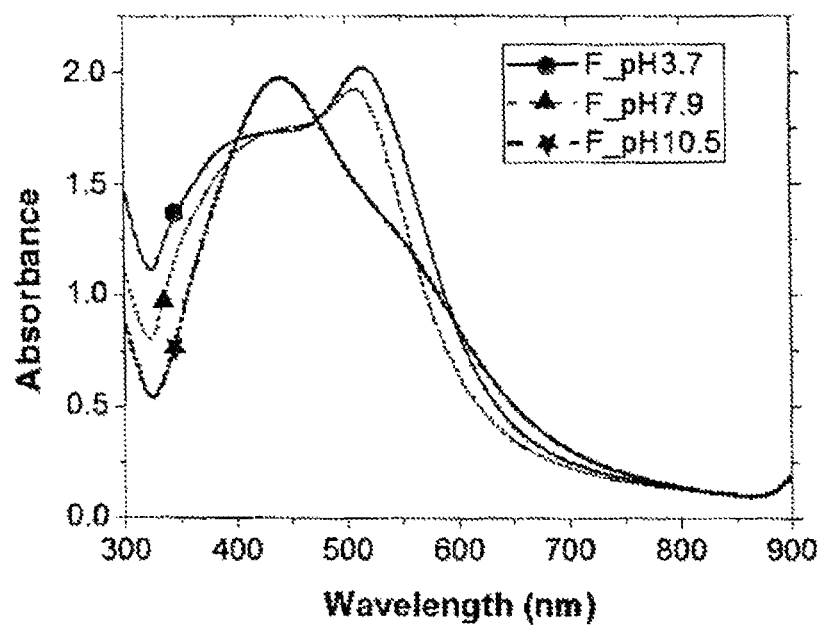
Figure 6D:
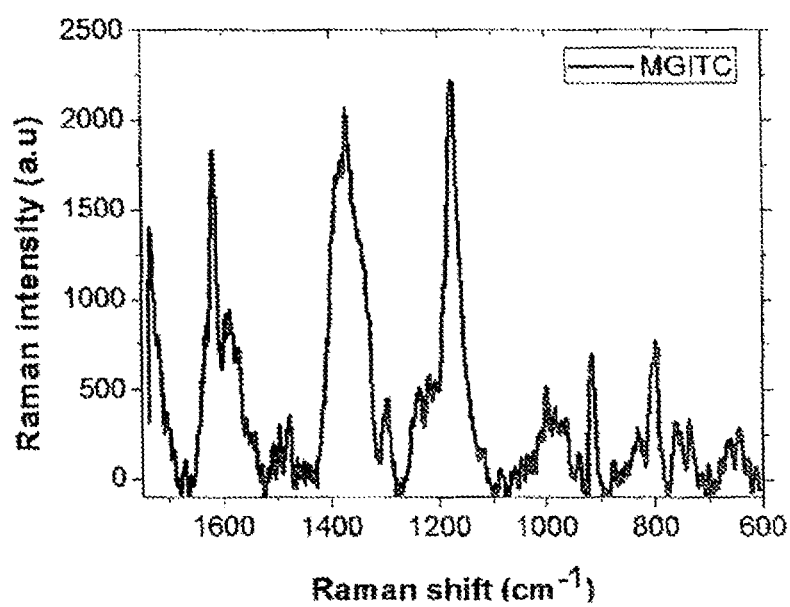

FIGS. 6A-6D shows cumulative fluorescein release from the bimetal-polymer Janus nanostructure contained in a PEG hydrogel measured by applying an electric field of +1.5 V (a) or −1.5 V (b) for 30 seconds with 1-minute intervals. The fluorescein was contained in the polymer part through electrostatic interaction between the negatively charged fluorescein and the positively charged aniline monomer. A PEG-nanoparticle hydrogel was formed by adding the concentrated fluorescein-loaded nanoparticle to a PEG solution and then irradiating UV. The release amount of the fluorescent material was calculated by measuring the fluorescence intensity at the maximum wavelength of 512 nm when stimulated at 480 nm. The polymer part of the bimetal-polymer Janus nanostructure consisting of the conductive polymer poly(aniline) showed responsiveness to the electric field. When a voltage of −1.5 V was applied between the two electrodes, the release amount of fluorescein was larger than when a voltage of +1.5 V was applied. When a voltage of −1.5 V was applied, the negatively charged drug fluorescein was released well because the electrostatic interaction between the fluorescein and the poly(aniline) part was decreased due to the decreased positive charge in the polymer part. FIG. 6C shows the UV-vis absorption of the fluorescein-loaded bimetal-polymer Janus nanoparticle at various pH of 4, 7 and 11. At higher pH, the electrostatic interaction of the fluorescein was decreased due to deprotonation of the aniline repeating unit. As a result, the drug was released well as the electrostatic force of the negatively charged drug fluorescein was decreased. FIG. 6D shows the Raman spectrum of MGITC released from the fluorescein-loaded bimetal-polymer Janus nanostructure. The Raman peaks of the MGITC and the fluorescein were at 1617 $cm^{-1}$ and 1176 $cm^{-1}$, respectively, suggesting that the bimetal-polymer Janus nanostructure is a fluorescence- and SERS-based nanoprobe.

<Example 5> Antibody Binding to Magnetic Bead and Self-Assembled Bimetal-Polymer Janus Nanostructure Cluster Superparticular Structure of Bimetal-Polymer Janus Nanostructure The self-assembled bimetal-polymer Janus nanostructure cluster superparticular structure and the magnetic bead were bound to two different sets of a monoclonal antibody (mAb) and a polyclonal antibody (pAb) for two target proteins, IgG (immunoglobulin G) and CEA (carcinoembryonic antigen). First, the polymer part (polymer shell) of the superparticular structure was bioconjugated to the anti-human IgG polyclonal antibody (anti-human IgG pAb) or the anti-human CEA polyclonal antibody (anti-human CEA pAb) through an amide coupling reaction between the amine group remaining in the poly(aniline) part and the carboxyl group present in the antibody. The coupling reaction was conducted using EDC and sulfo-NHS (sulfo-N-hydroxysuccinimide ester). Specifically, after adding 5 pL of 1.0 mg/mL or 2.0 mg/mL anti-human IgG pAb or anti-human CEA pAb to a dispersion of the bimetal-polymer Janus nanoparticle containing 60 mM of EDC and 9.2 mM of sulfo-NHS in 10 mM PBS of pH 7.4, the mixture was stirred for 3 hours until the total pAb concentration was 5 pg/mL or 10 pg/mL, respectively. The anti-human IgG pAb- or anti-human CEA pAb-conjugated superparticular structure was centrifuged at 3,000 rpm and then resuspended in PBS. Also, the magnetic bead was chemically bound to anti-human IgG monoclonal antibody (anti-human IgG mAb) or anti-human CEA monoclonal antibody (anti-human CEA mAb) by activating the carboxyl group remaining on the polymer nanoparticle which was thermally stabilized overnight at 175° C. Specifically, 1.25 mg of the magnetic bead was suspended in 0.9 mL of PBS and then sonicated for 2 minutes using a tip sonicator at 20.0% amplitude with 3/3 sec on/off cycles. The uniformly suspended magnetic bead was mixed with 5.0 mM EDC and 5.0 mM sulfo-NHS and then stirred for 1 hour. 2.96 mg/mL or 3.56 mg/mL anti-human IgG mAb or anti-human CEA mAb diluted with 100 pL of PBS was slowly added to the magnetic bead solution to a final concentration of 7.4 pg/mL or 8.9 pg/mL and the mixture was stirred for 1 hour. After removing the unbound anti-human IgG mAb or anti-human CEA mAb using a magnetic field, the antibody-conjugated magnetic bead was resuspended in PBS for SERS-based biosensing of IgG and CEA.

Figure 1C:
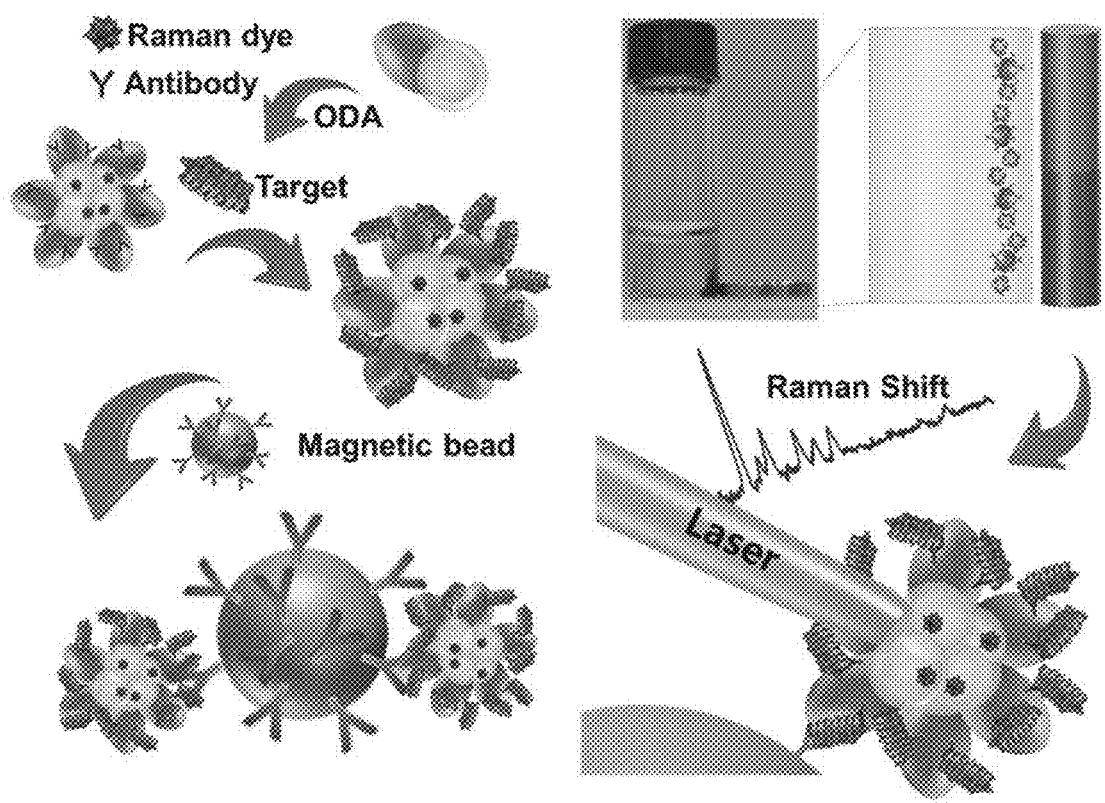
Figure 7:
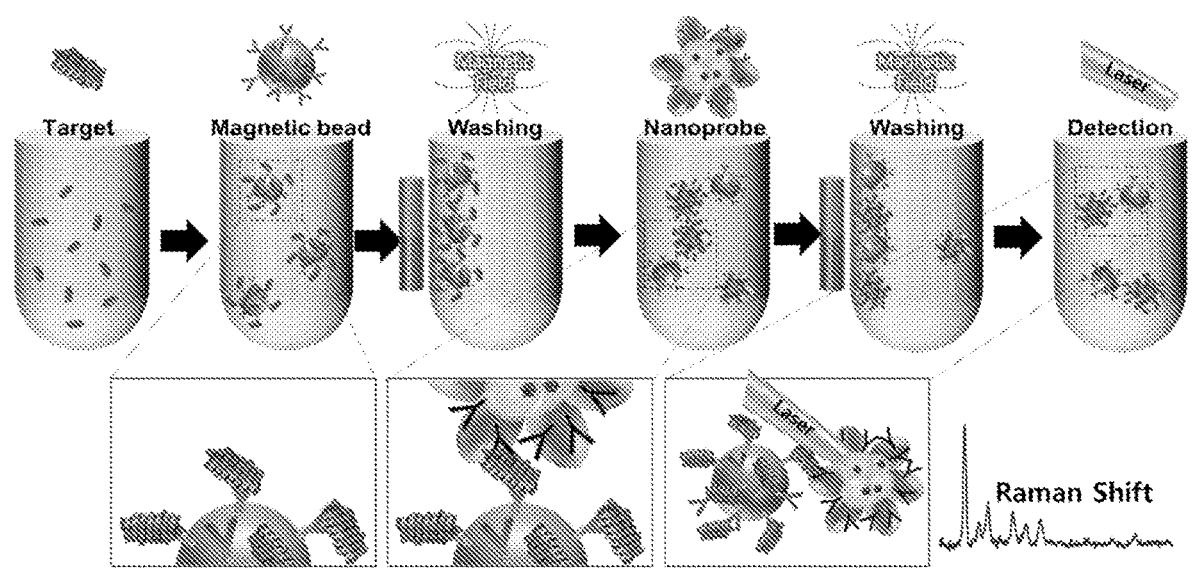
FIG. 7 schematically shows SERS-based immunoassay for detecting a target protein.
Figure 8A:
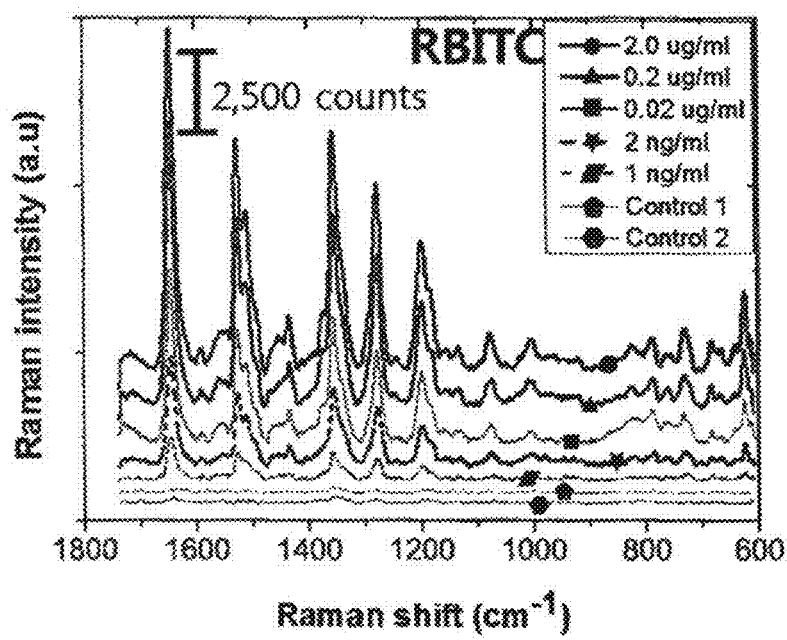
FIGS. 8A-8D shows Raman spectra and Raman intensity depending on IgG concentration. The SERS peak intensity of the RBITC- or MGITC-labeled superparticular structure at 1646 $cm^{-1}$ and 1617 $cm^{-1}$ increased linearly with the IgG concentration. $R^2$=0.9435-0.9806 and $R^2$=0.9572-0.9953. Control 1 and control 2 are respectively anti-human IgG pAb and an IgG-free control group.
Figure 8B:
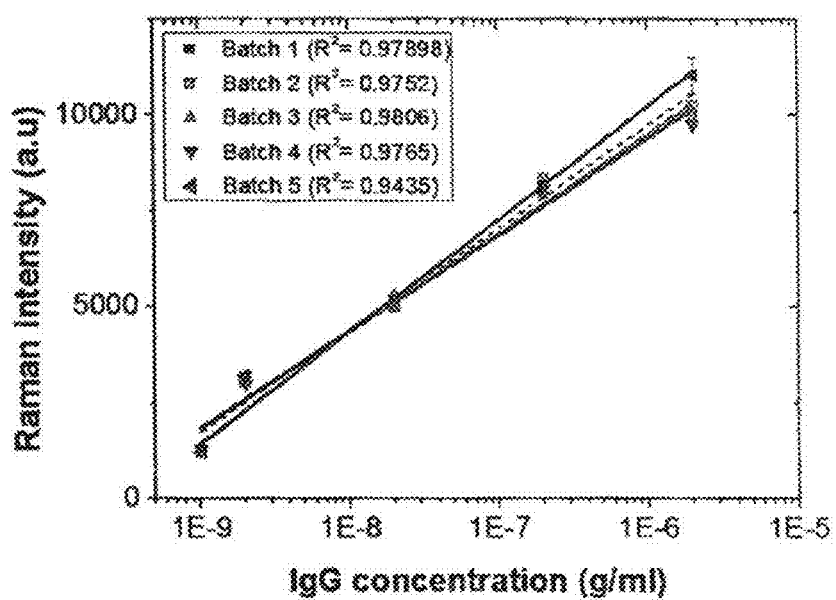
Figure 8C:
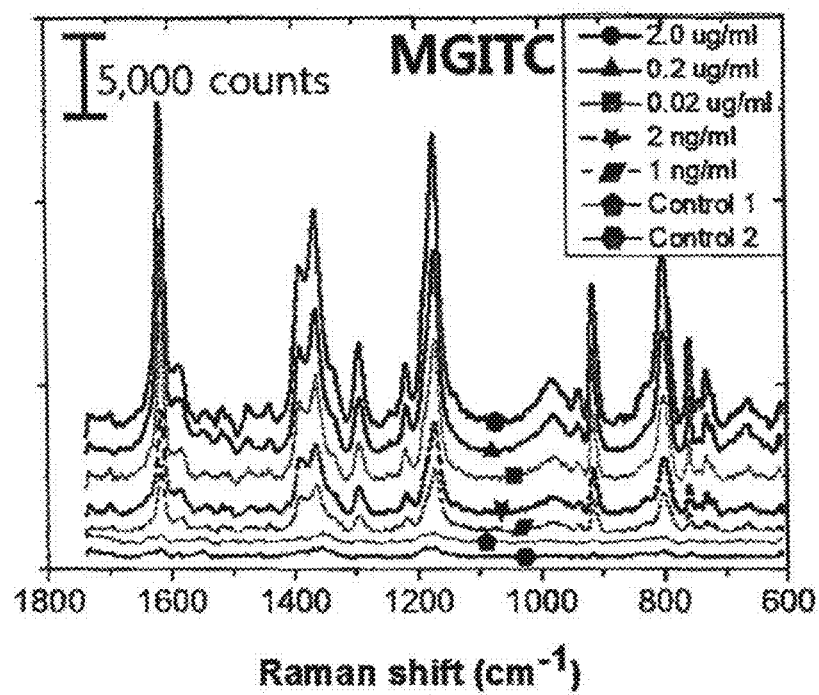
Figure 8D:
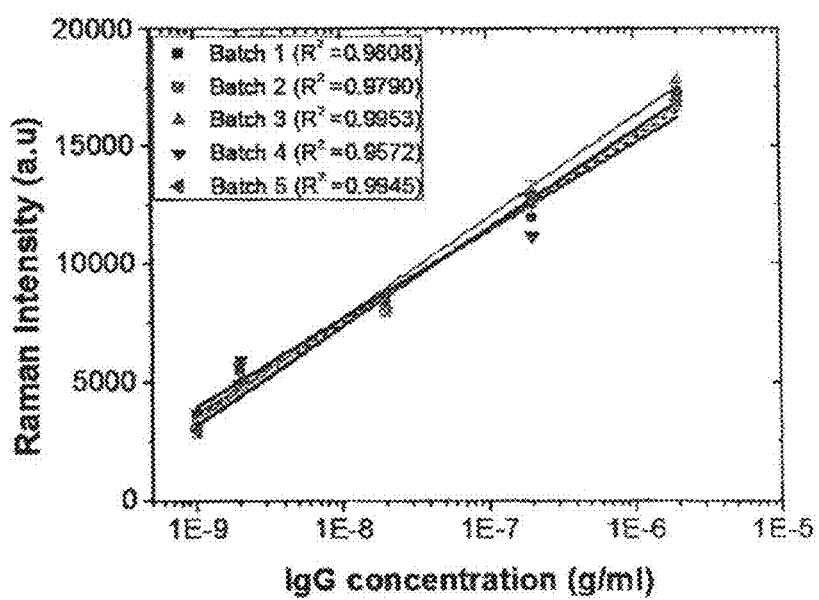
Figure 9A:
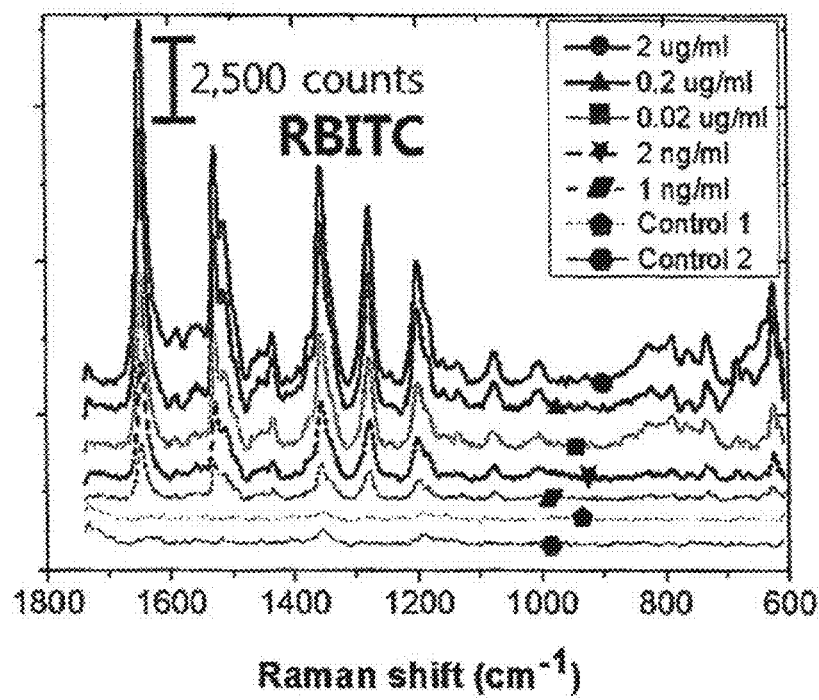
FIGS. 9A-9D shows Raman spectra and Raman intensity depending on CEA concentration. The SERS peak intensity of the RBITC- or MGITC-labeled superparticular structure at 1646 $cm^{-1}$ and 1617 $cm^{-1}$ increased linearly with the CEA concentration. $R^2$=0.9801-0.9856 and $R^2$=0.9257-0.9838. Control 1 and control 2 are respectively anti-human CEA pAb and a CEA-free control group.
Figure 9B:
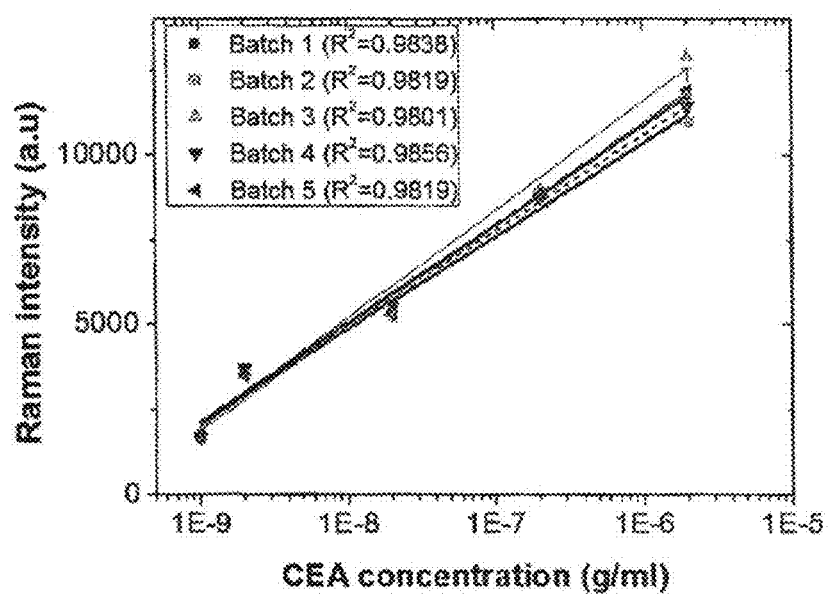
Figure 9C:
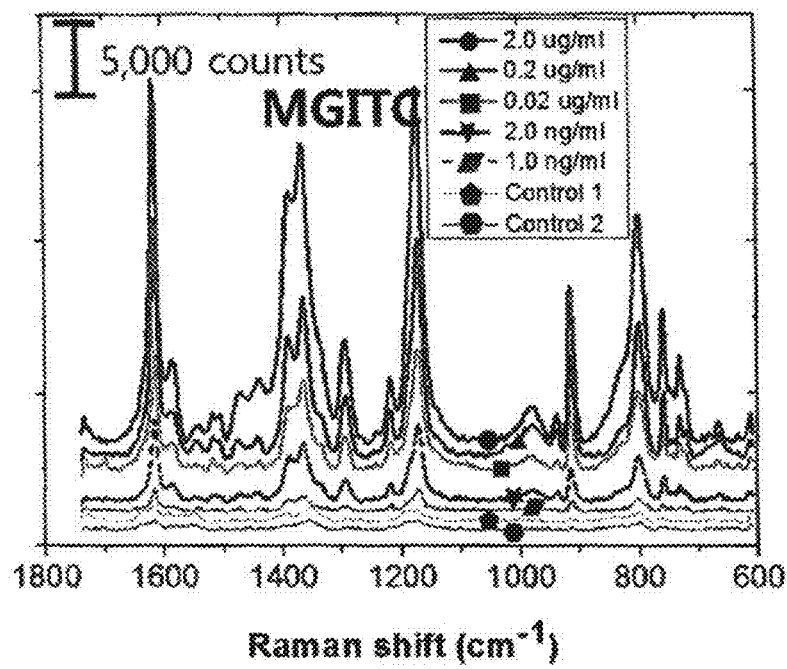
Figure 9D:
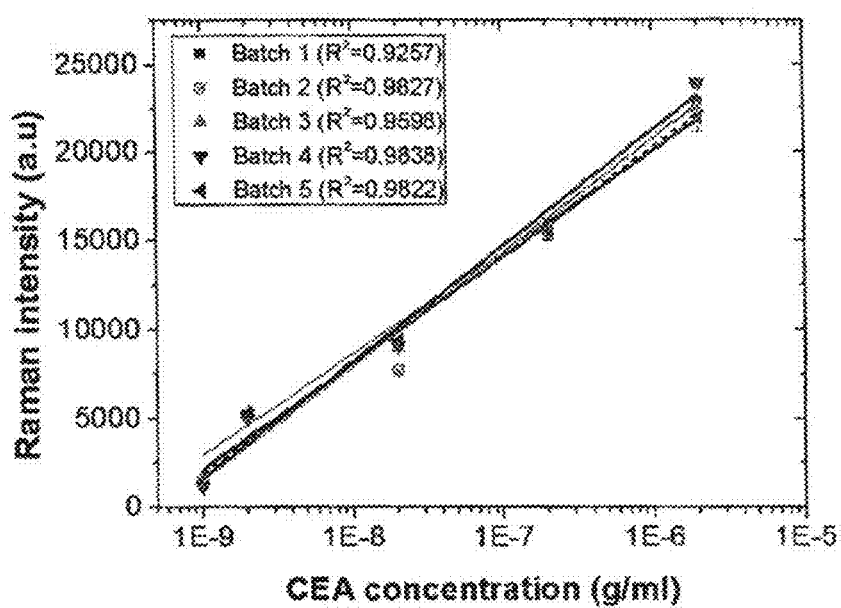

<Example 6> SERS-Based Biosensing for Target Protein IgG and CEA Using Superparticular Structure and Magnetic Bead The superparticular structure labeled with the Raman reporter was used as an SERS nanoprobe for quantitative analysis of the target proteins IgG and CEA. A sandwich immune complex was formed using the magnetic bead bound to anti-human IgG mAb or anti-human CEA mAb. First, the magnetic bead with anti-human IgG mAb or anti-human CEA mAb bound was added to a buffer containing IgG or CEA at 6 different concentrations in the range from 2 pg/mL to 1 ng/mL and then incubated for 1 hour. The target protein was washed with an external magnetic field and then resuspended in fresh PBS. Then, a sandwich immune complex consisting of the magnetic bead, the target protein and a SERS nanoprobe was prepared by adding a SERS nanoprobe with anti-human IgG pAb or anti-human CEA pAb bound to each immune complex of the target protein and the magnetic bead and then incubating for 1 hour as shown in FIG. 1C. After removing the unbound SERS nanoprobe using a magnetic field, the produced sandwich immune complex was resuspended in PBS for SERS measurement (FIG. 7). Also, experiments for two controls were conducted to evaluate the selective coupling performance of the SERS nanoprobe with no antibody or target protein bound.

FIGS. 8 and 9 show the Raman spectra and Raman intensity of the targets depending on the concentration of IgG and CEA. As the IgG concentration increased in the range from 1.0 ng/mL to 2.0 pg/mL, the Raman intensity of the RBITC-labeled or MGITC-labeled superparticular structure was increased due to the formation of the sandwich immune complex. Control 1 and control 2 are anti-human IgG pAb and IgG-free control groups, respectively. Also, the representative SERS peak intensity of RBITC and MGITC at 1646 $cm^{-1}$ and 1617 $cm^{-1}$ increased linearly with the IgG concentration as shown in FIG. 8 ($R^2$=0.9435-0.9806 and $R^2$=0.9572-0.9953). Likewise, the Raman intensity of the RBITC-labeled or MGITC-labeled superparticular structure increased linearly with the CEA concentration as shown in FIG. 9 ($R^2$=0.9801-0.9856 and $R^2$=0.9257-0.9838). Control 1 and control 2 are anti-human CEA pAb and CEA-free control groups, respectively. The detection limit for IgG and CEA was below 1 ng/mL.

Invention 2

<Example 1> Synthesis of Janus Nanostructure Consisting of AuNR Core-Ag Satellite Bimetal Part and Polymer Part A gold nanorod (AuNR) was synthesized by the seed-mediated growth method. Specifically, after dissolving 5 mL of 0.20 M CTAB (hexadecyltrimethylammoniumbromide) (Sigma-Aldrich, USA) at 29-30° C. and mixing with 5 mL of 0.0005 M gold(III) chloride hydrate ($HAuCl_4 \cdot 3H_2O$) (Sigma-Aldrich, USA), 0.010 mL of cold 0.010 M $NaBH_4$ was added. A seed solution produced as the color of the reaction solution changed from yellow to yellowish brown was maintained at 29-30° C. and used within 2-2.5 hours. In order to grow a nanorod on the seed particle, 0.25 mL of 0.004 M $AgNO_3$ and 5 mL of 0.20 M CTAB were mixed at 29-30° C. Then, the solution was stirred after adding 5.0 mL of 0.001 M $HAuCl_4$. After mixing for 30-40 minutes, the color change of the growth solution was induced from deep yellow to colorless by adding the reducing agent ascorbic acid. In the final stage, 12 µL of the seed solution was added to the colorless solution and then the color of the solution was slowly changed in 10-20 minutes. The solution was stirred and stored overnight at 29-30° C. In order to change the surface characteristics of the seed metal nanoparticle, a metal-polymer composite was prepared through electrostatic interaction. The CTAB-capped AuNR was centrifuged at 10,000 rpm for 10 minutes and then resuspended in a 1 mM NaCl solution. After dissolving the negatively charged polymeric ligand PSS (poly(styrene sulfonate)) (Sigma-Aldrich, USA) in a 1 mM NaCl solution to a final concentration of 0.06-0.2 w/v %, it was added to the AuNR solution to form a metal-polymer (AuNR-PSS) composite. After purifying and concentrating the metal-polymer (AuNR-PSS) composite by centrifuging at 8,000 rpm for 10 minutes, a bimetal-polymer Janus nanoparticle consisting of an AuNR core-Ag satellite bimetal part and a poly(aniline) part was prepared through surface-templated polymerization based on oxidation-reduction. Specifically, aniline and SDS were dissolved in 7.5 mL to deionized water to final concentrations of 5 mM and 0.9 mM, respectively. After adding the concentrated metal-polymer (AuNR-PSS) composite to the solution and vortexing, 2.5 mL of a silver nitrate solution was added to a final concentration of 2.5 mM. The reaction was conducted under a dark condition at room temperature for 24 hours without stirring. The reaction solution was further incubated overnight in a 3.6 mM SDS solution, so that poly(aniline) was eccentrically deposited on only one side of the AuNR core-Ag satellite bimetal nanostructure. The resulting solution was purified by centrifuging at 8,000 rpm for 10 minutes and then resuspended in a 3.6 mM SDS solution to prevent aggregation. 1 mL of the solution of the Janus nanoparticle consisting of the AuNR core-Ag satellite bimetal part and the poly(aniline) part was centrifuged at 10,000 rpm for 10 minutes and then transferred to 1 mL of deionized water. The colloid solution was mixed with freshly prepared MGITC in the concentration range from $10^{-5}$ to $10^{-5.5}$ M and then incubated for 2 hours. The MGITC was selectively adsorbed onto the surface of the Ag satellite of the AuNR core-Ag satellite bimetal nanoparticle through the isothiocyanate group (—N=C=S) of the Raman dye.

<Example 2> Synthesis of Janus Nanostructure Consisting of AuNP (AuNS) Core-Ag Satellite Bimetal Nanoparticle Part and Polymer Part A citrate-capped gold nanoparticle (AuNP) or gold nanosphere (AuNS) was synthesized by citrate reduction. Specifically, after adding a stock solution of gold(III) chloride hydrate to 100 mL of deionized water to a concentration of 0.01%, 1.5 mL of a 1% sodium citrate solution was added quickly while stirring and boiling the solution. The solution turned red within 5 minutes, which suggests the reduction of gold ion, and the reaction was conducted further for 20 minutes. The resulting solution was cooled to room temperature. Also, a bimetal AuNP core-Ag satellite nanostructure having a polymer part was synthesized through ligand-mediated surface control of the AuNP seed particle and an oxidation-reduction reaction between silver nitrate and aniline. The Ag deposition onto the AuNP seed particle was controlled by controlling interfacial energy using a ligand containing —SH and —$NH_2$ groups and thereby modifying the surface characteristics of the metal nanoparticle. Specifically, the citrate-capped AuNP was centrifuged at 10,000 rpm for 10 minutes and resuspended in deionized water. A small-molecule ligand containing —SH and —$NH_2$ groups, 4-aminothiophenol (ATP), was bound onto the AuNP seed to a final concentration of $10^{-5}$ M. After purifying by centrifugation, a bimetal-polymer Janus nanoparticle consisting of an AuNP core-Ag satellite bimetal part and a poly(aniline) part was prepared through surface-templated polymerization based on oxidation-reduction. Specifically, aniline and SDS were dissolved in 7.5 mMdeionized water to final concentrations of 5 mM and 0.9 mM, respectively. After adding the concentrated metal-ligand (AuNP-ATP) composite to the solution and vortexing, 2.5 mL of a silver nitrate solution was added to a final concentration of 2.5 mM. The reaction was conducted under a dark condition at room temperature for 24 hours without stirring. The reaction solution was further incubated overnight in a 3.6 mM SDS solution, so that poly(aniline) was eccentrically deposited on only one side of the bimetal AuNP core-Ag satellite nanostructure. The resulting solution was purified by centrifuging at 8,000 rpm for 10 minutes and then resuspended in a 3.6 mM SDS solution to prevent aggregation. 1 mL of the solution of the Janus nanoparticle consisting of the AuNP core-Ag satellite bimetal part and the poly(aniline) part was centrifuged at 10,000 rpm for 10 minutes and then transferred to 1 mL of deionized water.

<Comparative Example 1> Synthesis of Janus Nanostructure Consisting of AuNR Core-Ag Shell Nanoparticle and Polymer Part A bimetal-polymer Janus nanoparticle consisting of a bimetal AuNR core-Ag shell part and a poly(aniline) part was prepared through surface-templated polymerization based on oxidation-reduction in the same manner as in Example 1, except that the surface of the seed AuNR was not modified with PSS. Specifically, aniline and SDS were dissolved in 7.5 mM deionized water to final concentrations of 5 mM and 0.9 mM, respectively. After adding the concentrated AuNR to the solution and vortexing, 2.5 mL of a silver nitrate solution was added to a final concentration of 2.5 mM. The reaction was conducted under a dark condition at room temperature for 24 hours without stirring. The reaction solution was further incubated overnight in a 3.6 mM SDS solution, so that poly(aniline) was eccentrically deposited on only one side of the AuNR core-Ag shell bimetal nanostructure. The resulting solution was purified by centrifuging at 8,000 rpm for 10 minutes and then resuspended in a 3.6 mM SDS solution to prevent aggregation. 1 mL of the solution of the Janus nanoparticle consisting of the AuNR core-Ag shell bimetal part and the poly (aniline) part was centrifuged at 10,000 rpm for 10 minutes and then transferred to 1 mL of deionized water. The colloid solution was mixed with freshly prepared MGITC at concentrations of $10^{-5}$ to $10^{-5.5}$ M and then incubated for 2 hours, respectively. The MGITC was selectively adsorbed onto the surface of the Ag shell of the AuNR core-Ag shell bimetal nanoparticle through the isothiocyanate group (—N=C=S) of the Raman dye.

<Example 3> Synthesis of Magnetic Nanoparticle (MNP) and Magnetic Bead Through Electrohydrodynamic (EHD) Jetting An iron oxide nanoparticle ($Fe_3O_4$) was prepared by chemical coprecipitation using a 1:2 (molar ratio) mixture of $Fe^{2+}$ and $Fe^{3+}$ in an aqueous ammonia solution as a precipitating agent. Specifically, 0.86 g of iron(II) chloride ($FeCl_2$) tetrahydrate and 2.35 g of iron(III) chloride ($FeCl_3$) were mixed by stirring in 40 mL of deionized water and degassed with nitrogen gas for 30 minutes. After raising temperature to 80° C. and adding 5 mL of ammonium hydroxide ($NH_4OH$) using a syringe, the mixture was heated for 30 minutes. After adding 1 g of citric acid to a reaction flask and heating to 90° C., the reaction solution was stirred for 90 minutes. Finally, the $Fe_3O_4$ magnetic nanoparticle (MNP) was washed twice with deionized water under a static magnetic field of hundreds of Gauss. Also, a magnetic bead was prepared by concentrating a small aliquot of a MNP solution using a magnetic field, adding to a polymer solution and conducting electrohydrodynamic (EHD) jetting. 4.5 w/v % of poly(acrylamide-co-acrylic acid) (poly(AAm-co-AA)) was prepared in a 3:1 (volume ratio) mixture of deionized water and ethylene glycol and the concentrated MNP was uniformly suspended in the polymer solution. For electrohydrodynamic (EHD) dispersion, the suspension of the dispersed MNP was put in a 1.0-mL syringe (BD, Franklin Lakes, USA) having a 23-gauge stainless steel capillary tube. To achieve a stable Taylor cone and a cone-jet mode, an optimized viscosity was obtained by dissolving the polymer in a viscous solvent such as ethylene glycol without increasing the polymer concentration. The microsyringe pump KDS-100 (KD Scientific, Inc., USA) allowing the flow of the MNP suspension at a constant rate was equipped at the syringe. A 0.018-mm thick aluminum foil (Fisherbrand; Thermo Fisher Scientific, USA) was used as a collecting plate. A high voltage was applied between the capillary tube connected to an anode and the aluminum foil connected to a cathode using the high-voltage power source NNC HV 30 (Nano NC, Korea). The distance between the two electrodes was 20-25 cm. The high voltage was maintained at 15-20 kV and the flow rate of the two solutions was maintained at 0.08-0.15 mL/hour. During the EHD jetting, the single-phase Taylor cone, jet stream and jet break-up were visualized and captured using a high-resolution digital camera (D-90, Nikon Corporation, Japan). After the EHD jetting, the formed magnetic bead was thermally crosslinked overnight at 175° C. Finally, the magnetic bead in the form of a powder was collected by scraping from the foil and used for the following experiments.

<Example 4> Characterization of Janus Nanostructure Consisting of Au Core-Ag Satellite Bimetal Part and Polymer Part For measurement of the optical properties of the Au—Ag core-shell nanoparticle cluster nanostructure having the eccentrically deposited poly(aniline) part, the UV-vis absorption spectra of the single nanoparticle and the cluster thereof were investigated in the wavelength range of 300-900 nm using a UV-vis spectrometer (Cary-100 Bio, Varian Biotech, USA). The hydrodynamic diameter and size distribution of the nanoparticle were analyzed at 633 nm at a scattering angle of 90° by dynamic light scattering (DLS) (Zeta-sizer Nano ZS90, Malvern Instruments, Malvern, UK) using a Ne—He laser. In addition, the zeta ($\zeta$) potential was measured for characterization of surface charge in deionized water. Transmission electron microscopic analysis was conducted using JEM-2100F FE-STEM (JEOL, Germany) operating at an accelerating voltage of 80-200 kV. The average diameter, size distribution and surface morphology of the nanoparticle were measured by scanning electron microscopy (SEM) (VEGA-SB3, TESCAN, Czech Republic) operating at 0.5-30 kV with a focused beam. The nanoparticle was coated with a thin conductive platinum layer using K575X Turbo Sputter Coater (Emitech Ltd., UK). All SERS measurements were performed using a Renishaw inVia Raman microscope system equipped with a Renishaw He—Ne laser operating at a wavelength (A) of 632.8 nm in response to a stimulation source having a laser output of 12.5 mW. The Rayleigh line was removed from the collected SERS spectra using a holographic notch filter located in the collection path. Raman scattering was collected using a charge-coupled device (CCD) camera at a spectral resolution of 1 $cm^{-1}$ and all the SERS spectra were calibrated to the 520 $cm^{-1}$ silicon line. A 20× objective lens was used to focus the laser spot on the glass capillary tube in a wavelength range of 608-1738 $cm^{-1}$. The SERS spectra were collected for 1 second of exposure time.

The $\zeta$-potential and hydrodynamic diameter of the nanoparticles are shown in Table 2.

TABLE 2

| | $\zeta$-potential (mV) | Hydrodynamic diameter (nm) |
|---|---|---|
| AuNR | 36.6 ± 0.7 | 49.9 ± 0.9, 1.5 ± 0.1 |
| AuNR-PSS | −36.7 ± 1.1 | 63.37 ± 0.5, 2.8 ± 0.1 |
| AuNR-PSS Ag PANI (polyaniline) | −26.5 ± 0.3 | 73.0 ± 0.8, 3.1 ± 0.1 |
| AuNP | −26.8 ± 1.1 | 19.0 ± 0.8 |
| AuNP-ATP | −28.2 ± 1.2 | 33.3 ± 0.4 |
| AuNP-ATP Ag PANI (polyaniline) | −25.2 ± 0.7 | 72.6 ± 0.6 |

FIGS. 11A-11D shows the UV-Vis absorption spectra and hydrodynamic diameter of the Au nanoparticle, the PSS- or ATP-coated Au nanoparticle and the Janus nanostructure consisting of the Au core-Ag satellite bimetal part and the polymer part. As seen from FIG. 11A, the absorption spectrum of the AuNR was changed upon PSS binding. The localized surface plasmon resonance (LSPR) peak of the AuNR in the length direction was blue-shifted from 666 nm to 664 nm after the PSS coating, suggesting that the AuNR is partly surrounded by PSS and provides a reduction site. Aggregation or clustering of the AuNR did not occur during the process because no additional peak was observed. When the metal nanoparticle was completely coated with PSS, the redshift of the LSPR peak was observed due to the increase in the local dielectric function. However, the AuNR closely surrounded by PSS prevented silver ion from being reduced to the core metal nanoparticle. In contrast, insufficient PSS coating prompted the precipitation of the AuNR due to electrostatic interaction. In this regard, the adequate PSS concentration under an optimum condition was considered carefully. After the synthesis of the Janus nanostructure consisting of the Au core-Ag satellite bimetal part and the polymer part through an oxidation-reduction reaction between the silver ion and the aniline monomer, new Ag absorption peaks appeared in the range from 380 nm to 480 nm and the longitudinal and transverse LSPR peaks of the AuNR at 525 nm and 664 nm were blue-shifted to 508 nm and 595 nm, respectively. This change in the UV-Vis absorption was consistent with the color change of the MNP solution from blue to brown, suggesting the presence of the Au—Ag bimetal Janus nanostructure. In addition, the hydrodynamic diameter, size distribution and surface charge of the AuNR, the PSS-coated AuNR and the bimetal core-satellite Janus nanostructure thereof were analyzed by dynamic light scattering (DLS) and $\zeta$-potential measurement. As can be seen from FIG. 11B and Table 2, the longitudinal and transverse average diameters of the AuNR were 1.5±0.1 nm and 49.9±0.9 nm and the average diameter of the PSS-coated AuNR was 2.8±0.1 nm and 63.4±0.5 nm, respectively. In addition, the average diameter of the bimetal core-satellite Janus nanostructure was 3.1±0.1 nm and 73.0±0.8 nm due to the aspherical shape. The ζ-potential value of the AuNR, the PSS-coated AuNR and the bimetal core-satellite Janus nanostructure thereof was 36.6±0.7 nm, −36.7±1.1 nm and −26.5±0.3 nm, respectively. The ζ-potential of the PSS-coated AuNR decreased abruptly due to the presence of the negatively charged PSS on the surface of the AuNR. As the silver ion was reduced by an oxidation-reduction reaction as it was captured by the polymer ligand-bound AuNR, the ζ-potential value of the bimetal AuNR core-Ag satellite Janus nanostructure having the polymer part was decreased due to the decreased negative charge on the AuNR. Similarly, the citrate-capped AuNP was functionalized with the small ligand ATP to prepare the core-satellite Janus nanostructure. As seen from FIG. 11C, the UV-vis absorption peak of the citrate-capped AuNP at 524 nm was red-shifted to 526 nm, suggesting the adsorption of the ATP on the surface of the AuNP. After the synthesis of the bimetal core-satellite Janus nanostructure having the polymer part, the Ag plasmon peak and additional peaks appeared in the range from 400 to 550 nm due to the Au—Ag interface. In addition, as shown in FIG. 11D and Table 2, the average diameter of the AuNP, the ATP-coated AuNP and the bimetal core-satellite Janus nanostructure thereof was 19.0±0.8 nm, 33.3±0.4 nm and 72.6±0.6 nm, respectively and the ζ-potential value was −26.8±1.1 mV, −28.2±1.2 mV and −25.2±0.7 mV, respectively.

FIGS. 12A-12D shows the relative Raman shift of the MGITC-labeled AuNR core-Ag satellite as seen in FIG. 12A and the ATP-labeled AuNP core-Ag satellite as seen in FIG. 12C depending on the concentration of the Raman dye for optimization of the high-sensitivity SERS-based biosensing condition. The SERS intensity increased with the MGITC concentration in the range from $10^{-7}$ M to $10^{-5.5}$ M. However, the colloidal stability of the MGITC-labeled AuNR core-Ag satellite was decreased at the MGITC concentration of $10^{-5}$ M due to MGITC-induced aggregation. FIG. 12B shows the relative Raman shift of the bimetal AuNR core-Ag satellite and —Ag shell nanoparticles (Comparative Example 1) at the MGITC concentration of $10^{-5.5}$ M. The interparticle junction between the Ag satellite resulted in improved electromagnetic field and the SERS intensity was increased 5-fold due to the hot spot. Similarly, the relative Raman shift of the bimetal AuNP core-Ag satellite increased in the range from $10^{-6}$ M to $2.5 \times 10^{-6}$ M as shown in FIG. 12C. The SERS intensity of the nanostructure decreased significantly at the ATP concentration of $5.0 \times 10^{-6}$ M due to deposition. During the synthesis procedure, the satellite was formed on the ATP-coated AuNP surface and the ATP was buried in the gap between the AuNP core and the Ag satellite. Therefore, significant improvement of the electromagnetic field could be observed at the site where the Raman-active ATP was located, as shown in FIG. 12D.

FIGS. 13A-13H shows the transmission electron microscopy (TEM) images of the AuNR as shown in FIG. 13A, the bimetal AuNR core-Ag nanoparticle as shown in FIG. 13B and the bimetal AuNR core-Ag satellite at various magnifications as seen in FIGS. 13C-13H. The bimetal part consisting of the AuNR core and the Ag satellite is clearly seen and the polymer part is distinctly seen as gray against the background. The composition of the bimetal part was investigated by high-angle annular dark-field scanning TEM (HAADF-STEM). The AuNR core looked brighter than the Ag satellite due to the higher atomic number.

FIGS. 14A-14H shows the transmission electron microscopy (TEM) images of the AuNR as shown in FIG. 14, the bimetal AuNP core-Ag nanoparticle as shown in FIG. 14B and the bimetal AuNP core-Ag satellite at various magnifications as shown in FIGS. 14C-14H The bimetal part consisting of the AuNP core and the Ag satellite is clearly seen and the polymer part is distinctly seen as gray against the background. The composition of the bimetal part was investigated by high-angle annular dark-field scanning TEM (HAADF-STEM). The AuNP core looked brighter than the Ag satellite due to the higher atomic number.

<Example 5> Antibody Binding to Magnetic Bead and Janus Nanostructure Consisting of Au Core-Ag Satellite Bimetal Part and Polymer Part The Janus nanostructure consisting of the Au core-Ag satellite bimetal part and the polymer part and the magnetic bead were bound to two different sets of a monoclonal antibody (mAb) and a polyclonal antibody (pAb) for the target protein CEA (carcinoembryonic antigen). First, the polymer part of the Janus nanostructure consisting of the Au core-Ag satellite bimetal part and the polymer part was bioconjugated to the anti-human CEA polyclonal antibody (anti-human CEA pAb) through an amide coupling reaction between the amine group remaining in the poly(aniline) part and the carboxyl group present in the antibody. The coupling reaction was conducted using EDC (1-ethyl-3-(3-dimethylaminopropyl)carbodiimide) and sulfo-NHS (sulfo-N-hydroxysuccinimide ester). Specifically, after adding 5 μL of 2.0 mg/mL anti-human CEA pAb to a dispersion of the bimetal-polymer Janus nanoparticle containing 60 mM of EDC and 9.2 mM of sulfo-NHS in 10 mM PBS of pH 7.4, the mixture was stirred for 3 hours until the total pAb concentration was 10 pg/mL. The anti-human CEA pAb-conjugated Janus nanostructure was centrifuged at 3,000 rpm and then resuspended in PBS. Also, the magnetic bead was chemically bound to anti-human CEA mAb by activating the carboxyl group remaining on the polymer nanoparticle which was thermally stabilized overnight at 175° C. Specifically, 1.25 mg of the magnetic bead was suspended in 0.9 mL of PBS and then sonicated for 2 minutes using a tip sonicator at 20.0% amplitude with 3/3 sec on/off cycles. The uniformly suspended magnetic bead was mixed with 5.0 mM EDC and 5.0 mM sulfo-NHS and then stirred for 1 hour. 3.56 mg/mL anti-human CEA mAb diluted with 100 μL of PBS was slowly added to the magnetic bead solution to a final concentration of 8.9 pg/mL and the mixture was stirred for 1 hour. After removing the unbound anti-human CEA mAb using a magnetic field, the antibody-conjugated magnetic bead was resuspended in PBS for SERS-based biosensing of CEA.

<Example 6> SERS-Based Biosensing for Target Protein CEA Using Janus Nanostructure Consisting of Au Core-Ag Satellite Bimetal Part and Polymer Part and Magnetic Bead The Janus nanostructure consisting of the bimetal Au core-Ag satellite part and the polymer part labeled with the Raman reporter was used as an SERS nanoprobe for quantitative analysis of the target protein CEA. A sandwich immune complex was formed using the magnetic bead bound to anti-human CEA mAb. First, the magnetic bead with anti-human CEA mAb antibody bound was added to a buffer containing CEA at 3 different concentrations in the range from 22.5 to 67.5 ng/mL and then incubated for 1 hour. The target protein was washed with an external magnetic field and then resuspended in fresh PBS. Then, a sandwich immune complex consisting of the magnetic bead, the target protein and a SERS nanoprobe was prepared by adding a SERS nanoprobe with anti-human CEA pAb bound to the immune complex of the target protein and the magnetic bead and then incubating for 1 hour FIG. 10D. After removing the unbound SERS nanoprobe using a magnetic field, the produced sandwich immune complex was resuspended in PBS for SERS measurement. Also, experiment for a control group was conducted to evaluate the selective coupling performance of the SERS nanoprobe with no target protein bound.

FIGS. 15A-15B shows the Raman spectra and Raman intensity of the target depending on the concentration CEA. As the CEA concentration increased in the range from 22.5 to 67.5 pg/mL, the Raman intensity of the Janus nanostructure consisting of the MGITC-labeled Au core-Ag satellite bimetal part and the polymer part increased due to the formation of the sandwich immune complex. Control experiment was conducted without CEA. Also, the representative SERS peak intensity of MGITC at 1618 $cm^{-1}$ increased linearly with the CEA concentration ($R^2$=0.9954).

Invention 3

<Example 1> Preparation of Gold Nanocluster (AuNC)

A gold nanoparticle (AuNP) was synthesized by citrate reduction. Specifically, after adding a stock solution of gold(III) chloride hydrate ($HAuCl_4 \cdot 3H_2O$, Sigma-Aldrich, USA) to 100 mL of deionized water to a concentration of 0.01%, 1.5 mL of a 1% sodium citrate solution was added quickly while strongly stirring and boiling the solution. The solution turned red within 5 minutes, which suggests the reduction of gold ion, and the reaction was conducted further for 20 minutes. The resulting solution was cooled to room temperature. Also, an AuNP cluster was prepared by aggregating the AuNP in the presence of a Raman dye. In a glass vial, the seed AuNP was mixed with a stock solution of the Raman-active molecule MGITC (malachite green isothiocyanate, Invitrogen, USA), silver nitrate and sodium citrate to final concentrations of 1.5 µM or 0.75 µM MGITC, 0.5 mM silver nitrate and 1.0 mM sodium citrate. After stirring the mixture for 5 minutes, the vial was heated to 95° C. for 10-60 minutes. During the heating, small aliquots were recovered with predetermined intervals and the UV-Vis absorption bands and Raman intensity of the gold nanocluster having MGITC were measured. An AuNP cluster having RBITC (rhodamine B isothiocyanate, Sigma-Aldrich, USA) was prepared in the same manner to a final RBITC concentration of 3.8 µM or 1.9 µM. After sufficient clustering, the reaction solution was cooled rapidly to room temperature and 0.5% BSA was added to prevent aggregation by stabilizing the cluster.

<Example 2> Preparation of Asymmetric Janus Nanoprobe of Bimetal Nanocluster-Polymer An asymmetric Janus nanocluster-polymer nanoparticle consisting of an Au core-Ag shell bimetal nanocluster part and a poly(aniline) part was prepared through surface-templated polymerization based on an oxidation-reduction reaction. To prepare the Au core-Ag shell, 15 mL of the BSA-stabilized AuNP cluster solution of Example 1 was concentrated by centrifuging at 7,000 rpm for 5 minutes and the supernatant was removed. Aniline and SDS were dissolved in 7.5 mL of deionized water to final concentrations of 5 mM and 0.9 mM, respectively. After adding the concentrated AuNP cluster to the prepared solution and vortexing slightly, 2.5 mL of a silver nitrate solution was added to a final concentration of 2.5 mM. The reaction was conducted under a dark condition at room temperature for 24 hours without stirring. As a result, the Ag shell was formed on the Au core. Poly(aniline) was eccentrically deposited on only one side of the Au seed by incubating the reaction solution overnight in a 3.6 mM SDS solution. The surfactant SDS affected the interfacial tension between the two adjacent phases of poly(aniline)-Ag and poly(aniline)-water and a poly(aniline) part was formed on one side of the Au seed to minimize total surface energy. The resulting solution was purified by centrifuging at 8,000 rpm for 10 minutes and then resuspended in a 3.6 mM SDS solution to prevent aggregation.

The TEM images of the anisotropic Janus nanostructure containing the bimetal nanocluster induced by MGITC at a final concentration of 1.5 µM are shown in FIGS. 19A-19D. As seen from FIGS. 19A and 19B the Au core-Ag shell bimetal nanocluster was not formed well when the Au nanocluster was not coated with BSA. However, when the Au nanocluster was coated with BSA, the anisotropic Janus nanostructure consisting of the bimetal nanocluster part and the polymer part was formed as shown in FIGS. 19C and 19D. Similarly, an anisotropic Janus nanostructure was formed from an Au nanocluster induced by RBITC at a final concentration of 3.8 µM through an oxidation-reduction reaction.

FIGS. 20A and 20B show that the anisotropic Janus nanostructure was not formed when the Au nanocluster was not coated with BSA. However, when the MNP cluster was stabilized with BSA, the Janus nanostructure having an asymmetric polymer part was formed as shown in FIGS. 20C and 20D.

FIGS. 21A and 21B shows the TEM images of the asymmetric Janus nanocluster-polymer nanoparticle induced by MGITC at a final concentration of 0.75 µM. The concentration of the Raman dye was optimized to control the cluster size. When the MGITC at a low concentration was used to induce the aggregation of the AuNP, a few nanoclusters were observed. FIGS. 21A and 21B show the anisotropic Janus nanostructure not stabilized by BSA. When compared with the nanostructure prepared using 1.5 µM MGITC, the Janus nanostructure having the Janus nanocluster could be formed due to low metal clustering level even without BSA coating. As can be seen from FIGS. 21C and 21D there was no significant difference between the two nanostructures with or without BSA coating.

FIGS. 22A-22D shows the TEM images of the anisotropic Janus nanostructure containing the Janus nanocluster induced by RBITC at a final concentration of 1.9 µM. Similarly, the BSA coating had no effect on the formation of the anisotropic Janus nanostructure due to the low RBITC concentration.

<Example 3> Synthesis of Magnetic Nanoparticle (MNP) and Magnetic Bead Through Electrohydrodynamic (EHD) Jetting An iron oxide nanoparticle ($Fe_3O_4$) was prepared by chemical coprecipitation using a 1:2 (molar ratio) mixture of $Fe^{2+}$ and $Fe^{3+}$ in an ammonia water as a precipitating agent. 0.86 g of iron(II) chloride ($FeCl_2$) tetrahydrate and 2.35 g of iron(III) chloride ($FeCl_3$) were mixed in 40 mL of deionized water under vigorous stirring and degassed with nitrogen gas for 30 minutes. After heating the reaction solution to 80° C., 5 mL of ammonium hydroxide ($NH_4OH$) was added under mechanical stirring for 30 minutes. After adding 1 g of citric acid to a reaction flask and heating to 90° C., the reaction solution was stirred vigorously for 90 minutes. Finally, the $Fe_3O_4$ magnetic nanoparticle (MNP) was washed twice with deionized water under a static magnetic field of hundreds of Gauss. Also, a magnetic bead was prepared by concentrating a small aliquot of a MNP solution using a magnetic field and adding to a polymer solution. 4.5 w/v % of poly(acrylamide-co-acrylic acid) (poly(AAm-co-AA)) was prepared in a 3:1 (volume ratio) mixture of deionized water and ethylene glycol and the concentrated MNP was uniformly suspended in the polymer solution. For electrohydrodynamic (EHD) dispersion, the suspension of the dispersed MNP was put in a 1.0-mL syringe (BD, Franklin Lakes, USA) having a 23-gauge stainless steel capillary tube. To achieve a stable Taylor cone and a cone-jet mode, an optimized viscosity was obtained by dissolving the polymer in a viscous solvent such as ethylene glycol without increasing the polymer concentration. The microsyringe pump KDS-100 (KD Scientific, Inc., USA) allowing the flow of the MNP suspension at a constant rate was equipped at the syringe. A 0.018-mm thick aluminum foil (Fisherbrand; Thermo Fisher Scientific, USA) was used as a collecting plate. A high voltage was applied between the capillary tube connected to an anode and the aluminum foil connected to a cathode using the high-voltage power source NNC HV 30 (Nano NC, Korea). The distance between the two electrodes was 20-25 cm. The high voltage was maintained at 15-20 kV and the flow rate of the two solutions was maintained at 0.08-0.15 mL/hour. During the EHD jetting, the single-phase Taylor cone, jet stream and jet break-up were visualized and captured using a high-resolution digital camera (D-90, Nikon Corporation, Japan). After the EHD jetting, the formed magnetic bead was thermally crosslinked overnight at 175° C. Finally, the magnetic bead in the form of a powder was collected and used for the following experiments.

<Example 4> Characterization of Anisotropic Janus Nanostructure Consisting of Bimetal Nanocluster Part and Polymer Part The UV-Vis spectra of the asymmetric bimetal nanocluster-polymer Janus nanostructure were obtained in a wavelength range of 300-900 nm using a UV-Vis spectrophotometer (UV-1800, Shimadzu, Japan) in a single scan mode with a medium scan speed at room temperature with a fixed slit width of 1 nm. The baseline was calibrated using two cells filled with deionized water. The hydrodynamic diameter and size distribution of the colloid solution were characterized by dynamic light scattering (DLS) (Zeta-sizer Nano ZS90, Malvern Instruments, UK) equipped with a Ne—He laser at a wavelength of 633 nm and a maximum output power of 5 mW as a light source at a scattering angle of $90^2$. The temperature was controlled to 25° C. After diluting the sample 2-fold with deionized water at a volume ratio of 1:1, the average size was measured for at least 20 scan cycles. In addition, the zeta potential (ζ-potential) was measured for characterization of surface charge in deionized water. The individual AuNP and the asymmetric Janus nanocluster-polymer nanoparticle were analyzed by transmission electron microcopy using JEM-2100F FE-STEM (JEOL, Germany) operating at an accelerating voltage of 80-200 kV. The sample was deposited on a 400-mesh copper grid with ultrathin carbon coating (Ted Pella, Inc., USA). The average diameter, size distribution and surface morphology were measured by scanning electron microscopy (SEM) (VEGA-SB3, TESCAN, Czech Republic) operating at 0.5-30 kV with a focused beam. A small amount of the nanoparticle solution was placed on a silicon wafer and dried at room temperature. The sample was coated with a thin conductive platinum layer using a coater (K575X Turbo Sputter Coater, Emitech Ltd., UK). The average particle size was analyzed for about 50-100 particles randomly selected from the TEM and SEM images using the ImageJ software developed by the National Institutes of Health (USA). All SERS measurements were performed using a Renishaw inVia Raman microscope system equipped with a Renishaw He—Ne laser operating at a wavelength (λ) of 632.8 nm in response to a stimulation source having a laser output of 12.5 mW. The Rayleigh line was removed from the collected SERS spectra using a holographic notch filter located in the collection path. Raman scattering was collected using a charge-coupled device (CCD) camera at a spectral resolution of 1 $cm^{-1}$ and all the SERS spectra were calibrated to the 520 $cm^{-1}$ silicon line. The colloid solution of the RBITC- or MGITC-labeled nanoparticle was put in a small glass capillary tube (Kimble Chase, plain capillary tube, soda-lime glass, inner diameter: 1.1-1.2 mm, wall thickness: 0.2±0.02 mm, length: 75 mm). A 20× objective lens was used to focus the laser spot on the glass capillary tube in a wavelength range of 608-1738 $cm^{-1}$. The SERS spectra were collected for 1 second of exposure time.

The UV-Vis absorbance spectra of the AuNP, the Raman dye-induced Au nanocluster and the anisotropic Janus nanostructure having the bimetal nanocluster are shown in FIGS. 17A-17D. The UV-Vis absorption peak of the AuNP appeared at 510 nm FIG. 17A. When the AuNP solution was incubated for 10-90 minutes after adding MGITC, the original absorption peak was red-shifted and new absorption peaks appeared in the range of 650-850 nm. With increasing incubation time, the two peaks were red-shifted due to the aggregation of the AuNP. FIG. 17B shows the UV-Vis absorbance of the Au nanocluster induced by RBITC with different incubation times from 10 minutes to 90 minutes. Similarly to the MGITC-induced nanocluster, the peak was red-shifted with increasing incubation time. FIG. 17C shows the UV-Vis absorbance of the anisotropic Janus nanostructure having the bimetal nanocluster. After the synthesis of the bimetal nanocluster, new absorption peaks appeared in the range of 410-550 nm, suggesting the presence of Ag on the Au nanocluster. In addition, a broad peak appeared in the range of 600-700 nm due to the aggregation of the AuNP. Dynamic light scattering (DLS) was conducted to characterize the hydrodynamic diameter and size distribution of the AuNP, the Au nanocluster and the anisotropic Janus nanostructure, as shown in FIG. 17D. The average diameter of the AuNP and the MGITC- or RBITC-induced Au nanocluster was 18.9±0.4 nm, 152.9±2.8 nm and 115.7±1.8 nm and the average diameter of the anisotropic Janus nanostructure having the MGITC- or RBITC-induced bimetal nanocluster was 205±4.5 nm and 186.3±2.1 nm.

FIGS. 18A-18F shows the relative Raman spectra of the MGITC as seen in FIG. 18A- or RBITC as seen in FIG. 18C-induced Au nanocluster during the cluster formation at various incubation times from 10 minutes to 90 minutes for optimization of the clustering level for high SERS efficiency. The Raman dye concentration and BSA coating of the Au nanocluster were adjusted to control the cluster size and prevent further aggregation. The Raman intensity decreased gradually with increasing incubation time, suggesting that a larger aggregate was formed and precipitated. As can be seen from FIG. 18B and FIG. 18D, the Raman intensity of the MGITC- and RBITC-induced Au nanoclusters was 1618 cm$^{-1}$ and 1648 cm$^{-1}$. FIGS. 18E and 18F show the relative Raman spectra of the MGITC- or RBITC-labeled AuNP, the MGITC- or RBITC-induced Au nanocluster and the anisotropic Janus nanostructure thereof for the same Raman dye and particle concentration. The Raman intensity of the MGITC- and RBITC-induced Au nanoclusters was 10.42 and 2.32 times that of the AuNP, suggesting that the interparticle coupling between the AuNP cluster greatly improves SERS efficiency due to the hot spot. Also, the Raman intensity of the anisotropic Janus nanostructure having the MGITC- or RBITC-induced bimetal nanocluster was 8.87 and 1.82 times that of the Raman dye-labeled AuNP. When compared with the Raman intensity of the MGITC- and RBITC-induced Au nanoclusters, the Raman intensity of the anisotropic Janus nanostructure was slightly decreased. The anisotropic Janus nanostructure having the MGITC- or RBITC-induced bimetal nanocluster exhibits superior optical signals as compared to the MGITC- or RBITC-labeled AuNP for the same Raman dye and particle concentration.

<Example 5> Antibody Binding to Anisotropic Janus Nanostructure Consisting of Bimetal Nanocluster Part and Polymer Part The asymmetric bimetal nanocluster-polymer Janus nanostructure was bound respectively to a monoclonal antibody (mAb) and a polyclonal antibody (pAb) for the target protein CEA (carcinoembryonic antigen). First, the polymer part was bioconjugated to the anti-human CEA polyclonal antibody (anti-human CEA pAb) through an amide coupling reaction between the amine group remaining in the poly (aniline) part and the carboxyl group present in the antibody. The coupling reaction was conducted using EDC (1-ethyl-3-(3-dimethylaminopropyl)carbodiimide) and sulfo-NHS (sulfo-N-hydroxysuccinimide ester). Specifically, after adding 5 μL of 2.0 mg/mL anti-human CEA pAb to a dispersion of the anisotropic Janus nanostructure containing 60 mM of EDC and 9.2 mM of sulfo-NHS in 10 mM PBS of pH 7.4, the mixture was stirred for 3 hours until the total pAb concentration was 10 pg/mL. The anti-human CEA pAb-conjugated polymer part was centrifuged at 3,000 rpm and then resuspended in PBS. Also, the magnetic bead was chemically bound to anti-human CEA monoclonal antibody (anti-human CEA mAb) by activating the carboxyl group remaining on the polymer nanoparticle which was thermally stabilized overnight at 175° C. Specifically, 1.25 mg of the magnetic bead was suspended in 0.9 mL of PBS and then sonicated for 2 minutes using a tip sonicator at 20.0% amplitude with 3/3 sec on/off cycles. The uniformly suspended magnetic bead was mixed with 5.0 mM EDC and 5.0 mM sulfo-NHS and then stirred for 1 hour. 3.56 mg/mL anti-human CEA mAb diluted with 100 μL of PBS was slowly added to the magnetic bead solution to a final concentration of 8.9 pg/mL and the mixture was stirred for 1 hour. After removing the unbound anti-human CEA mAb using a magnetic field, the antibody-conjugated magnetic bead was resuspended in PBS for SERS-based biosensing of CEA FIG. 16C.

<Example 6> SERS-Based Biosensing Using Anisotropic Janus Nanostructure

The anisotropic Janus nanostructure labeled with the Raman reporter was used as an SERS nanoprobe for quantitative analysis of the target protein CEA. A sandwich immune complex was formed using the magnetic bead bound to anti-human CEA mAb. First, the magnetic bead with anti-human CEA monoclonal antibody bound was added to a buffer containing CEA at 3 different concentrations in the range from 22.5 to 67.5 ng/mL and then incubated for 1 hour. The target protein was washed with an external magnetic field and then resuspended in fresh PBS. Then, a sandwich immune complex consisting of the magnetic bead, the target protein and a SERS nanoprobe was prepared by adding a SERS nanoprobe with anti-human CEA pAb bound to the immune complex of the target protein and the magnetic bead and then incubating for 1 hour. After removing the unbound SERS nanoprobe using a magnetic field, the produced sandwich immune complex was resuspended in PBS for SERS measurement. Also, experiment for a control group was conducted to evaluate the selective coupling performance of the SERS nanoprobe with no target protein bound.

Invention 4

<Example 1> Synthesis of Bimetal Nanorod Cluster Through Side-by-Side Assembly

A side-by-side assembled gold nanorod (AuNR) cluster was prepared by adding citrate anion for electrostatic interaction with the positively charged CTAB (hexadecyltrimethylammonium bromide) on the AuNR. The AuNR was synthesized by the seed-mediated growth method. Specifically, after dissolving 5 mL of 0.20 M CTAB at 29-30° C. and mixing with 5 mL of 0.0005 M gold(III) chloride hydrate (HAuCl$_4$·3H$_2$O), 0.010 mL of cold 0.010 M NaBH$_4$ was added. A seed solution produced as the color of the reaction solution changed from yellow to yellowish brown was maintained at 29-30° C. and used within 2-2.5 hours. In order to grow a nanorod on the seed particle, 0.25 mL of 0.004 M AgNO$_3$ and 0.20 M CTAB were mixed at 29-30° C. Then, the solution was stirred after adding 5.0 mL of 0.001 M HAuC14. After mixing for 30-40 minutes, the color change of the growth solution was induced from deep yellow to colorless by adding the reducing agent ascorbic acid. In the final stage, 12 μL of the seed solution was added to the colorless solution and then the color of the solution was slowly changed in 10-20 minutes. The solution was stirred and stored overnight at 29-30° C. The resulting solution was centrifuged at 10,000 rpm for 10 minutes and then resuspended in 1 mM CTAB to prevent AuNR aggregation. Finally, a CTAB-capped AuNR was prepared. MGITC was added to the AuNR solution to a final concentration of 10$^{-6}$ M. The MGITC was immobilized onto the surface of the AuNR through the isothiocyanate group (—N=C=S) of the MGITC. For side-by-side assembly of the AuNR, 30 μL of a 0.175 mM sodium citrate solution was added to 1 mL of the AuNR solution and incubation was performed for 1-5 minutes. The AuNR cluster side-by-side self-assembled through the electrostatic interaction between the citrate anion and the CTAB cation was stabilized by coating with 200 μL of 1 w/v % PSS FIG. 24A.

<Example 2> Synthesis of Diblock Poly(AAc-b-NIPAM)

Poly(AAc-b-NIPAM) (poly(acrylic acid-block-N-isopropylacrylamide)), which is a negatively charged stimulation-responsive copolymer and a diblock polymer, was synthesized by RAFT (sequential reversible addition-fragmentation chain transfer) polymerization followed by hydrolysis of the tBA group of poly(tBA-b-NIPAM) (poly(tert-butyl acrylate-block-N-isopropylacrylamide). A NIPAM monomer was dissolved at 40° C. in n-hexane and then recrystallized at 4° C. or lower to remove impurities including inhibitors. 10 g of NIPAM was dissolved in 200 mL of n-hexane in a beaker to a concentration of 5 w/v %. When crystalline NIPAM was formed at the low temperature, the solution was filtered through a filter paper (Whatman qualitative filter paper, grade 1) and the n-hexane was removed by drying the product in vacuo using a rotary evaporator (EYELA 1000S, US). tBA was purified by distilling at 40° C. and 26 mmHg to remove polymerization inhibitors.

Poly(tBA), or poly(tBA)-macro CDTPA(4-cyano-4-[(dodecylsulfanylthiocarbonyl)sulfanyl]pentanoic acid), was synthesized by RAFT polymerization of tBA by adding tBA (tert-butyl acrylate) as a monomer, CDTPA as a CTA (chain transfer agent) and AIBN (azobisisobutyronitrile, 2,2'-azobis(2-methylpropionitrile)) as an initiator at a molar ratio of [monomer]:[CTA]:[initiator]=1000:10:1 in 1,4-dioxane as a reaction solvent. Specifically, tBA (5 mL, 34 mmol), CDTPA (0.137 g, 0.34 mmol) and 1,4-dioxane (5 mL) were added to a Schlenk flask. Before conducting polymerization, the solution was degassed with nitrogen gas for 20 minutes. Polymerization was initiated by adding AIBN (0.0055 g, 0.034 mmol) to the reaction mixture. After conducting polymerization while mechanically stirring at 60° C. for 5 hours or 6 hours, the reaction mixture was quenched in ice water. The produced poly(tBA)-macro CDTPA was obtained by precipitating in a methanol:$H_2O$ (50:50 (v/v)) solution and then dired overnight in a vacuum oven.

Poly(tBA-b-NIPAM) was prepared in a similar manner. For the synthesis of poly(tBA-b-NIPAM), NIPAM (N-isopropylacrylamide 97%) as a monomer, poly(tBA)-macro CDTPA as a CTA and AIBN as an initiator were added at a molar ratio of [monomer]:[CTA]:[initiator]=1500:5:1. Specifically, 0.411 g of poly($tBA_{145}$)-macro CDTPA ($M_n^{NMR}$=18,584 g/mol) and 0.75 g of NIPAM were dissolved in 2.5 mL of 1,4-dioxane and then degassed with nitrogen gas for 20 minutes. Polymerization was conducted at 60° C. for 6 hours after adding 0.00075 g of AIBN to the solution. After stopping the reaction by immersing the flask in ice water, the solution was exposed to air. In order to remove the unreacted monomer and initiator, the poly($tBA_{145}$-b-$NIPAM_{300}$) solution was purified by precipitating in ether and then dried overnight in a vacuum oven.

Because the thiocarbonylthio group exists as a masked thiol group (—SH), the trithiocarbonate group of the poly(tBA-b-NIPAM) was cleaved by aminolysis using a nucleophilic reagent for coupling of the thiol group. Specifically, poly(tBA-b-NIPAM) (0.5 g, 9.5 μmol), MTS (18 μL, 190 μmol), hexylamine (252 μL, 1.9 mmol) and trimethylamine (266 μL, 1.9 mmol) were dissolved in 5 mL of THF (tetrahydrofuran) and the mixture was stirred at room temperature for 24 hours. The prepared thiol-terminated poly($tBA_{145}$-b-$NIPAM_{300}$) (poly($tBA_{145}$-b-$NIPAM_{300}$)-SH) was precipitated 3 times in hexane and then dried overnight in a vacuum oven FIG. 26A.

Thiol-terminated poly($AAc_{145}$-b-$NIPAM_{300}$) (poly($AAc_{145}$-b-$NIPAM_{300}$)-SH) was prepared by hydrolyzing tBA in thiol-terminated poly($tBA_{145}$-b-$NIPAM_{300}$) (poly($tBA_{145}$-b-$NIPAM_{300}$)-SH) with an AAc group using TFA (trifluoroacetic acid). Specifically, 0.2 g of thiol-terminated poly($tBA_{145}$-b-$NIPAM_{300}$) (poly($tBA_{145}$-b-$NIPAM_{300}$)-SH) (3.8 μmol) and 583 μL of TFA (7.6 mmol) were dissolved in 5 mL of DCM (dichloromethane). 24 hours later, a bright brown gelatin lump was formed and precipitated from the solution. The product was dissolved in DCM and then precipitated in n-hexane. Finally, the product was dissolved in THF and dialyzed for 2 days in deionized water. The obtained thiol-terminated poly($AAc_{145}$-b-$NIPAM_{300}$) (poly($AAc_{145}$-b-$NIPAM_{300}$)-SH) was freeze-dried in vacuo using the freeze dryer MCFD8508 (Ilshin Lab, Korea) FIG. 26B <Example 3> Synthesis of Bimetal Nanorod Cluster Through End-to-End Assembly An end-to-end assembled AuNR cluster was prepared by selectively attaching the poly($AAc_{145}$-b-$NIPAM_{300}$)-SH of Example 2 to the end portion of the CTAB-capped AuNR of Example 1. Specifically, 4 mL of the CTAB-capped AuNR solution was centrifuged at 10,000 rpm for 10 minutes and then resuspended in 0.5 mL of deionized water. The concentrated CTAB-capped AuNR was quickly injected to 10 mL of DMSO containing 5 mg of the poly($AAc_{145}$-b-$NIPAM_{300}$)-SH to a final concentration of 0.05 w/v %. The mixture solution was sonicated for 30 minutes and then incubated at room temperature for 1 hour. The CTAB ligand attached to the end portion of the AuNR was exchanged with poly($AAc_{145}$-b-$NIPAM_{300}$)-SH through the binding between the thiol group (—SH) in the poly($AAc_{145}$-b-$NIPAM_{300}$)-SH and the metal. Then, the end-to-end self-assembly was formed by binding between the side portion of the AuNR and the end portion of the AuNR through electrostatic interaction between the positively charged CTAB on the side portion of the AuNR and the poly($AAc_{145}$-b-$NIPAM_{300}$)-SH on the end portion of the AuNR in deionized water or PBS at 20° C. or 50° C. The end-to-end self-assembled AuNR cluster was purified by centrifuging at 6,000 rpm for 6 minutes and then resuspended in 1 mL of deionized water. MGITC was introduced to the AuNR solution to a final concentration of $10^{-5}$ M and then fixed onto the AuNR surface through the isothiocyanate group (—N=C=S) of the MGITC. The end-to-end assembled AuNR was stabilized by coating with 0.5% BSA (bovine serum albumin) FIG. 24B.

<Example 4> Synthesis of Anisotropic Bimetal Nanorod Cluster-Polymer Janus Nanostructure An anisotropic Janus nanostructure consisting of a bimetal nanorod cluster and a polymer (poly(aniline)) part was synthesized by surface-templated polymerization of aniline and reduction of silver. A side-to-side or end-to-end assembled AuNR cluster was used as a seed particle. Specifically, aniline and SDS were dissolved in 0.5 mL of deionized water to final concentrations of 5 mM and 0.9 mM, respectively. After adding the seed particle solution to the mixture and vortexing, 0.5 mL of a silver nitrate solution was added to a final concentration of 2.5 mM. The reaction was conducted under a dark condition at room temperature for 24 hours without stirring. A poly(aniline) part was eccentrically deposited on only one side of the Au seed by incubating the reaction solution overnight in a 3.6 mM SDS solution. The resulting solution was purified by centrifuging at 8,000 rpm for 10 minutes and then resuspended in deionized water or 10 mM PBS (phosphate buffer saline).

<Comparative Example 1> Preparation of AuNR Cluster-Free Bimetal Nanorod-Polymer Janus Nanoparticle An AuNR cluster-free bimetal nanorod-polymer Janus nanoparticle was prepared in the same manner as in Example 4, except that a general AuNR solution was used as a stock solution of the seed particle.

The prepared AuNR cluster-free bimetal nanorod-polymer Janus nanoparticle was used as a control group.

<Example 5> Synthesis of Magnetic Nanoparticle (MNP) and Magnetic Bead Through Electrohydrodynamic (EHD) Jetting An iron oxide nanoparticle ($Fe_3O_4$) was prepared by chemical coprecipitation using a 1:2 (molar ratio) mixture of $Fe^{2+}$ and $Fe^{3+}$ in an ammonia water as a precipitating agent. 0.86 g of iron(II) chloride ($FeCl_2$) tetrahydrate and 2.35 g of iron(III) chloride ($FeCl_3$) were mixed in 40 mL of deionized water under vigorous stirring and degassed with nitrogen gas for 30 minutes. After heating the reaction solution to 80° C., 5 mL of ammonium hydroxide ($NH_4OH$) was added under mechanical stirring for 30 minutes. After adding 1 g of citric acid to a reaction flask and heating to 90° C., the reaction solution was stirred vigorously for 90 minutes. The $Fe_3O_4$ magnetic nanoparticle (MNP) was washed twice with deionized water under a static magnetic field of hundreds of Gauss. Also, a magnetic bead was prepared through electrohydrodynamic (EHD) jetting by concentrating a small aliquot of a MNP solution using a magnetic field and adding to a polymer solution. 4.5 w/v % of poly(acrylamide-co-acrylic acid) (poly(AAm-co-AA)) was prepared in a 3:1 (volume ratio) mixture of deionized water and ethylene glycol and the concentrated MNP was uniformly suspended in the polymer solution. For EHD dispersion, the suspension of the dispersed MNP was put in a 1.0-mL syringe (BD, Franklin Lakes, USA) having a 23-gauge stainless steel capillary tube. To achieve a stable Taylor cone and a cone-jet mode, an optimized viscosity was obtained by dissolving the polymer in a viscous solvent such as ethylene glycol without increasing the polymer concentration. The microsyringe pump KDS-100 (KD Scientific, Inc., USA) allowing the flow of the MNP suspension at a constant rate was equipped at the syringe. A 0.018-mm thick aluminum foil (Fisherbrand; Thermo Fisher Scientific, USA) was used as a collecting plate. A high voltage was applied between the capillary tube connected to an anode and the aluminum foil connected to a cathode using the high-voltage power source NNC HV 30 (Nano NC, Korea). The distance between the two electrodes was 20-25 cm. The high voltage was maintained at 15-20 kV and the flow rate of the two solutions was maintained at 0.08-0.15 mL/hour. During the EHD jetting, the single-phase Taylor cone, jet stream and jet break-up were visualized and captured using a high-resolution digital camera (D-90, Nikon Corporation, Japan). After the EHD jetting, the formed magnetic bead was thermally crosslinked overnight at 175° C. The magnetic bead in the form of a powder was collected from the foil and used for the following experiments.

<Example 6> Antibody Binding to Anisotropic Bimetal Nanorod Cluster-Polymer Janus Nanostructure and Magnetic Bead The anisotropic Janus nanostructure and the magnetic bead were bound respectively to a monoclonal antibody (mAb) and a polyclonal antibody (pAb) for the target protein CEA (carcinoembryonic antigen). First, the anti-human CEA polyclonal antibody (anti-human CEA pAb) was introduced to the poly(aniline) part of the Janus nanostructure through an amide coupling reaction between the amine group present in the poly(aniline) part and the carboxyl group present in the antibody. The coupling reaction was conducted using EDC (1-ethyl-3-(3-dimethylaminopropyl) carbodiimide) and sulfo-NHS (sulfo-N-hydroxysuccinimide ester). After adding 5 μL of 2.0 mg/mL anti-human CEA pAb to the nanostructure solution containing 60 mM of EDC and 9.2 mM of sulfo-NHS in 10 mM PBS of pH 7.4, the mixture was stirred for 3 hours until the total pAb concentration was 5 pg/mL. The anti-human CEA pAb-conjugated Janus nanostructure was centrifuged at 3,000 rpm and then resuspended in PBS. Also, the magnetic bead was chemically bound to anti-human CEA monoclonal antibody (anti-human CEA mAb) by activating the carboxyl group remaining on the polymer nanoparticle which was thermally stabilized overnight at 175° C. Specifically, 1.25 mg of the magnetic bead was suspended in 0.9 mL of PBS and then sonicated for 2 minutes using a tip sonicator at 20.0% amplitude with 3/3 sec on/off cycles. The uniformly suspended magnetic bead was mixed with 5.0 mM EDC and 5.0 mM sulfo-NHS and then stirred for 1 hour. 3.56 mg/mL anti-human CEA mAb diluted with 100 μL of PBS was slowly added to the magnetic bead solution to a final concentration of 8.9 pg/mL and the mixture was stirred for 1 hour. After removing the unbound anti-human CEA mAb using a magnetic field, the antibody-conjugated magnetic bead was resuspended in PBS for SERS-based biosensing of CEA.

<Example 7> SERS-Based Biosensing for Target Protein CEA Using Anisotropic Bimetal Nanorod Cluster-Polymer Janus Nanostructure and Magnetic Bead The anisotropic Janus nanostructure labeled with the Raman reporter was used as an SERS nanoprobe for quantitative analysis of the target protein CEA. A sandwich immune complex was formed using the magnetic bead bound to anti-human IgG mAb or anti-human CEA mAb. First, the magnetic bead with anti-human IgG monoclonal antibody or anti-human CEA monoclonal antibody bound was added to a buffer containing IgG or CEA at 3 different concentrations in the range from 2.5 to 67.5 ng/mL and then incubated for 1 hour. The target protein was washed with an external magnetic field and then resuspended in fresh PBS. Then, a sandwich immune complex consisting of the magnetic bead, the target protein and a SERS nanoprobe was prepared by adding a SERS nanoprobe with anti-human IgG pAb or anti-human CEA pAb bound to each immune complex of the target protein and the magnetic bead and then incubating for 1 hour. After removing the unbound SERS nanoprobe using a magnetic field, the produced sandwich immune complex was resuspended in PBS for SERS measurement. Also, experiment for a control group was conducted to evaluate the selective coupling performance of the SERS nanoprobe with no target protein bound.

<Example 8> Characterization of Diblock Poly(AAc-b-NIPAM)

The chemical composition of the poly(AAc-b-NIPAM) of Example 2 was analyzed by $^1H$ nuclear magnetic resonance ($^1H$ NMR) (AVANCE III 400, Bruker BioSpin AG, Fallennden, Switzerland) operating at a frequency of 400 MHz using dimethyl sulfoxide-$d_6$ and chloroform-d ($CDCl_3$) as solvents. The apparent molar ratio of the poly(AAc-b-NIPAM) was determined by comparing the relative peak signals of proton corresponding to respective monomers. For measurement of number-average molecular weight, weight-average molecular weight and polydispersity index, gel-permeation chromatography (GPC) measurement was performed using the high-performance liquid chromatography (HPLC) 1260 series apparatus (Agilent Technologies, Palo Alto, CA, USA) using the Shodex GPC column KF-803 (Shodex GPC system-21; Showa Denko Co., Tokyo, Japan). THF and polystyrene of 1,270-139,000 g/mol were used as a mobile phase with a flow rate of 1.0 mL/min and a stationary phase, respectively.

The thermal properties of the poly(AAc-b-NIPAM) were investigated by measuring the UV absorbance of the poly (AAc-b-NIPAM) solution and the hydrodynamic diameter of micellar structures in phosphate buffer was determined depending on temperatures. A sample was prepared by dissolving the poly(AAc-b-NIPAM) in PBS to a concentration of 0.05 w/v %. The lower critical solution temperature (LCST) of the poly(AAc-b-NIPAM) was measured by monitoring the absorbance of the poly(AAc-b-NIPAM) solution at 350 nm using the UV-Vis spectrophotometer Cary-100 Bio (Varian Biotech, US) equipped with a Peltier temperature controller. The measurement was made in the temperature range of 20-70° C. at a heating rate of 1° C./min. The hydrodynamic diameter of the poly(AAc-b-NIPAM) depending on temperature was measured by dynamic light scattering (DLS) (Zeta-sizer Nano ZS90, Malvern Instruments, Malvern, UK).

The cleavage of the trithiocarbonate group was analyzed by investigating the UV absorbance of the sample using a UV-Vis spectrophotometer (UV-1800, Shimadzu, Japan). The poly(tBA-b-NIPAM)-macro CDTPA and the poly(AAc-b-NIPAM)-SH were dissolved in $CHCl_3$ to a concentration of 0.5 w/v %. Each sample was scanned in the wavelength range of 200-700 nm.

The number-average molecular weight ($M_n^{GPC}$), weight-average molecular weight ($M_w^{GPC}$) and polydispersity index (PDI) of the poly($tBA_{145}$) and the poly($tBA_{145}$-b-$NIPAM_{300}$) are shown in Table 3.

TABLE 3

| | [Monomer]:[CTA]:[initiator] | Retention time (hr) | $M_n^{NMR}$ (g/mol) | $M_n^{GPC}$ (g/mol) | $M_w^{GPC}$ (g/mol) | PDI |
|---|---|---|---|---|---|---|
| Poly($tBA_{145}$) | 1000:10:1 | 5 | 18,584 | 21,152 | 25,593 | 1.21 |
| Poly($tBA_{145}$-b-$NIPAM_{300}$) | 1500:5:1 | 6 | 52,532 | 55,863 | 70,946 | 1.27 |

FIG. 27A shows the 400 MHz $^1$H NMR spectra of the poly(tBA) and the poly(tBA-b-NIPAM) measured in $CDCl_3$ and of the poly(AAc-b-NIPAM) measured in DMSO-d6. The peak at 1.45 ppm corresponds to the terminal methyl proton of the tBA block and the single peak at 3.9 ppm corresponds to the C-2 proton of the isopropyl group on the NIPAM block. After the tBA group was hydrolyzed with the AAc group, the methyl ester proton peak at 1.45 ppm disappeared, suggesting that all the ester groups of the poly(tBA-b-NIPAM) were converted to acrylic acids. FIG. 27B and Table 3 show the GPC trace of the poly(tBA) and poly(tBA-b-NIPAM) for measuring the molecular weight, polydispersity index and copolymer distribution depending on retention time using THF as a mobile phase. The poly ($tBA_{145}$) had a weight-average molecular weight of 25,593 g/mol and a PDI of 1.21 and the poly($tBA_{145}$-b-$NIPAM_{300}$) had a weight-average molecular weight of 70,946 g/mol and a PDI of 1.27. FIG. 27C shows the UV-Vis absorption spectra of the poly(tBA-b-NIPAM) before and after aminolysis. After the thiocarbonylthio group was removed through the aminolysis, the absorption peak at 307 nm disappeared. FIG. 27D shows the intrinsic thermal deformation characteristics of the poly(AAc-b-NIPAM) measured from UV absorbance and dynamic light scattering depending on temperature. The poly(NIPAM)-based copolymer or block copolymer was soluble below the LCST (lower critical solution temperature) but was insoluble due to hydrophobic interaction at or above the LCST. The LCST of the copolymer was determined as the temperature at which the temperature-dependent UV absorbance reached maximum. The poly(AAc-b-NIPAM) exhibited an LCST of 39.5° C. when the final concentration in 10 mM PBS was 0.05 w/v %. The hydrodynamic diameter of the poly(AAc-b-NIPAM) below the LCST was 12.05 nm and the diameter at or above the LCST was 39.2 nm.

<Example 9> Characterization of Asymmetric Nanorod Cluster-Polymer Janus Nanostructure The UV-Vis spectra of the anisotropic Janus nanostructure were obtained in a wavelength range of 300-900 nm using a UV-Vis spectrophotometer (UV-1800, Shimadzu, Japan) in a single scan mode with a medium scan speed at room temperature with a fixed slit width of 1 nm. The baseline was calibrated using two cells filled with deionized water. The hydrodynamic diameter and size distribution of the colloid solution were characterized by dynamic light scattering (DLS) (Zeta-sizer Nano ZS90, Malvern Instruments, UK) equipped with a Ne—He laser at a wavelength of 633 nm and a maximum output power of 5 mW as a light source at a scattering angle of $90^2$. The temperature was controlled to 25° C. After diluting the sample 2-fold with deionized water at a volume ratio of 1:1, the average size was measured for at least 20 scan cycles. In addition, the zeta potential (ζ-potential) was measured for characterization of surface charge in deionized water. The individual AuNP and the asymmetric Janus nanocluster-polymer nanoparticle were analyzed by transmission electron microcopy using JEM-2100F FE-STEM (JEOL, Germany) operating at an accelerating voltage of 80-200 kV. The sample was deposited on a 400-mesh copper grid with ultrathin carbon coating (Ted Pella, Inc., USA). The average diameter, size distribution and surface morphology were measured by scanning electron microscopy (SEM) (VEGA-SB3, TESCAN, Czech Republic) operating at 0.5-30 kV with a focused beam. A small amount of the nanoparticle solution was placed on a silicon wafer and dried at room temperature. The sample was coated with a thin conductive platinum layer using a coater (K575X Turbo Sputter Coater, Emitech Ltd., UK). The average particle size was analyzed for about 50-100 particles randomly selected from the TEM and SEM images using the ImageJ software developed by the National Institutes of Health (USA). All SERS measurements were performed using a Renishaw inVia Raman microscope system equipped with a Renishaw He—Ne laser operating at a wavelength (λ) of 632.8 nm in response to a stimulation source having a laser output of 12.5 mW. The Rayleigh line was removed from the collected SERS spectra using a holographic notch filter located in the collection path.

Raman scattering was collected using a charge-coupled device (CCD) camera at a spectral resolution of 1 cm$^{-1}$ and all the SERS spectra were calibrated to the 520 cm$^{-1}$ silicon line. The colloid solution of the MGITC-labeled nanoparticle was put in a small glass capillary tube (Kimble Chase, plain capillary tube, soda-lime glass, inner diameter: 1.1-1.2 mm, wall thickness: 0.2±0.02 mm, length: 75 mm). A 20× objective lens was used to focus the laser spot on the glass capillary tube in a wavelength range of 608-1738 cm$^{-1}$. The SERS spectra were collected for 1 second of exposure time.

The hydrodynamic diameter and zeta potential of the side-by-side assembled AuNR nanocluster and the anisotropic Janus nanostructure containing the same prepared by adding citrate anion to the AuNR solution and varying incubation time (citrate anion incubation time: 1-5 minutes) are shown in Table 4.

ture thereof. FIG. 25B and Table 4 show the hydrodynamic diameter of the original AuNR and the side-by-side assembled nanocluster when the incubation time was increased from 1 to 5 minutes. The longitudinal and transverse average diameters of the AuNR were 1.1±0.1 nm and 46.8±0.1 nm, respectively. When citrate anion was added to the AuNR solution, both the longitudinal and transverse diameters of the AuNR were increased as the incubation time was increased from 0 to 5 minutes. After PSS coating of the side-by-side assembled AuNR, the longitudinal and transverse average diameters of the nanocluster were 7.4±0.6 nm and 92.1±2.5 nm, respectively. The ζ-potential value of the original AuNR and the side-by-side assembled AuNR was 31.1±1.3 mV and −41.4±0.4 mV, respectively. The dramatic change in the surface charge of the AuNR cluster was due to the presence of the negatively charged

TABLE 4

| | Side-by-side assembled AuNR nanocluster Incubation time (min) | | | | | Anisotropic hybrid nanoparticle |
|---|---|---|---|---|---|---|
| | 0 | 1 | 2 | 3 | 5 | |
| Hydrodynamic diameter (nm) | Transverse: 46.8 ± 0.1, Longitudinal: 1.1 ± 0.1 | Transverse: 68.2 ± 2.5, Longitudinal: 3.7 ± 0.5 | Transverse: 99.8 ± 3.0, Longitudinal: 8.9 ± 0.7 | Transverse: 87.6 ± 1.1, Longitudinal: 6.4 ± 0.2 | Transverse: 92.1 ± 2.5, Longitudinal: 7.4 ± 0.6 | 78.6 ± 0.2 |
| ζ-potential (mV) | 31.1 ± 1.33 | N/A* | N/A* | N/A* | −41.4 ± 0.4 | −7.8 ± 0.3 |

*N/A: not available.

The hydrodynamic diameter of the AuNR (original AuNP), the end-to-end assembled AuNR nanocluster and the anisotropic Janus nanostructure containing the same are shown in Table 5. The AuNR cluster and the anisotropic Janus nanostructure were self-assembled in deionized water (DW) at room temperature or in PBS at different temperatures.

polymer electrolyte PSS. As seen from FIG. 25C, after oxidation polymerization to poly(aniline) on the side-by-side assembled anisotropic AuNR cluster and silver deposition, new Ag absorption peaks appeared in the range of 330-450 nm and the longitudinal plasmon peak was red-shifted as compared to the Janus nanoparticle having the original AuNR as a seed, suggesting the presence of the

TABLE 5

| | DW (RT) | | PBS (20° C.) | | PBS (50° C.) | |
|---|---|---|---|---|---|---|
| | Original AuNP | end-to-end assembled AuNR nanocluster | Anisotropic hybrid nanoparticle | end-to-end assembled AuNR nanocluster | Anisotropic hybrid nanoparticle | end-to-end assembled AuNR nanocluster | Anisotropic hybrid nanoparticle |
| Hydrodynamic diameter (nm) | Transverse: 60.9 ± 0.5, Longitudinal: 2.0 ± 0.1 | Transverse: 499.5, 101.8, Longitudinal: 5.1 | 388 | Transverse: 455.3, Longitudinal: 57.9 | 735 | Transverse: 329.7, Longitudinal: 46.0 | 590 |

FIG. 25 shows the UV-Vis absorbance spectra and hydrodynamic diameter of the side-by-side assembled AuNR and the anisotropic Janus nanostructure containing the same. During the side-by-side assembly of the AuNR, the longitudinal plasmon peak was blue-shifted from 700 nm to 610 nm with a decreased intensity as the incubation time was increased from 1 minute to 5 minutes as shown in FIG. 25A. In contrast, the transverse peak was slightly red-shifted from 510 nm to 525 nm with an increased intensity. The degree of the shift of the longitudinal and transverse peaks of the AuNR was correlated with the clustering level. This change in the plasmon absorption peak is caused by the plasmon coupling during the directional side-by-side assembly of the AuNR. In addition, dynamic light scattering (DLS) measurement was conducted to investigate the hydrodynamic diameter, size distribution and colloidal stability of the side-by-side self-assembled AuNR and the Janus nanostrucbimetal Au core-Ag shell nanorod cluster part. FIG. 25D shows the hydrodynamic diameter of the anisotropic bimetal nanorod cluster-polymer Janus nanostructure through side-by-side assembly of the AuNR. The average diameter of the Janus nanostructure was 78.6±0.2 nm and that of the nanoparticle cluster containing the original AuNR as a seed was 93.2±2.3 nm.

FIGS. 28A-28D shows the UV-Vis absorbance spectra and hydrodynamic diameter of the end-to-end assembled AuNR and the anisotropic Janus nanostructure containing the same. During the end-to-end assembly of the AuNR, the plasmon absorption peak in the longitudinal direction was red-shifted from 645 nm to 660 nm, but the transverse peak was hardly changed, as shown in FIG. 28A. This change occurred as dipoles were alternatingly connected along the AuNR chain. When the AuNR was end-to-end assembled in PBS at 20° C., a shoulder peak appeared at about 800 nm, suggesting that the nanocluster was partly aggregated under the high ionic strength of PBS due to decreased electrostatic repulsion between the CTAB bilayer. At 50° C., which is higher than the LCST of the poly(AAc-b-NIPAM), the plasmon absorption peak in the longitudinal direction was slightly blue-shifted. FIG. 28B and Table 5 show the hydrodynamic diameter of the end-to-end assembled AuNR cluster in deionized water or PBS at different temperatures. The longitudinal and transverse average diameters of the original AuNR were 2.0±0.1 nm and 60.9±0.5 nm, respectively. The diameter of the AuNR nanocluster in deionized water was 5.1 nm, 101.8 nm and 499.5 nm, which suggests the presence of both the individual AuNR and the end-to-end assembly AuNR. When the nanocluster was present in PBS of 20° C., the diameter was 57.9 nm and 455.3 nm due to the increased ionic strength. At 50° C., which is higher than the transition temperature of the poly(AAc-b-NIPAM), the nanogap between the AuNR was decreased due to the collapse of the NIPAM block and significant decrease in diameter. As seen from FIG. 28C, after the oxidation polymerization to poly(aniline) on the end-to-end assembled anisotropic AuNR cluster and silver reduction, new Ag absorption peaks appeared in the range of 350-450 nm and the longitudinal plasmon peak was slightly blue-shifted as compared to the Janus nanoparticle having the original AuNR as a seed due to the end-to-end assembled AuNR. FIG. 28D) shows the hydrodynamic diameter of the anisotropic bimetal nanorod cluster-polymer Janus nanostructure formed from end-to-end assembly of AuNR. The average diameter of the Janus nanostructure in deionized water was 388 nm and that of the nanoparticle cluster consisting of the original AuNR was 246.4±30.7 nm. When the Janus nanostructure was suspended in PBS of 20° C., the average diameter was 735 nm, suggesting partial aggregation between the bimetal nanorod cluster part of the Janus nanostructure. However, at 50° C., which is above the LCST, the hydrodynamic diameter was decreased to 590 nm due to the decreased interparticle gap between adjacent nanorods caused by the collapse of the NIPAM block.

FIG. 29A shows the relative Raman shift of the MGITC ($10^{-6}$ M)-labeled AuNR and the side-by-side assembled AuNR cluster containing the same. As the MGITC was fixed on the AuNR surface through the isothiocyanate group (—N=C=S) of the MGITC, the Raman intensity of the MGITC embedded in the interparticle junction between the adjacent AuNRs of the side-by-side assembled nanocluster was improved about 11.0-fold as compared to the Raman intensity of the MGITC fixed on the AuNR (original AuNP) surface. This SERS intensity for MGITC of the Janus nanostructure was about 6.53-fold higher at 1617 $cm^{-1}$ as compared to the SERS intensity of the MGITC fixed on the AuNR (original AuNP) surface. In addition, the relative Raman spectra of the end-to-end assembled AuNR cluster and the Janus nanostructure containing the same in deionized water and PBS at room temperature was measured, as shown in FIG. 29B). After the self-assembly, MGITC was introduced to investigate the SERS efficiency. When compared with the individual AuNR, the Raman intensity of the end-to-end assembled AuNR nanocluster in deionized water was remarkably increased up to 38.2-fold. The high curvature of the AuNR resulted in significant enhancement of electromagnetic field and the Raman intensity of the end-to-end assembled AuNR nanocluster was remarkably increased as compared to the individual AuNR. The SERS intensity of the Janus nanostructure was increased 17.3-fold as compared to the individual AuNR.

FIGS. 30A-30F shows the TEM images of the AuNR, the asymmetric bimetal nanorod-polymer Janus nanostructure using the AuNR as a seed, the side-by-side self-assembled AuNR nanocluster and the anisotropic bimetal nanorod cluster-polymer Janus nanostructure containing the same, respectively, for characterization of size and shape.

FIGS. 31A-31D shows the TEM images of the end-to-end self-assembled AuNR nanocluster and the anisotropic bimetal nanorod cluster-polymer Janus nanostructure containing the same at various magnifications for characterization of size and shape.

What is claimed is:

1. A self-assembled bimetal-polymer Janus nanostructure having a superparticular structure comprising:
   a nanocluster core comprising a plurality of bimetal nanoparticles, each of the plurality of bimetal nanoparticles comprises a first metal and a second metal surrounding a surface of the first metal; and
   a conductive polymer shell comprising a plurality of polymer parts, each of the plurality of polymer parts extends radially from a surface of the nanocluster core,
   wherein the plurality of bimetal nanoparticles are directionally self-assembled through a hydrophobic interaction by a plurality of octadecylamine functional groups covalently attached to surfaces of the plurality of bimetal nanoparticles, and
   wherein an average diameter of the self-assembled bimetal-polymer Janus nanostructure is 167 nm to 272.3 nm.

2. The self-assembled bimetal-polymer Janus nanostructure according to claim 1, wherein the first metal and the second metal are respectively selected from the group consisting of silver, gold, copper and a mixture thereof and the first metal and the second metal are not identical.

3. The self-assembled bimetal-polymer Janus nanostructure according to claim 1, wherein the conductive polymer is at least one selected from a group consisting of polypyrrole, polythiophene, poly(3,4-ethylenedioxythiophene) (PEDOT) and polyaniline.

4. The self-assembled bimetal-polymer Janus nanostructure according to claim 1, wherein the bimetal nanocluster core further comprises a Raman dye.

5. A metal nanoprobe for biosensing and/or bioimaging measurement based on surface-enhanced Raman scattering (SERS) comprising the Janus nanostructure according to claim 4.

6. A fluorescence-based metal nanoprobe for biosensing and/or bioimaging measurement comprising the Janus nanostructure according to claim 1.

7. A drug delivery system comprising the Janus nanostructure according to claim 1.

8. A method for preparing the self-assembled bimetal-polymer Janus nanostructure of claim 1, comprising:
   i) preparing a metal nanoparticle forming a seed;
   ii) adding the seed metal nanoparticle to an aqueous solution in which a conductive polymer monomer and a surfactant are dissolved;
   iii) conducting an oxidation-reduction reaction between a metal ion and the conductive polymer monomer by adding a metal ion solution to the solution in which the seed metal nanoparticle is added in ii);
   iv) preparing a bimetal-polymer Janus nanoparticle by forming a bimetal nanoparticle part as the metal ion is reduced by receiving an electron donated by the conductive polymer and is deposited on the surface of the seed metal nanoparticle and forming a conductive polymer part asymmetrically as the conductive polymer monomer is oxidized, is deposited on only one side of the bimetal nanoparticle part and grows into a conductive polymer;

v) adding ODA (octadecylamine) to a solution comprising the Janus nanoparticle; and vi) forming the bimetal nanocluster core and the conductive polymer shell located radially around the core through self-assembly as the bimetal nanoparticle in the Janus nanoparticle is covalently bonded to the ODA.

9. The method for preparing a self-assembled bimetal-polymer Janus nanostructure according to claim 8, which further comprises, after iv), attaching a Raman dye on the surface of the bimetal nanoparticle.

10. The method for preparing a self-assembled bimetal-polymer Janus nanostructure according to claim 8, wherein the seed metal in i) is selected from a group consisting of gold, silver, coper and a mixture thereof and the metal ion in iii) is selected from a group consisting of gold ion, silver ion, copper ion and a mixture thereof.

11. The method for preparing a self-assembled bimetal-polymer Janus nanostructure according to claim 8, wherein the conductive polymer in ii) is at least one selected from a group consisting of polypyrrole, polythiophene, poly(3,4-ethylenedioxythiophene) (PEDOT) and polyaniline.

12. The method for preparing a self-assembled bimetal-polymer Janus nanostructure according to claim 8, wherein the growth into the conductive polymer in iv) is achieved by surface-templated polymerization.

13. A method for detecting a target material based on surface-enhanced Raman scattering (SERS), comprising:
   a) preparing a sample solution comprising a target material to be detected;
   b) immobilizing a first antibody for the target material onto a magnetic nanoparticle;
   c) immobilizing a second antibody for the target material onto the metal nanoprobe according to claim 5;
   d) forming an immune complex wherein the target material and the first antibody of the magnetic nanoparticle are conjugated by adding the first antibody-immobilized magnetic nanoparticle of b) to the sample solution of a);
   e) forming a sandwich immune complex of the second antibody of the metal nanoprobe, the target material and the first antibody of the magnetic nanoparticle by adding the second antibody-immobilized metal nanoprobe of c) to the solution comprising the first antibody-conjugated immune complex of d);
   f) separating the magnetic nanoparticle and the metal nanoprobe not forming the sandwich immune complex using a magnetic field; and
   g) measuring a Raman signal of the sandwich immune complex.

14. The method for detecting a target material based on surface-enhanced Raman scattering (SERS) according to claim 13, wherein the target material is a protein or a pathogen.

\* \* \* \* \*